(12) United States Patent
Love et al.

(10) Patent No.: US 8,084,602 B2
(45) Date of Patent: Dec. 27, 2011

(54) PORPHYRIN DERIVATIVES AND THEIR USE IN PHOTODYNAMIC THERAPY

(75) Inventors: William Love, Horsham (GB); Derek Brundish, Horsham (GB); William Rhys-Williams, Burgess Hill (GB); Xiang Dong Feng, Qingdao (CN); Benoit Pugin, Muenchenstein (CH)

(73) Assignee: Destiny Pharma Limited, Basel (CH)

( * ) Notice: Subject to any disclaimer, the term of this patent is extended or adjusted under 35 U.S.C. 154(b) by 1222 days.

(21) Appl. No.: 11/562,183

(22) Filed: Nov. 21, 2006

(65) Prior Publication Data
US 2007/0281915 A1 Dec. 6, 2007

Related U.S. Application Data

(62) Division of application No. 10/744,863, filed on Dec. 23, 2003, now Pat. No. 7,244,841.

(30) Foreign Application Priority Data

Dec. 23, 2002 (GB) .................................. 0229742.2

(51) Int. Cl.
*C07D 487/22* (2006.01)
*C07B 47/00* (2006.01)
(52) U.S. Cl. ...................................................... 540/145
(58) Field of Classification Search .................. 540/145; 514/185, 410; 424/9.362, 9.61; 534/15
See application file for complete search history.

(56) References Cited

U.S. PATENT DOCUMENTS

| | | | |
|---|---|---|---|
| 4,318,883 A | 3/1982 | Polony et al. | |
| 4,775,625 A | 10/1988 | Sieber | |
| 4,851,403 A | 7/1989 | Picker | |
| 4,878,891 A | 11/1989 | Judy et al. | |
| 4,892,941 A | 1/1990 | Dolphin | |
| 4,917,784 A | 4/1990 | Shelnutt | |
| 4,962,197 A | 10/1990 | Foley et al. | |
| 4,986,256 A | 1/1991 | Cohen | |
| 4,987,226 A | 1/1991 | Buchler | |
| 5,041,209 A | 8/1991 | Cha | |
| 5,043,101 A | 8/1991 | Gordon | |
| 5,077,394 A | 12/1991 | Dolphin | |
| 5,109,016 A | 4/1992 | Dixon | |
| 5,141,911 A | 8/1992 | Meunier | |
| 5,149,697 A | 9/1992 | Johnson | |
| 5,179,120 A | 1/1993 | Vogel et al. | |
| 5,192,788 A | 3/1993 | Dixon | |
| 5,192,797 A | 3/1993 | Raizon | |
| 5,212,300 A | 5/1993 | Ellis, Jr. et al. | |
| 5,223,494 A | 6/1993 | Kappas | |
| 5,236,914 A | 8/1993 | Meunier | |
| 5,262,532 A | 11/1993 | Tweedle | |
| 5,268,371 A | 12/1993 | Mauclaire | |
| 5,280,115 A | 1/1994 | Ellis, Jr. et al. | |
| 5,281,616 A | 1/1994 | Dixon | |
| 5,284,647 A | 2/1994 | Niedballa | |
| 5,312,896 A | 5/1994 | Bhardwaj | |
| 5,345,008 A | 9/1994 | Lyons et al. | |
| 5,382,662 A | 1/1995 | Ellis | |
| 5,397,777 A | 3/1995 | Fiel | |
| 5,409,900 A | 4/1995 | Vogel et al. | |
| 5,479,120 A | 12/1995 | McEwan | |
| 5,489,716 A | 2/1996 | Ellis, Jr. et al. | |
| 5,493,017 A | 2/1996 | Therien et al. | |
| 5,545,516 A | 8/1996 | Wagner | |
| 5,563,132 A | 10/1996 | Bodaness | |
| 5,571,908 A | 11/1996 | Wijesekera | |
| 5,599,924 A | 2/1997 | Therien et al. | |
| 5,603,820 A | 2/1997 | Malinski | |
| 5,629,198 A | 5/1997 | Mizumoto | |
| 5,637,608 A | 6/1997 | Vogel et al. | |
| 5,663,328 A | 9/1997 | Ellis, Jr. et al. | |
| 5,674,467 A | 10/1997 | Maier | |

(Continued)

FOREIGN PATENT DOCUMENTS
EP 0 196 515 10/1986
(Continued)

OTHER PUBLICATIONS

Hamblin et al., "Rapid Control of Wound Infections . . .", Photochemistry and Photobiology, 2002 75(1) pp. 51-57.*
Bruce, et al, "Mesomorphic metalloporphyrins showing calamitic mesophases," *J. Mater. Chem.*, 2(3): 363-364 (1992).
Brückner, et al., "Novel and improved synthesis of 5,15-diphenylporphoryin and its dipyrrolic precursors,"*J. Porphryins. Phthalocyanines*, 2: 455-465 (1998).
Geier III, et al., "A survey of acid catalysts in dipyrromethanecabinol condensations leading to *meso*-substituted porphyrins," *J. Porphryins. Phthalocyanines*, 5: 810-823 (2001).
Lindsey, "Synthesis of meso-Substituted Porphyrins," *The Porphyrin Handbook*, Kadish, Smith, and Guilard (eds.), Academic Press, Inc.: New York, pp. 45-118 (2000).

(Continued)

*Primary Examiner* — Paul V. Ward
(74) *Attorney, Agent, or Firm* — Pabst Patent Group LLP

(57) ABSTRACT

A compound of formula I:

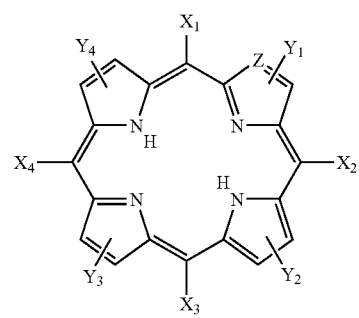

wherein $X_1$, $X_2$, $X_3$, $X_4$, $Y_1$, $Y_2$, $Y_3$, $Y_4$ and Z have meanings given in the description, and metallated forms of such compounds, which are useful in the treatment of medical conditions for which a photodynamic compound is indicated. Pharmaceutical formulations and methods of treatment of a medical condition for which a photodynamic agent is indicated are also disclosed. Sterilizing solutions comprising a compound of the invention, and the use thereof, are also disclosed.

53 Claims, 24 Drawing Sheets

U.S. PATENT DOCUMENTS

| | | | |
|---|---|---|---|
| 5,703,230 | A | 12/1997 | Boyle et al. |
| 5,756,723 | A | 5/1998 | Therien et al. |
| 5,760,217 | A | 6/1998 | Wijesekera |
| 5,767,272 | A | 6/1998 | Wijesekera |
| 5,773,417 | A | 6/1998 | Bonaventura |
| 5,847,114 | A | 12/1998 | Thetford et al. |
| 5,849,259 | A | 12/1998 | Hilger |
| 5,864,044 | A | 1/1999 | Van Lier et al. |
| 5,877,165 | A | 3/1999 | Miura |
| 5,929,064 | A | 7/1999 | Goel |
| 5,990,363 | A | 11/1999 | Wijesekera |
| 5,994,339 | A | 11/1999 | Crapo |
| 5,998,128 | A | 12/1999 | Roelant |
| 6,002,026 | A | 12/1999 | Groves |
| 6,004,530 | A | 12/1999 | Sagner |
| 6,013,241 | A | 1/2000 | Marchal |
| 6,028,025 | A | 2/2000 | Ying |
| 6,060,467 | A | 5/2000 | Buelow |
| 6,066,628 | A | 5/2000 | Stojiljkovic |
| 6,087,493 | A | 7/2000 | Wheelhouse |
| 6,103,892 | A | 8/2000 | Breslow |
| 6,104,714 | A | 8/2000 | Baudelot |
| 6,107,326 | A | 8/2000 | Jori |
| 6,107,480 | A | 8/2000 | Funken |
| 6,124,452 | A | 9/2000 | DiMagno |
| 6,127,356 | A | 10/2000 | Crapo |
| 6,136,841 | A | 10/2000 | Platzek |
| 6,147,070 | A | 11/2000 | Facchini |
| 6,187,572 | B1 | 2/2001 | Platz |
| 6,194,566 | B1 | 2/2001 | Platzek |
| 6,208,553 | B1 | 3/2001 | Gryko et al. |
| 6,245,707 | B1 | 6/2001 | Chu |
| 6,251,367 | B1 | 6/2001 | Platzek |
| 6,272,038 | B1 | 8/2001 | Clausen et al. |
| 6,324,091 | B1 | 11/2001 | Gryko et al. |
| 6,362,175 | B1 | 3/2002 | Vinogradov |
| 6,368,396 | B1 | 4/2002 | Nohr |
| 6,368,558 | B1 | 4/2002 | Suslick |
| 6,372,727 | B1 | 4/2002 | Crow |
| 6,399,769 | B1 | 6/2002 | Nohr |
| 6,403,788 | B1 | 6/2002 | Meunier |
| 6,407,330 | B1 | 6/2002 | Lindsey et al. |
| 6,420,553 | B1 | 7/2002 | Inoue |
| 6,420,648 | B1 | 7/2002 | Lindsey |
| 6,433,162 | B1 | 8/2002 | Nickel et al. |
| 6,436,171 | B1 | 8/2002 | Wang |
| 6,444,194 | B1 | 9/2002 | Robinson |
| 6,448,239 | B1 | 9/2002 | Groves |
| 6,451,942 | B1 | 9/2002 | Li |
| 6,479,477 | B1 | 11/2002 | Crapo |
| 6,495,102 | B1 | 12/2002 | Suslick |
| 6,524,379 | B2 | 2/2003 | Nohr |
| 6,544,975 | B1 | 4/2003 | Crapo |
| 6,566,517 | B2 | 5/2003 | Miura |
| 6,573,258 | B2* | 6/2003 | Bommer et al. ............ 514/185 |
| 6,582,930 | B1 | 6/2003 | Ponomarev |
| 6,583,132 | B1 | 6/2003 | Crapo |
| 6,596,935 | B2* | 7/2003 | Lindsey et al. |
| 6,620,805 | B1 | 9/2003 | Takle |
| 6,630,128 | B1* | 10/2003 | Love et al. ............... 424/9.362 |
| 6,642,376 | B2* | 11/2003 | Lindsey et al. |
| 6,727,240 | B1 | 4/2004 | Neurath |
| 6,759,403 | B2 | 7/2004 | Miura |
| 6,812,343 | B2* | 11/2004 | Osuka |
| 6,818,763 | B2 | 11/2004 | Vukovich |
| 6,827,926 | B2 | 12/2004 | Robinson |
| 6,833,227 | B2 | 12/2004 | Tanaka |
| 6,857,926 | B1 | 2/2005 | Sulcs |
| 6,900,197 | B2 | 5/2005 | Szabo |
| 6,916,799 | B2 | 7/2005 | Fridovich |
| 6,951,935 | B2* | 10/2005 | Zhang et al. |
| 6,969,707 | B2 | 11/2005 | Groves |
| 6,995,260 | B2 | 2/2006 | Wu |
| 7,008,937 | B2 | 3/2006 | Bommer |
| 7,025,734 | B1 | 4/2006 | Ellis |
| 2002/0042407 | A1 | 4/2002 | Fridovich et al. |
| 2002/0177704 | A1 | 11/2002 | Sakata |
| 2002/0183245 | A1* | 12/2002 | Hasan et al. |
| 2003/0032634 | A1 | 2/2003 | Piganelli |
| 2003/0032799 | A1 | 2/2003 | Miura |
| 2003/0050297 | A1 | 3/2003 | Crapo |
| 2003/0055032 | A1 | 3/2003 | Groves |
| 2003/0096721 | A1 | 5/2003 | Hage |
| 2003/0100752 | A1 | 5/2003 | Robinson |
| 2003/0105069 | A1 | 6/2003 | Robinson |
| 2003/0166298 | A1 | 9/2003 | Suslick |
| 2003/0176326 | A1* | 9/2003 | Nifantiev |
| 2003/0225364 | A1 | 12/2003 | Kraft |
| 2004/0014738 | A1* | 1/2004 | Dubbelman et al. |
| 2004/0019031 | A1 | 1/2004 | Crapo |
| 2004/0019204 | A1 | 1/2004 | Che |
| 2004/0023941 | A1 | 2/2004 | Crapo |
| 2004/0058902 | A1 | 3/2004 | Batinic-Haberle |
| 2004/0063681 | A1 | 4/2004 | Che |
| 2004/0116403 | A1 | 6/2004 | Klimko |
| 2004/0127479 | A1 | 7/2004 | Depke |
| 2004/0137281 | A1 | 7/2004 | Ishikawa |
| 2004/0169463 | A1 | 9/2004 | Burn |
| 2004/0208855 | A1 | 10/2004 | Allison |
| 2004/0210048 | A1 | 10/2004 | Vukovich |
| 2004/0234495 | A1 | 11/2004 | Maeda |
| 2004/0236157 | A1 | 11/2004 | Heilgendorff |
| 2004/0254155 | A1 | 12/2004 | Bommer |
| 2005/0008687 | A1 | 1/2005 | Yuasa |
| 2005/0029470 | A1 | 2/2005 | Muehlig |
| 2005/0090428 | A1 | 4/2005 | Compans |
| 2005/0112058 | A1 | 5/2005 | Laster |
| 2005/0124596 | A1 | 6/2005 | Zhang |
| 2005/0137180 | A1 | 6/2005 | Robinson |
| 2006/0003982 | A1 | 1/2006 | Williams |
| 2006/0007889 | A1 | 1/2006 | Khan |
| 2006/0013774 | A1 | 1/2006 | Port |
| 2006/0030718 | A1 | 2/2006 | Zhang |
| 2006/0041121 | A1 | 2/2006 | Che |
| 2006/0074062 | A1 | 4/2006 | Fridovich |
| 2006/0089344 | A1 | 4/2006 | Abouabdellah |
| 2006/0129041 | A1 | 6/2006 | Ellis |

FOREIGN PATENT DOCUMENTS

| | | |
|---|---|---|
| EP | 0350395 | 1/1990 |
| EP | 0350948 | 1/1990 |
| EP | 0 906 758 | 4/1999 |
| EP | 1 197 147 | 4/2002 |
| EP | 1 197 229 | 4/2002 |
| EP | 1 558 616 | 8/2005 |
| FI | 2002 A 000200 | 4/2004 |
| FR | 2 566 766 | 1/1986 |
| GB | 2 397 067 | 7/2004 |
| JP | 5 800 0981 | 1/1983 |
| JP | 6 118 9284 | 8/1986 |
| PT | 102572 | 9/2002 |
| PT | 102581 | 12/2002 |
| RU | 2 238 950 | 10/2004 |
| SU | 721 442 | 3/1980 |
| WO | WO 91/16053 | 10/1991 |
| WO | WO 93/08455 | 4/1993 |
| WO | WO 95/33463 | 12/1995 |
| WO | WO 96/05862 | 2/1996 |
| WO | WO 96/31452 | 10/1996 |
| WO | WO 98/30102 | 7/1998 |
| WO | WO 98/31219 | 7/1998 |
| WO | WO 98/33503 | 8/1998 |
| WO | WO 98/39011 | * 9/1998 |
| WO | WO 98/52610 | * 11/1998 |
| WO | WO 00/09111 | * 2/2000 |
| WO | WO 00/12512 | * 3/2000 |
| WO | WO 00/52012 | * 9/2000 |
| WO | WO 00/74674 | * 12/2000 |
| WO | WO 01/26655 | 4/2001 |
| WO | WO 01/96343 | 12/2001 |
| WO | WO 02/10173 | 2/2002 |
| WO | WO 02/13820 | 2/2002 |
| WO | WO 02/30190 | 4/2002 |
| WO | WO 02/30475 | 4/2002 |
| WO | WO 03/008430 | 1/2003 |
| WO | WO 03/057176 | 7/2003 |
| WO | WO 03/086389 | 10/2003 |

| WO | WO 2004/035590 | 4/2004 |
| WO | WO 2004/046151 | 6/2004 |
| WO | WO 2004/056828 | 7/2004 |
| WO | WO 2004/069273 | 8/2004 |
| WO | WO 2006/000765 | 1/2005 |
| WO | WO 2005/058909 | 6/2005 |
| WO | WO 2005/077269 | 8/2005 |

OTHER PUBLICATIONS

Manka and Lawrence, "High yield synthesis of 5,15-diarylporphyrins," Tetrahedron Lett., 30: 6989-6992 (1989).

Taniguchi, et al., "Imine-substituted dipyrromethanes in the synthesis of porphyrins bearing one or two meso substituents," J. Porphryins. Phthalocyanines, 9: 554-574 (2005).

Wang and Bruce, "Control of intermolecular porphyrin π-π interactions: low-melting liquid-crystal porphyrins with calamitic mesophases," Chem. Commun., 2505-2506 (1996).

Declaration of Professor David Dolphin, submitted in prosecution of European Patent No. 1 578 750, submitted Jun. 6, 2009.

Adler, et al., "On the preparation of Metahhoporphyrins" J. Inorg. Nucl. Chem. 32:2443-2445 (1970).

Ali and Van Lier, "Metal complexes as photo- and radiosensitizers", Chem. Rev., 99(9):2379-450 (1999).

Baker and Cotten, "Delivery of bacterial artificial chromosomes into mammalian cells with psoralen-inactivated adenovirus carrier", Nucleic Acids Res., 25(10):1950-6 (1997).

Berg, "Remote Guidance, Robotic Devices Stir Interest of Surgeons," BBI Newsletter (2000).

Bernadou, et al., "Potassium monopersulfate and a water-soluble manganese porphyrin complex, [Mn(TMPyP)](OAc)5, as an efficient reagent for the oxidative cleavage of DNA", Biochemistry, 28(18):7268-75 (1989).

Bigey, et al.,"Preparation and Characterization by electrospray mass spectrometry of cationic metalloporphyrin DNA cleavers," Bull. Soc. Chim. Fr., 133:679-689 (1996).

Borocci, et al.,"Characterization of mixed monolayers of phosphatidylcholine and a dicationic gemini surfactant SS-1 with a langmuir balance: effects of DNA," Biophys J. 81(4):2135-43 (2001).

Branland, et al. "Nitroglycosylated meso-arylporphyrins as photoinhibitors of gram positive bacteria." Bioorg Med Chem Lett. 8(21):3007-10(1998).

Caminos, et al., "Photodynamic inactivation of Escherichia coli by novel meso-substituted porphyrins by 4-(3-N,N,N-trimethylammoniumpropoxy)phenyl and 4-(trifluoromethyl)phenyl groups", Photochem. Photobiol. Sci., 5(1):56-65 (2006).

Casas, et al.,"Synthesis of Cationic Metalloporphyrin Precursors related to the Design of DNA Cleavers," J. Org. Chem. 58:2913-2917(1993).

Chan and Lau, "Syntheses of Acyl Rhodium Porphyrins by Aldehydic Carbon-Hydrogen Bond Activation with Rh(III) Porphyrin Chloride and Methyl," organometallics 25:260-265 (2006).

Chang, et al., "Fluoresecence Intensity Changes for Anthrylazacrown Ethers by Paramagnetic Metal Cations," Bull. Korean Chem. Soc. 20(7) 796-800 (1999).

Che, et al., "Gold(III) porphyrins as a new class of anticancer drugs: cytotoxicity, DNA binding and induction of apoptosis in human cervix epitheloid cancer cells", Chem. Commun. (Camb), (14):1718-9 (2003).

Chitta, et al., "Electrochemical, spectral, and computational studies of metalloporphyrin dimers formed by cation complexation of crown ether cavities", Inorg. Chem., 43(22):6969-78 (2004).

Collman, et al., "Systematic variation of metal-metal bond order in metalloporphyrin dimmers", Proc. Natl. Acad. Sci. U.S.A., 80(24):7684-7688 (1983).

Collman, et al., "Spectroscopic comparisons of MoW(porphyrin)$_2$ Heterodimers with Homologous Mo$_2$ and W$_2$ Quadruple Bonds: A dynamic NMR and Resonance Raman Study" JACS 120:1456-65 (1998).

Collman and Woo, "Rotational barrier of a molybdenum-molybdenum quadruple bond", Proc. Natl. Acad. Sci. U.S.A., 81(8):2592-2596 (1984).

Cui and Wayland. "Activation of C-H / H-H bonds by rhodium(II) porphyrin bimetalloradicals", J. Am. Chem. Soc., 126(26):8266-74 (2004).

Desandre, et al., "The effectiveness of oral tin mesoporphyrin prophylaxis in reducing bilirubin production after an oral heme load in a transgenic mouse model", Biol. Neonate, 89(3):139-46 (2006).

Ding, et al., "Syntheses and in vitro evaluation of water-soluble "cationic metalloporphyrin-ellipticine" molecules having a high affinity for DNA", J. Med. Chem., 34(3):900-6 (1991).

Fu and Wayland, "Equilibrium thermodynamic studies in water: reactions of dihydrogen with rhodium(III) porphyrins relevant to Rh-Rh, Rh-H, and Rh-OH bond energetics", J. Am. Chem. Soc., 126(8):2623-31 (2004).

Fukushima, et al., "Synthesis and properties of rhodium(III) porphyrin cyclic tetramer and cofacial dimmer", Inorg. Chem., 42(10):3187-93 (2003).

Gebauer, et al., "Nuetral π-Radicals of lithium porphyrins: synthesis and characterization," J. Chem. Soc.Dalton Trans. 111-112 (2000).

Godbey, et al., "Size matters: molecular weight affects the efficiency of poly(ethylenimine) as a gene delivery vehicle", J. Biomed. Mater. Res., 45(3):268-75 (1999).

Hamblin and Hassan, "Photodynamic therapy: a new antimicrobial approach to infectious disease?", Photochem. Photobiol. Sci., 3(5):436-50 (2004).

Hamstra, et al., "Molybdenum(V) on an Oxide String. Synthesis and Structure of the Novel Linear Trinuclear Complex {[MoO(TPP)][O-Mo(TPP)-O][MoO(TPP)]}ClO(4)", Inorg. Chem., 38(15):3554-3561 (1999).

Hamstra, et al., "Molybdenum(V) on an oxide string. Formation and solution stability of the linear complex (mu-transdioxo(tetraphenylporphyrinato)molybdenato(V))-bis(oxo(tetraphenylporphyrinato)molybdenum(V)) perchlorate", Inorg. Chem., 39(7):1454-7 (2000).

Harroti, et al.,"Anion-Selective Electrods Based on Porphrin Complexes of Tetravalent Metal Ions," Anal Sci. 17:1353-1356 (2001).

Helander, et al., "Polyethyleneimine is an effective permeabilizer of gram-negative bacteria", Microbiology, 143 (Pt 10):3193-9 (1997).

Hermann, et al, "Heterogeneous metal-insertion: a novel reaction with porphyrins," Can. J. Chem. 56:184-1087 (1978).

Ito, "Cellular and subcellular mechanisms of photodynamic action: the 1O2 hypothesis as a driving force in recent research", Photochem. Photobiol., 28(4-5):493-508 (1978).

Jori and Brown, "Photosensitized inactivation of microorganisms", Photochem. Photobiol. Sci., 3(5):403-5 (2004).

Kim, et al., Synthesis and Crystal Structure of an Organoimido Molybdenum (V) Porphyrin Salt, [Mo(Nme)(TPP)(H$_2$O)][I$_3$](TPP=Tetraphenylporphyrin) Inorg. Chem. 34:2483-2486 (1995).

Kim, et al.,"Synthesis and Rotational Barrier of Tungsten(II)Porphyrin Dimer" Polyherdron 15(1)57-62 (1996).

Ladan, et al., "The antibacterial activity of haemin compared with cobalt, zinc and magnesium protoporphyrin and its effect on potassium loss and ultrastructure of Staphylococcus aureus", FEMS Microbiol. Lett., 112(2):173-7 (1993).

Lambrechts, et al., "Effect of monovalent and divalent cations on the photoinactivation of bacteria with meso-substituted cationic porphyrins", Photochem. Photobiol., 79(3):297-302 (2004).

Leanord and Smith,"Model Systems for cytochrome P450 Dependent Mono-oxygenases. Part 7. Alkene Epoxidation by Iodosylbensene Cataysed by Ionic Iron(III) Tetraarylporphyrins Supported on Ion-exchnage Resins," J. Chem. Soc. Perkin Trans. 2 2::1917-1923 (1990).

Lewis, Hawley's Condensed Chemical Dictionary, pp. 718, 803, and 990.

Maisch, et al., "Antibacterial photodynamic therapy in dermatology", Photochem. Photobiol. Sci., 3(10):907-17 (2004).

Malik, et al., "Effects of photoactivtaed haematoporphyrin derivative on bacteria and antibiotic resistance," Microbios. Lett., 21(83-84):103-112 (1982).

Maliyackel, et al., "Photoinduced oxidation of a water-soluble manganese(III) porphyrin", Proc. Natl. Acad. Sci. U.S.A., 83(11):3572-3574 (1986).

Manka and Lawrence, "High Yeild Synthesis of 5,15-Diarylporphyrins," *Tet. Lett.* 30(50):6989-6992 (1989).

Mestre, et al., "Influence of the nature of the porphyrin ligand on the nuclease activity of metalloporphyrin-oligonucleotide conjugates designed with cationic, hydrophobic or anionic metalloporphyrins", *Nucleic Acids Res.*, 25(5):1022-7 (1997).

Milanesio, et al., "Photodynamic studies of metallo 5,10,15,20-tetrakis(4-methoxyphenyl) porphyrin: photochemical characterization and biological consequences in a human carcinoma cell line", *Photochem. Photobiol.*, 74(1):14-21 (2001).

Nasim and Brychy, "Genetic effects of acridine compounds", *Mutat. Res.*, 65(4):261-88 (1979).

Neely and Bottomley, "Inter-Metal Nitrogen Atom Transfer Reactions between Nitridochromium(V) and Chromium(III) Porphyrins," *Inorg. Chem.* 36:5432-5434 (1997).

Nistri, et al., "A novel synthesis of 5,15-trimethylammonium substituted porphyrins and their evaluation as potential antimicrobial photosensitizers," *J. Porphyrins and Phthalocyaninies* 9:290-7 (2005).

Nitzan, et al. "Characterization of hemin antibacterial action on *Staphylococcus aureus*," *FEMS Micorbiol. Lett.* 48:401-406 (1987).

Orenstein, et al. "The use of porphyrins for eradication of *Staphylococcus aureus* in burn wound victims" *FEMS Immunol. Med. Microbiol.* 19:307-14 (1998).

Parker; McGraw-Hill Encyclopeddia of Chemistry (2$^{nd}$ Edition) pp. 637.

Pitie, et al. "Preferential hydroxylation by the chemical nuclease meso-tetrakis-(4-N-methylpyridiniumyl)porphyrinatomanganeseIII pentaacetate/KHSO5 at the 5' carbon of deoxyriboses on both 3' sides of three contiguous A.T base pairs in short double-stranded oligonucleotides," *PNAS* 89:3967-3971 (1992).

Pratviel, et al. "Mechanism of DNA cleavage by cationic manganese porphyrins: hydroxylations at the 1'-carbon and 5'-carbon atoms of deoxyriboses as initial damages," *Nucleic Acids Res.* 25;19(22):6283-8(1991).

Renner and Fadjer "Oxidative chemistry of Nickel Porphyrins" *J. Biol. Inorg. Chem.* 6:823-830 (2001).

Ribeiro "Synthesis of New Cationic Metalloporphyrins and Heterodimer formation with anionic metallophthalocyanines," *J. Braz. Chem. Soc.* 14(6):914-21 (2003).

Sakurai, et al. "A new candidate for insulinomimetic vanadium complex: synergism of oxovanadium(IV)porphyrin and sodium ascorbate," *Bioorg Med Chem Lett.* 14(5):1093-6(2004).

Salmon-Divon, et al. "Mechanistic aspects of *Escherichia coli* photodynamic inactivation by cationic tetra-meso(N-methylpyridyl)porphine," *Photochem Photobiol Sci.* 3(5):423-9(2004).

Sisemore, et al "Metalloporphyrin Peroxo Complexes of Iron(III), Manganese(III), and Titanium(IV). Comparative Studies Demonstrating That the Iron(III) Complex Is Extremely Nucleophilic," *Inorg. Chem.* 36:979-984 (1997).

Smith and Lower "The mechanism of the reaction between t-butyl hydroperoxide and 5,10,15,20-Tetra(N-methyl-4-pyridyl) porphyrinatoiron (III) pentachloride in aqueous solution," *J. Chem. Soc. Perkin. Trans.* 2:31-39 (1991).

Stojilijkovic,et al. "Non-iron metalloporphyrins: potent antibacterial compounds that exploit haem/Hb uptake systems of pathogenic bacteria," *Mol Microbiol.* 31(2):429-42(1999).

Sun,et al. "Reversible Electrochemical generation of a rhodium(II) porphyrin: Thwarting disproportionation with weakly coordinating anions," *Inorg. Chem.* 42:4507-4509 (2003).

Takehara,et al. "Tumour enhancement with newly developed Mn-metalloporphyrin (HOP-9P) in magnetic resonance imaging of mice," *Br J Cancer* 84(12):1681-5(2001).

Toffoli,et al., "In K562 leukemia cells treated with doxorubicin and hemin, a decrease in c-myc mRNA expression correlates with loss of self-renewal capability but not with erythroid differentiation," *Leuk Res.* 13(4):279-87 (1989).

Venezio,et al. "Bactericidal effects of photoradiation therapy with hematoporphyrin derivative," *J. Infect, Dis.* 151(1):166-9(1985).

Vzorov,et al. "Inactivation of human immunodeficiency virus type 1 by Porphyrins," *Antimicrob Agents Chemother.* 46(12):3917-25(2002).

Walshe, "Management of penicillamine nephropathy in Wilson's disease: a new chelating agent," *Lancet* 2(7635):1401-2(1969).

Wang, et al."Facile Syntheses of Titanium(II), Tin(II), and Vanadium(II) Porphyrin Complexes through Homogeneous Reduction. Reactivity of trans-(TTP)TiL(2) (L = THF, t-BuNC)," *Inorg Chem.* 37(1):5-9(1998).

Wang and Woo, "Facile Syntheses of Titanium(II), Tin(II), and Vanadium(II) Porphyrin Complexes through Homogeneous Reduction. Reactivity of trans-(TTP)TiL(2) (L = THF, t-BuNC)," *Inorg. Chem.* 37(1):5-9(1998).

Wilson, "Lethal photosensitisation of oral bacteria and its potential application in the photodynamic therapy of oral infections," *Photochem Photobiol Sci.* 3(5):412-8(2004).

Wong, et al. "Physiologically stable vanadium(IV) porphyrins as a new class of anti-HIV agents,"*Chem Commun (Camb).* (28):3544-6(2005).

Wu, et al. "Iron porphyrin treatment extends survival in a transgenic animal model of amyotrophic lateral sclerosis," *J. Neurochem.* 85(1):142-50(2003).

Zhou, et al. "Synthesis of rhodium porphyrin aryls via intermolecular arene carbon-hydrogen bond activation," *Inorg. Chim. Acta* 270:551-554 (1998).

Iritani, "The combinatorial enumeration of structural isomers of alkanes", *J. Chem. Software*, 5(2):65-80 (1999) (with English Abstract).

Maisch, et al., "Photodynamic effects of novel XF porphyrin derivatives on prokaryotic and eukaryotic cell", *Antimicrobial Agents and Chemotherapy*, 49(4):1542-1552 (2005).

Treibs & Haberle, "Concerning the synthesis and the electron spectrum of ms-substituted porphine", *Justus Liebigs Ann Chem*, 178:183-207 (1968) (with English Abstract).

Bellin, et al., "Effects of photodynamic action on *E. coli*", *Arch. Biochem. Biophys.* 132: 157-164 (1969).

Bertoloni, et al., "Photosensitizing activity of water- and lipid-soluble phthalocyanines on *Escherichia coli*,"*FEMS Microbiol. Lett.* 59: 149-155 (1990).

Bertoloni, et al., "Photosensitizing activity of water- and lipid-soluble phthalocyanines on prokaryotic and eukaryotic microbial cells," *Microbios*, 71: 33-46 (1992).

Borocci, et al., *Chemical Abstracts* 136: 69974 (2001) (abstract only).

Breuer, et al., "*Staphylococcus aureus*: colonizing features and influence of an antibacterial treatment in adults with atopic dermatitis," *Br. J. Dermatol.* 147: 55.61 (2002).

Brückner, et al., "Novel and improved syntheses of 5,15-diphenylporphyrin and its dipyrrolic precursors", *J. Porphyrins Phthalocyanines*, 2: 455-465 (1998).

Ceburkov & Gollnick, "Photodynamic therapy in dermatology," *Eur. J. Dermatol.* 10(7): 568-75 (2000).

Chen and Zhang, "Facile and efficient synthesis of *meso*-arylamino- and alkylamino-substituted porphyrins via palladium-catalyzed amination", *J. Org. Chem.*, 68:4432-38 (2003).

Dick, et al., "Molecular Encapsulation: Cyclodextrin-Based Analogues of Heme-Containing Proteins"*J. Am. Chem. Soc.* 114: 2664-2669 (1992).

Diwu & Lown, "Phototherapeutic potential of alternative photosensitizers to porphyrins", *Pharmacol. Ther.* 63: 1-35 (1994).

Dougherty, "An update on photodynamic therapy applications," *J. Clin. Laser Med. Surg.* 20(1): 3-7 (2002).

Drexler, et al., *Chemical Abstracts*, Database Accession No. 1998:433421.

Drexler, et al., "Design, synthesis and cleaving activity of an abiotic nuclease based on a Mn(III) porphyrin complex bearing two acridine moieties" *Chem. Comm.*, 1343-1344 (1998).

Ehrenberg, et al., "Fluorescence spectral changes of hematoporphyrin derivative upon binding to lipid vesicles, *Staphylococcus aureus* and *Escherichia coli* cells," *Photochem. and Photobiol.* 41: 429-435 (1985).

Feng and Senge, "An efficient synthesis of highly functionalized asymmetric porphyrins with organolithium reagents" *Journal of the Chemical Society, Perkin Transactions* 1:1030-1038 (2001).

Gao, et al., "Versatile synthesis of meso-aryloxy- and alkoxy-substituted porphyrins via palladium-catalyzed C-0 Cross-Coupling Reaction" *Org. Lett.*, 5(18):3261-64 (2003).
Geyer, et al., "Subophthalcyanines: Preparation, reactivity and physical properties", *Synthesis* 1139-1151 (1996).
Hamblin, et al., "Rapid control of wound infections by targeted photodynamic therapy monitored by in vivo bioluminescence imaging", *Photochem. Photobiol.* 75(1):51-7 (2002).
Hopper, "Photodynamic therapy: a clinical reality in the treatment of cancer," *Lancet Oncol.* 1: 212-219 (2000).
Jin, et al., "Combined effects of photodynamic and sonodynamic treatment on experimental skin cancer on C3H mice" *Photomedicine and Photobiology* 19:65-68 (1997).
Jorgensen & Ferraro, "Antimicrobial susceptibility testing: special needs for fastidious organisms and difficult-to-detect resistance mechanisms," *Clin. Infect. Dis.* 30(5): 799-808 (2000).
Kassab, et al., "Phthalocyanine-photosensitized inactivation of a pathogenic protozoan, *Acanthamkoeba palestinensis*", *Photochem. Photobiol. Sci.* 2(6): 668-672 (2003).
Kubát, et al., Interaction of novel cationic meso-tetraphenylporphyrins in the ground and excited states with DNA and nucleotides, *J. Chem. Soc. Perkin Trans.* 1:933-941 (2000).
Kuorevich, et al., "Syntheses of trisulfonated phthalocyanines and their derivatives using boron(III) subphthalocyanines as intermediates", *J. Org. Chem.* 61: 5706-5707 (1996).
Kuroyanagi, et al., "Extremely sensitive detection of photoresponses in ultrathin films containing porphyrins by the optical waveguide", *Chemical Abstracts* 124: 131104 (1995) (abstract only).
Li, et al., "A series of meso-tris(N-methyl-pyridiniumy1)-(4-alkylamidophenyl) porphyrins: Synthesis, interaction with DNA, and antibacterial activity", *Biochem. Biophys. Acta* 1354: 252-260 (1997).
Lin, et al., "Photosensitization, uptake, and retention of phenoxazine Nile blue derivatives in human bladder carcinoma cells," *Cancer Res.*51: 1109-1116 (1991).
Liu, et al., "Synthesis of tail-type pyridinium(triethylammonium)-porphyrin quaternary ammonium salt", *Chemical Abstracts* 133:104912 (2000) (abstract only).
Lou, et al., "Modulation of PDT-induced apoptosis by protein kinases and phosphatases" *Proc. SPIE* 2675:132-137 (1996).
Malik, et al., "Bactericidal effects of photoactivated porphyrins—an alternative approach to antimicrobial drugs," *J. Photochem. Photobiol. B* 5(3-4): 281-293 (1990).
Malik, et al., "Photodynamic inactivation of Gram-negative bacteria: problems and possible solutions," *J. Photochem. Photobiol. B* 14: 262-266 (1992).
Mehta, et al., "Cholate-interspersed porphyrin-anthraquinone conjugates: Photonuclease activity of large sized, 'tweezer-like' molecules", *J. Chem. Soc. Perkin. Trans 1*, 2177-2181 (1999).
Merchat, et al., "Meso-substituted cationic porphyrins as efficient photosensitizers of gram-positive and gram-negative bacteria," *J. Photochem. Photobiol. B.* 32: 153-157 (1996).
Merchat, et al., "Studies on the mechanism of bacteria photosensitization by meso-substituted cationic porphyrins," *J. Photochem. Photobiol B.* 35: 149-157 (1996).
Minnock, et al., "Photoinactivation of bacteria. Use of a cationic water-soluble zinc phthalocyanine to photoinactivate both gram-negative and gram-positive bacteria," *J. Photochem. Photobiol. B.* 32:159-164 (1996).
Moan, et al., "The mechanism of photodynamic inactivation of human cells in vitro in the presence of haematoporphyrin," *Br J Cancer* 39:398-407 (1979).
Monti, et al., "Micelle-bound metalloporphyrins as highly selective catalysts for the epoxidation of alkenes", *Chemical Abstracts* 129: 81626 (1998) (abstract only).
Mosmann, et al., "Rapid calorimetric assay for cellular growth and survival: application to proliferation and cytotoxicity assays," *J. Immunol. Meth.* 65: 55-63 (1983).
Munakata, et al., "Synthesis and nucleic acid-binding properties of water-soluble porphyrins appending platinum (II) Complexes", *Chem. Pharm. Bull*, 49(12):1573-80 (2001).

Nitzan & Ashkenazi, "Photoinactivation of Acinetobacter baumannii and *Escherichia coli* B by a cationic hydrophilic porphyrin at various light wavelengths", *Curr. Microbiol.* 42: 408-414 (2001).
Nitzan, et al., "Inactivation of gram-negative bacteria by photosensitized porphyrins," *Photochem. Photobiol.* 55: 89-96 (1992).
Nitzan, et al., "Eradication of Acinetobacter baumannii by photosensitized agents in vitro", *J. Photochem. Photobiol. B* 42: 211-218 (1998).
Okuno, et al., "An improved synthesis of surfactant porphyrins", *Synthesis* 537-539 (1980).
Petho, "The porphyrins in cancer and virus research", *Acta Physiol. Hungarica* 83(2)113-119 (1995).
Reddi, et al., "Photophysical properties and antibacterial activity of meso-substituted cationic porphyrins," *Photochem. Photobiol.* 75:(5) 462-470 (2002).
*Remington: The Science and Practice of Pharmacy*, 19th edition (Gennaro, ed.) Mack Publishing Company: Pennysylvania, pp. 1585-1597 (1995).
Sadick, "Current aspects of bacterial infections of the skin," *Dermatol. Clin* 15(2): 341-349 (1997).
Schneider & Wang, "DNA interactions with porphyrins bearing ammonium side chains", *J. Org. Chem.* 59: 7473-7478 (1994).
Segalla, et al., "Photophysical, photochemical and antibacterial photosensitizing properties of a novel octactaionic Zn(II)-phthalocyanine", *Photochem. Photobiol. Sci.* 1: 641-648 (2002).
Smith, "Photodynamic therapy," *Curr. Probl. Cancer* 26(2): 67-108 (2002).
Sol, et al., "Nitroglycosylated meso-arylporphyrins as photoinhibitors of gram positive bacteria", *Bioorg. Med. Chem. Lett.* 8: 3007-3010 (1998).
Soncin, et al., "Approaches to selectivity in the Zn(II)-phthalocyanine-photosensitized inactivation of wild-type and antibiotic-resistant *Staphylococcus aureus*", Photochem Photobiol Sci 1, 815-819 (2002).
Soukos, et al., "Targeted antimicrobial photochemotherapy", *Antimicrob. Agents Chemother.* 42: 2595-2601 (1998).
Stojilijkovic, "Antimicrobial properties of porphyrins", *Exp. Opin. Invest. Drugs* 10(2): 309-320 (2001).
Szpakowska, et al., "Susceptibility of Pseudomonas aeruginosa to a photodynamic effect of the arginine hematoporphyrin derivative", *Internet J Antimicrob Agents* 8, 23-27 (1997).
Tsutsui, "The usefulness of the porphyrin-viologen linked compounds as a photosensitizer for the photodynamic therapy (PDT)", *Chemical Abstracts* 119: 66705 (1992) (abstract only).
Tunger, et al., "Evaluation of rational antibiotic use," *Int. J. Microb. Agents* 15(2): 131-135 (2000).
Uehata, et al., "Magnetic field effects on the decay rates of photogenerated geminate racidal pairs in reversed micelles", *Chemical Abstracts* 111: 243931 (1989) (abstract only).
Usui, et al., "Effects of external magnetic fields on laser-induced electron-transfer reactions in porphyrin-viologen pairs at the surface of molecular bilayers", *Chemical Abstracts* 108: 204085 (abstract only).
Valduga, et al., "Effect of extracellularly generated singlet oxygen on gram-positive and gram-negative bacteria," *J. Photochem. Photobiol B.* 21: 81-86 (1993).
Valduga, et al., "Photosensitization of wild and mutant strains of *Escherichia coli* by meso-tetra (N-methyl-4-pyridyl)porphine," *Biochem. Biophys. Res. Commun.* 256: 84-88 (1999).
Wainwright, "Non-porphyrin photosensitizers in biomedicine", *Chemical Society Reviews* 351-359 (1996).
Wainwright, "Photodynamic antimicrobial chemotherapy (PACT)", *J. Antimicrob. Chemother.* 42: 13-28 (1998).
Wiehe, et al., "Hydrophilicity vs. hydrophobicity—varying the amphiphilic structure of porphyrins related to the photosensitizer mTHPC", *J. Porphyrins Phthalocyanines* 5: 758-761 (2001).
Yashunsky, et al., "Chemistry of dimeththylaminoporphyrins. 2. Porphyrin dimers linked by pyrrolylmethylene units" *Tetrahedron Lett.*, 38(1):105-108 (1997).
Yashunsky, et al., "Chemistry of *meso*-dimethylaminopropenyl-porphyrins and -bisporphyrins: the synthesis of australochlorin, a benzochlorin isomer", *Aust. J. Chem.*, 50:487-93 (1997).

Yeung, et al., "Facile synthesis and nonlinear optical properties of push-pull 5,15-diphenylporphyrins", *J. Org. Chem.*, 63:7143-50 (1998).

Zhang, et al., "Synthesis and antibacterial study of 10, 15, 20-triphenyl-5-{4-hydroxy-3-(trimethylammonium)methyl}phenylporphyrin as models for combination of porphyrin and alkylating agent" *Bioorganic and Medicinal Chemistry Letters* 13:1097-1100 (2003).

* cited by examiner

PORPHYRIN DERIVATIVES AND THEIR USE IN PHOTODYNAMIC THERAPY

This application is a divisional of copending application Ser. No. 10/744,863, filed Dec. 23, 2003, entitled "Porphyrin Derivatives and Their Uses in Photodyamic Therapy" by William Love, Derek Brundish, William Rhys-Williams, Xiang Dong Feng, and Benoit Pugin, which claims priority to British Patent Application No. 0229742.2, filed Dec. 23, 2002.

FIELD OF THE INVENTION

The present invention relates to compounds and uses thereof in the treatment of medical condition for which a photodynamic compound is indicated and, in particular, in the curative or prophylactic treatment of microbial colonisation and infection.

BACKGROUND OF THE INVENTION

The resistance to antibiotics developed by an increasing number of microorganisms is recognised to be a worldwide health problem (Tunger et al., 2000, *Int. J. Microb. Agents* 15:131-135, Jorgensen et al., 2000, *Clin. Infect. Dis.* 30:799-808). Thus, the development of non-antibiotic approaches for killing microorganisms is urgently required for controlling antibiotic-untreatable infections and limiting the development of additional antibiotic-resistant strains.

The treatment of microbial infections by photodynamic therapy (PDT) represents a valuable alternative method for eradicating bacteria since it involves a mechanism which is markedly different from that typical of most antibiotics. Thus, PDT is based on the use of a photosensitising molecule that, once activated by light, generates oxygen reactive species that are toxic for a large variety of prokaryotic and eukaryotic cells including bacteria, mycoplasmas and yeasts (Malik et al., 1990, *J. Photochem. Photobiol. B Biol.* 5:281-293; Bertoloni et al., 1992, *Microbios* 71:33-46). Importantly, the photosensitising activity of many photodynamic agents against bacteria is not impaired by the resistance to antibiotics but, instead, depends mainly on their chemical structure (Malik et al., 1992, *J. Photochem. Photobiol. B Biol.* 14:262-206).

Various types of neutral and anionic photosensitising agents exhibit a pronounced phototoxic activity against Gram positive bacteria. However, such photosensitising agents exert no appreciable cytotoxic activity against Gram negative bacteria unless the permeability of the outer membrane is altered by treatment with ethylene diamine tetra-acetic acid (EDTA) or polycations (Bertoloni et al., 1990, *FEMS Microbiol. Lett.* 71: 149-156; Nitzan et al., 1992, *Photochem. Photobiol.* 55:89-97). It is believed that the cellular envelope of Gram negative bacteria, which is more complex and thicker than that of Gram positive bacteria, prevents an efficient binding of the photosensitising agent or intercepts and deactivates the cytotoxic reactive species photogenerated by the photosensitising agent (Ehrenberg et al., 1985, *Photochem. Photobiol.* 41:429-435; Valduga et al., 1993, *J. Photochem. Photobiol. B. Biol.* 21:81-86).

In contrast, positively charged (cationic) photosensitising agents, including porphyrins and phthalocyanines, promote efficient inactivation of Gram negative bacteria without the need for modifying the natural structure of the cellular envelope (Merchat et al., 1996, *J. Photochem. Photobiol. B. Biol.* 32:153-157; Minnock et al., 1996, *J. Photochem. Photobiol. B. Biol.* 32:159-164). It appears that the positive charge favours the binding of the photosensitising agent at critical cellular sites that, once damaged by exposure to light, cause the loss of cell viability (Merchat et al., 1996, *J. Photochem. Photobiol. B. Biol.* 35:149-157). Thus, it has been reported that *Escherichia coli* is efficiently inactivated by visible light after incubation with the cationic 5,10,15,20-tetrakis-(4-N-methylpyridl-)-porphine ($T_4MPyP$) (Valduga et al., 1999, *Biochem. Biophys. Res. Commun.* 256:84-88). The phototoxic activity of this porphyrin is mainly mediated by the impairment of the enzymic and transport functions of both the outer and cytoplasmic membranes, rather than by binding to DNA.

However, the utility of known porphyrin-based photodynamic therapy agents is limited due to their toxicity against mammalian host tissue cells, i.e. the compounds are unable to differentiate between target microbial cells and host cells. In addition, the utility of known porphyrin-based photodynamic therapy agents if further limited by their relatively low potency for target microbial cells.

Hence, there is a need for porphyrin-based compounds with improved toxicity profiles and high potency, which can be used in PDT to preferentially kill microbial cells.

SUMMARY OF THE INVENTION

According to a first aspect of the invention, there is provided a compound of formula I

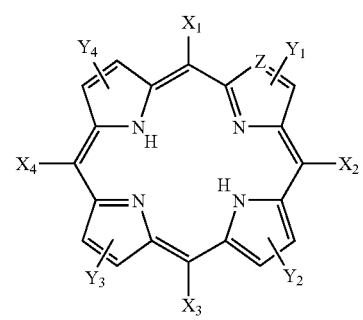

wherein:
$X_1$, $X_2$, $X_3$ and $X_4$ independently represent (i.e. are the same or different) a hydrogen atom, a lipophilic moiety, a phenyl group, a lower alkyl, alkaryl or aralkyl group, or a cationic group of the following formula;

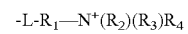

wherein:
L is a linking moiety or is absent;
$R_1$ represents lower alkylene, lower alkenylene or lower alkynylene, which is optionally substituted by one or more substituents selected from lower alkyl, lower alkylene (optionally interrupted with oxygen), fluoro, $OR_5$, $C(O)R_6$, $C(O)OR_7$, $C(O)NR_8R_9$, $NR_{10}R_{11}$ and $N^+R_{12}R_{13}R_{14}$; and
$R_2$, $R_3$ and $R_4$ independently represent (i.e. are the same or different) H, aryl, lower alkyl, lower alkenyl or lower alkynyl, the latter three of the which are optionally substituted by one or more substituents selected from lower alkyl, lower alkylene (optionally interrupted with oxygen), aryl, $OR_5$, $C(O)R_6$, $C(O)OR_7$, $C(O)NR_8R_9$, $NR_{10}R_{11}$ and $N^+R_{12}R_{13}R_{14}$
Z is —CH or N;
$Y_1$, $Y_2$, $Y_3$ and $Y_4$ are absent or independently represents aryl, lower alkyl, lower alkenyl or lower alkynyl, the latter three of which are optionally substituted by one or more substituents selected from lower alkyl, lower alkylene (optionally interrupted with oxygen), aryl, $OR_5$, $C(O)R_6$, $C(O)OR_7$, $C(O)NR_8R_9$, $NR_{10}R_{11}$ and $N^+R_{12}R_{13}R_{14}$; and $R_5$, $R_6$, $R_7$, $R_8$, $R_9$, $R_{10}$, $R_{11}$, $R_{12}$, $R_{13}$ and $R_{14}$ independently represent H or lower alkyl provided that at least one of $X_1$, $X_2$, $X_3$ and $X_4$ is a cationic group as defined above and at least one of $X_1$, $X_2$, $X_3$ and $X_4$ is a hydrogen atom, a phenyl group, a lipophilic moiety, or a lower alkyl, alkaryl or aralkyl group.

The term "lower alkyl" is intended to include linear or branched, cyclic or acyclic, $C_1$-$C_{20}$ alkyl which may be interrupted by oxygen (preferably no more than five oxygen atoms are present in each alkyl chain). Lower alkyl groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_{1\text{-}18}$ alkyl, $C_1$-$C_{16}$ alkyl, $C_1$-$C_{14}$ alkyl, $C_1$-$C_{12}$ alkyl, $C_{1\text{-}10}$ alkyl, $C_{1\text{-}9}$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl and $C_1$-$C_2$ alkyl. Preferred lower alkyl groups which $R_1$, $R_2$, $R_3$, $R_4$, $R_5$, $R_6$, $R_7$, $R_8$, $R_9$, $R_{10}$ and $R_{11}$ may represent include $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$ and $C_{16}$ alkyl.

Thus, any one or more $R_1$ to $R_{11}$ (or of $X_1$ to $X_4$) may represent cyclic amine/ammonium groups, for example:

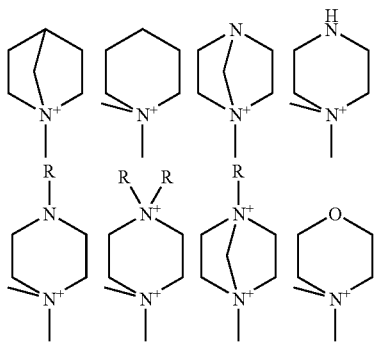

It will be appreciated that the cyclic amine/ammonium groups may also comprise fewer or greater than six members, for example such groups may comprise 4-, 5-, 7-, 8-, 9- or 10-membered rings.

The term "lower alkylene" is to be construed accordingly.

The terms "lower alkenyl" and "lower alkynyl" are intended to include linear or branched, cyclic or acyclic, $C_2$-$C_{20}$ alkenyl and alkynyl, respectively, each of which may be interrupted by oxygen (preferably no more than five oxygen atoms are present in each alkenyl or alkynyl chain).

The term "lower alkenyl" also includes both the cis and trans geometric isomers. Lower alkenyl groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_2$-$C_{18}$ alkenyl, $C_2$-$C_{17}$ alkenyl, $C_2$-$C_{16}$ alkenyl, $C_2$-$C_{14}$ alkenyl, $C_2$-$C_{12}$ alkenyl, $C_2$-$C_{10}$ alkenyl, $C_2$-$C_8$ alkenyl, $C_2$-$C_7$ alkenyl, $C_2$-$C_6$ alkenyl, $C_2$-$C_5$ alkenyl, $C_2$-$C_4$ alkenyl, $C_2$-$C_3$ alkenyl and $C_3$-$C_4$ alkenyl. Preferred lower alkenyl groups which $R_1$, $R_2$, $R_3$, $R_4$, $R_5$, $R_6$, $R_7$, $R_8$, $R_9$, $R_{10}$ and $R_{11}$ may represent include $C_2$, $C_3$, $C_4$, $C_5$, $C_6$, $C_7$, $C_8$, $C_9$, $C_{10}$, $C_{11}$, $C_{12}$, $C_{13}$ and $C_{14}$ alkenyl.

The term "lower alkenylene" is to be construed accordingly.

"Lower alkynyl" groups which $R_1$, $R_2$, $R_3$, $R_4$, $R_5$, $R_6$, $R_7$, $R_8$, $R_9$, $R_{10}$, $R_{11}$, $R_{12}$, $R_{13}$ and $R_{14}$ may represent include $C_2$-$C_{18}$ alkynyl, $C_2$-$C_{16}$ alkynyl, $C_2$-$C_{14}$ alkynyl, $C_2$-$C_{12}$ alkynyl, $C_2$-$C_{10}$ alkynyl, $C_2$-$C_9$ alkynyl, $C_2$-$C_8$ alkynyl, $C_2$-$C_7$ alkynyl, $C_2$-$C_6$ alkynyl, $C_2$-$C_5$ alkynyl, $C_2$-$C_4$ alkynyl, $C_2$-$C_3$ alkynyl and $C_3$-$C_4$ alkynyl Preferred lower alkynyl groups which $R_1$, $R_2$, $R_3$, $R_4$, $R_5$, $R_6$, $R_7$, $R_8$, $R_9$, $R_{10}$ and $R_{11}$ may represent include $C_2$, $C_3$, $C_4$, $C_5$, $C_6$, $C_7$, $C_8$, $C_9$, $C_{10}$, $C_{11}$, $C_{12}$, $C_{13}$ and $C_{14}$ alkynyl.

The term "lower alkynylene" is to be construed accordingly.

The term "aryl" includes six to ten-membered carbocyclic aromatic groups, such as phenyl and naphthyl, which groups are optionally substituted by one or more substituents selected from fluoro, cyano, nitro, lower alkyl (i.e. alkaryl), $OR_5$, $C(O)R_6$, $C(O)OR_7$, $C(O)NR_8R_9$ and $NR_{10}R_{11}$.

The term "aralkyl" includes aryl groups joined to the porphyrin ring via a lower alkyl group.

A second aspect of the invention provides a compound of formula II:

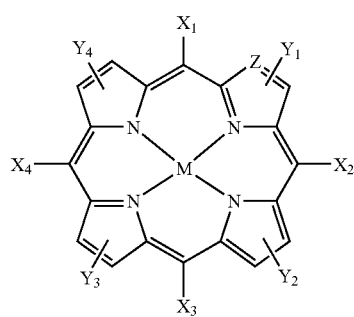

II wherein M is a metallic element or a metalloid element and $X_1$, $X_2$, $X_3$, $X_4$, $Y_1$, $Y_2$, $Y_3$, $Y_4$ and Z are as defined above.

The term "metallic element" is intended to include a divalent or trivalent metallic element. Preferably, the metallic element is diamagnetic. More preferably, the metallic element is selected for Zn (II), Cu (II), La (III), Lu (III), Y (III), In (III), Cd (II), Mg (II), Al(III), Ru, Ni(II), Mn(III), Fe(III), and Pd(II). Most preferably, the metallic element is Ni(II), Mn(III), Fe(III) or Pd(III).

The term "metalloid" is intended to include an element having physical and chemical properties, such as the ability to conduct electricity, that are intermediate to those of both metals and non-metals. The term metalloid element includes silicon (Si) and germanium (Ge) atoms which are optionally substituted with one or more ligands.

It will be appreciated that the terms metallic element and metalloid element include a metal element or a metalloid element having a positive oxidation state, all of which may be substituted by one or more ligands selected from fluoro, OH, $OR_{15}$ wherein $R_{15}$ is lower alkyl, lower alkenyl, lower alkynyl, aralkyl, aryl or alkaryl as defined above (wherein aryl and alkaryl are mono-substituted.

The compounds of formulae I and II comprise at least one cationic group. Thus, the compounds of the invention may carry a net positive charge, for example a chare of +1, +2, +3, +4, +5, +6 or more. In a preferred embodiment, the compounds carry a net charge of less than +4, for example +1, +2 or +3. In a particularly preferred embodiment, the compounds carry a net charge of +2.

It will appreciated by persons skilled in the art that compounds of formulae I and II may be counterbalanced by counter-anions. exemplary counter-anions include, but are not limited to, halides (e.g. fluoride, chloride and bromide), sulfates (e.g. decylsulfate), nitrates, perchlorates, sulfonates (e.g. methane sulfonate) and trifluoroacetate. Other suitable counter-anions will be well known to persons skilled in the art. Thus, pharmaceutically, and/or veterinarily, acceptable derivatives of the compounds of formulae I and II, such as salts and solvates, are also included within the scope of the invention. Salts which may be mentioned include: acid addition salts, for example, salts formed with inorganic acids such as hydrochloric, hydrobromic, sulfuric and phosphoric acid, with carboxylic acids or with organo-sulfonic acids; base addition salts; metal salts formed with bases, for example, the sodium and potassium salts.

It will be further appreciated by skilled persons that the compounds of formula I may exhibit tautomerism. All tautomeric forms and mixtures thereof are included within the scope of the invention.

Compounds of formulae I and II may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compound using conventional, e.g. fractional crystallisation or HPLC, techniques. Alternatively, the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

In a preferred embodiment of the compounds of the first and second aspects of the invention, Z is —CH.

A characterisation feature of the compounds of the first and second aspects of the invention is that at least one of substituent groups $X_1$, $X_2$, $X_3$ and $X_4$ is a quaternary ammonium cationic group of the formula -L-$R_1$ —$N^+(R_2)(R_3)R_4$, as defined above. Preferably, none of $X_1$, $X_2$, $X_3$ and $X_4$ is an anilinium or a pyridinium cationic group.

In a preferred embodiment, $R_1$ is an unsubstituted lower alkylene, lower alkenylene or lower alkynylene group.

Advantageously, $R_1$ is a straight-chain lower alkylene group of formula:

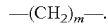

—$(CH_2)_m$—.

Preferably, 'm' is an integer between 1 and 20. More preferably, 'm' is an integer between 1 and 10, for example between 1 and 6, between 1 and 5, between 1 and 4 or between 1 and 3. Preferred straight-chain lower alkylene groups with $R_1$ may represent include groups of the above formula wherein m is 2, 3, 4, 5, 6, 7, 8, 9 or 10. Most preferably, 'm' is 2 or 3.

The remaining three substituent groups of the quaternary ammonium moiety, i.e. $R_2$, $R_3$ and $R_4$, may be the same or different and are selected from H, lower alkyl, lower alkenyl or lower alkynyl, the latter three of which are optionally substituted by one or more substituents selected from lower alkyl, $OR_5$, $C(O)R_6$, $C(O)OR_7$, $C(O)NR_8$ $R_9$, $NR_{10}R_{11}$ and $N^+R_{12}R_{13}R_{14}$.

In a preferred embodiment $R_2$, $R_3$ and/or $R_4$ are lower alkyl, lower alkenyl or lower alkynyl group.

Preferably, $R_2$, $R_3$ and/or $R_4$ are unsubstituted lower alkyl groups.

Optionally, at least one of $R_2$, $R_3$ and $R_4$ is an alkyl group which is substituted with a primary, secondary or tertiary amine group or a quaternary ammonium group.

In a preferred embodiment of the compounds of the first and second aspects of the invention, $R_1$ is —$(CH_2)_3$—, $R_2$ and $R_3$ are $CH_3$ and $R_4$ is —$(CH_2)_3$—$N(CH_3)_2$.

In an alternative preferred embodiment of the compounds of the first and second aspects of the invention $R_1$ is —$(CH_2)_3$—, and $R_2$, $R_3$ and $R_4$ are each $CH_3$.

In a further alternative preferred embodiment of the compounds of the first and second aspects of the invention, $R_1$ is —$(CH_2)_3$—, and $R_2$, $R_3$ and $R_4$ are each $C_2H_5$.

Advantageously, at least one of $X_1$, $X_2$, $X_3$ and $X_4$ is a cationic group as defined above and at least one of $X_1$, $X_2$, $X_3$ and $X_4$ is a hydrogen atom.

Preferable, each of $X_1$, $X_2$, $X_3$ and $X_4$ is a hydrogen atom or a cationic group as defined above.

Conveniently, the pK values of any primary, secondary or tertiary amine groups, if present in the compounds of the invention, is greater than 8 to ensure that the group is protonated when in a physiological environment.

The quaternary ammonium cationic group is optionally joined to the porphyrin ring via a linking moiety, L.

Preferred linking moieties, L, include phenoxy, phenylene, sulfonyl amido aminosulfonyl, sulfonylimino, phenylsulfonylamide, phenylaminosulfonyl, urea, urethane and carbamate linking moieties.

In a preferred embodiment, the quaternary ammonium cationic group is joined to the porphyrin ring via phenoxy linker.

Thus, $X_1$, $X_2$, $X_3$ and $X_4$ may have the following formula:

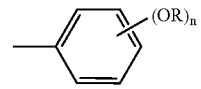

wherein R is $R_1$—$N^+(R_2)(R_3)R_4$, as defined above, and 'n' is an integer between 1 and 3.

In an alternative preferred embodiment, the quaternary ammonium cationic group is joined to the porphyrin ring via a phenylene linker.

Thus, $X_1$, $X_2$, $X_3$ and/or $X_4$ may have the following formula:

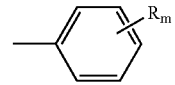

wherein R is $R_1$—$N^+(R_2)(R_3)R_4$, as defined above, and 'm' is an integer between 1 and 3.

Preferably, 'm' is 2, and most preferably 1.

In an alternative preferred embodiment, $X_1$, $X_2$, $X_3$ and/or $X_4$ may have the following formula:

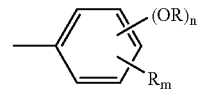

wherein R is $R_1$—$N^+(R_2)(R_3)R_4$, 'n' and 'm' are as defined above, and 'n+m' is between 1 and 3.

Advantageously, L comprises a benzene ring (e.g. phenoxy, phenylene, phenylsulfonylamido or phenylamino-sulfonyl mono-substituted at meta- or ortho-positions. L may also be both para- and ortho-substituted.

In an alternative preferred embodiment, the quaternary ammonium cationic group is joined directly to the porphyrin ring i.e. L is absent.

In a preferred embodiment of the first and second aspects of the invention, the compound comprises two cationic groups, as defined above, on opposite sides of the porphyrin ring, i.e.

at ring positions 5 and 15 or ring positions 10 and 20. For example, $X_1$ and $X_3$ may be a hydrogen atom, a lipophilic moiety, a phenyl group, a lower alkyl, alkaryl or aralkyl group, and $X_2$ and $X_4$ may be cationic groups, or vice versa. Preferably, $X_1$ and $X_3$ are both a hydrogen atom and $X_2$ and $X_4$ are both a cationic group, or vice versa.

Alternatively, the compound of the invention may comprise two cationic groups, as defined above, on neighbouring positions of the porphyrin ring, i.e. at ring positions 5 and 10, or ring positions 10 and 15, or ring positions 15 and 20 or ring positions 20 and 5. For example $X_1$ and $X_2$ may be hydrogen and $X_3$ and $X_4$ may be cationic groups, or $X_2$ and $X_3$ may be hydrogen and $X_4$ and $X_1$ may be cationic groups, etc.

It will be appreciated by persons skilled in the art that additional isomeric structural possibilities arise when Z represents nitrogen. Such possibilities are included within the scope of the present invention.

In a further preferred embodiment of the compounds of the first and second aspects if the invention, the compound is substituted on one or more of its constituent pyrrole rings. Thus, $Y_1$, $Y_2$, $Y_3$ and $Y_4$ may be absent or independently represent aryl, lower alkyl, lower alkenyl or lower alkynyl, the latter three of which are optionally substituted by one or more substituents selected from lower alkyl, lower alkylene (optionally interrupted with oxygen), aryl, $OR_5$, $C(O)R_6$, $C(O)OR_7$, $C(O)NR_8 R_9$, $NR_{10}R_{11}$ and $N^+R_{12}R_{13}R_{14}$. It will be appreciated by skilled persons that $Y_1, Y_2, Y_3$ and/or $Y_4$ may comprise cyclic groups, which may be saturated or aromatic. For example, one or more of the pyrrole rings may be substituted to form an iso-indole group, i.e. $Y_1$, $Y_2$, $Y_3$ and/or $Y_4$ together with the pyrrole ring to which they are attached may be cyclic.

In an alternative preferred embodiment of the compounds of the first and second aspects of the invention, $Y_1$, $Y_2$, $Y_3$ and/or $Y_4$ are absent. Thus, the porphyrin ring is preferably substituted only at one or more of positions 5, 10, 15 or 20.

In a further preferred embodiment of the compounds of the first and second aspects of the invention, at least one of $Y_1, Y_2, Y_3$ and/or $Y_4$ is or comprises a lipophilic moiety.

By 'lipophilic moiety' we include moieties having a partition coefficient between 1-n-octanol and water expressed as log P of greater than 1.0 at physiological pH and 25° C.

Conveniently, the lipophilic moiety is a saturated, straight-chain alkyl group of formula —$(CH_2)_pCH_3$, or an equivalent alkylene group of formula —$(CH_2)_p$—, wherein 'p' is an integer between 1 and 22, for example between 1 and 18. Preferably, 'p' is between 1 and 18, more preferably between 2 and 16, between 4 and 16, between 6 and 18, between 8 and 16 or between 4 and 12. Most preferably, 'p' is between 10 and 12.

It will be appreciated that $X_1$, $X_2$, $X_3$ and/or $X_4$ may be a cationic group, as defined above, which also comprises a lipophilic moiety.

In an alternative preferred embodiment of the first and second aspects of the invention, none of $X_1$, $X_2$, $X_3$ and $X_4$ is a lipophilic moiety.

Advantageously, the compounds of the invention are soluble in water. Preferably, the compounds may be dissolved in water to a concentration of at least 5 µg/l, for example at least 10 µg/l, 15 µg/l or 20 µg/l. More preferably, the compounds may be dissolved in water to concentration of at least 100 µg/l, for example 200 µg/l, 300 µg/l, 400 µg/l, 500 µg/l, 1 mg/ml, 5 mg/ml, 10 mg/ml, 20 mg/ml, 50 mg/ml or 100 mg/ml.

Conveniently, the compounds of the invention exhibit greater toxicity to a larger microorganism (e.g. a bacterium) upon illumination/irradiation than in the absence of activating illumination/irradiation, i.e. they exhibit greater photodynamic activity ('light toxicity') than dark toxicity (see below). It will be appreciated that such toxicity may be determined using cell cultures. Preferably, the photodynamic activity of a compound is a least tow-fold greater than the dark toxicity of that compound, more preferably at least three-fold, at least four-fold, at least five-fold, at least six-fold, at least eight-fold, at least ten-fold, at least fifteen-fold or at least twenty fold. Most preferably, the compound of the invention is substantially non-toxic in the absence of illumination/irradiation.

In a preferred embodiment, the compound of the invention is toxic to the target microorganism (e.g. bacterial cells) at low doses. Preferably, the compound is toxic to the target microorganism at a concentration of less than 10 µM, for example less than 1 µM, less than 0.1 µM, less than 0.01 µM, less than 0.05 µM or less than 0.001 µM (see Example B).

Preferred compounds of the invention include the following:

(a) 5,15-bis-(4-{3-[(3-Dimethylamino-propyl)-dimethyl-ammonio]-propyloxy}-phenyl)-porphyrin dichloride ("Compound 8")

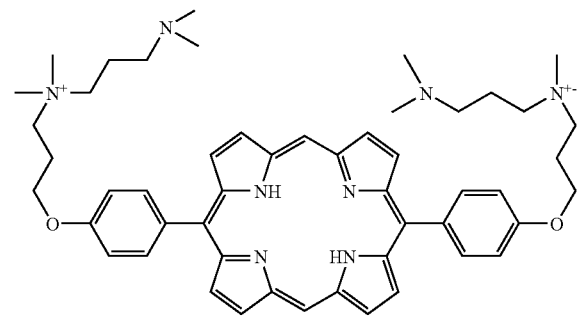

Preferably, this compound is provided as a dichloride of tetrachloride salt.

(b) 5,15-bis-[4-(3-Triethylammonio-propyloxy)-phenyl]-porphyrin dichloride ("Compound 9");

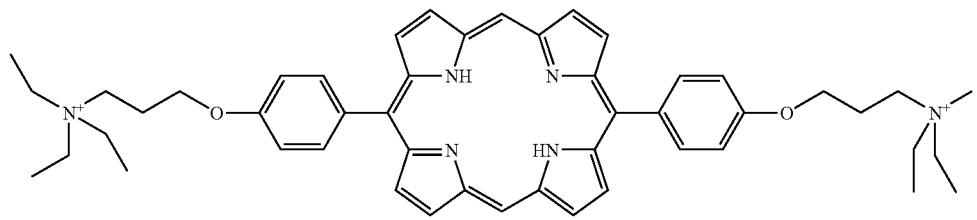

Preferably, this compound is provided as a dichloride salt.
(c)  5,15-bis-[3-(3-Trimethylammonio-propyloxy)-phenyl]-porphyrin dichloride ("Compound 12");

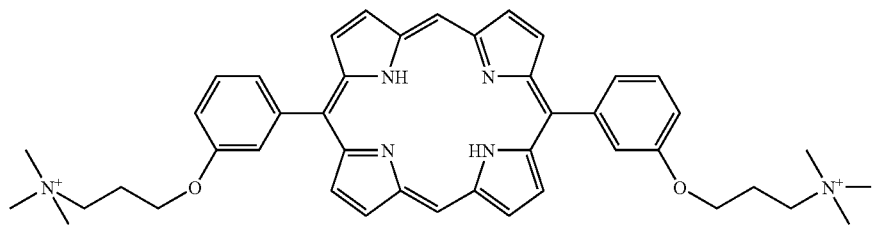

Preferably, this compound is provided as a dichloride salt.
(d)  5,15-bis-[4-(3-Trimethylammonio-propyloxy)-phenyl]-porphyrin dichloride ("Compound 10");

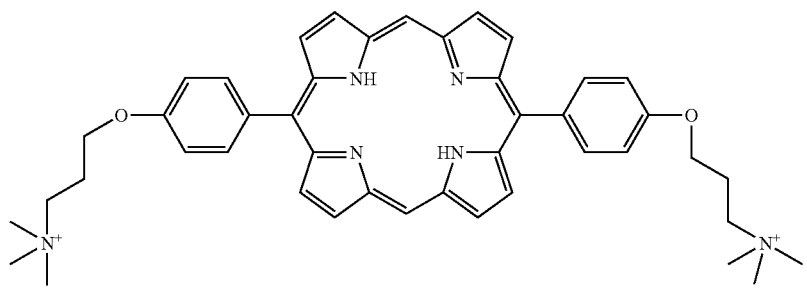

Preferably, this compound is provided as a dichloride salt.
(e)  5-[3,5-bis-(3-/Trimethylammonio-propyloxy)-phenyl]-15-undecyl-porphyrin dichloride ("Compound 6");

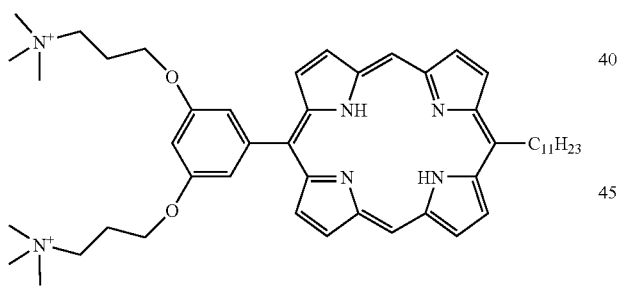

Preferably, this compound is provided as a dichloride salt.
(f)  5-{4-[3-Dimethyl-(3-dimethylaminopropyl)-ammonio-propyloxy]phenyl}-15-(4dodecyloxy-phenyl)-porphyrin chloride (Compound "23");

Preferably, this compound is provided as a chloride or dichloride salt.
(g) 3-[({3-[3-{4[15-(4-Dodecyloxy-phenyl)-porphyrin-5yl]-phenoxy}-propyl)-dimethyl-ammonio]-propyl}-dimethyl-ammonio)-propyl]-trimethyl-ammonium trichloride ("Compound 25");

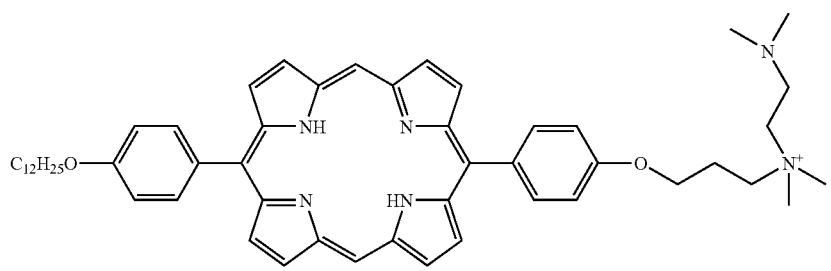

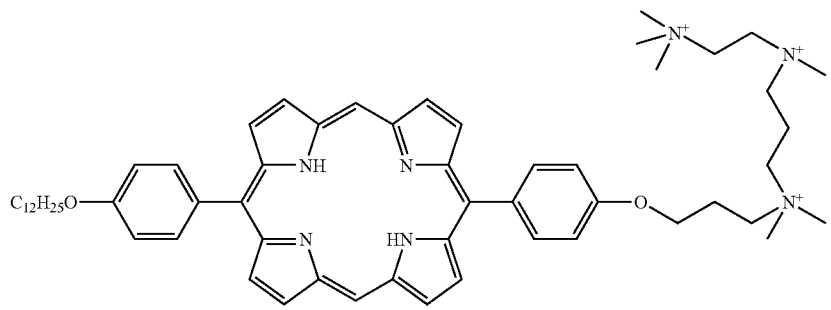

Preferably, this compound is provided as a trichloride salt.

(h) 5,15-bis-[3-(3-Trimethylammmonio-propyloxy)-phenyl]-10-undecyl-porphyrin dichloride ("Compound 28");

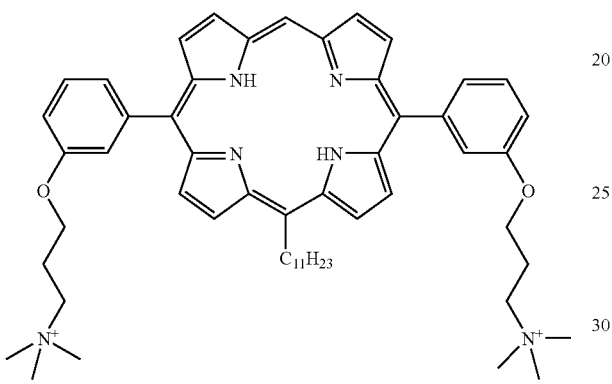

Preferably, this compound is provided as a dichloride salt.

(i) 5-{4-[3-Dimethyl-(3-trimethylammonio-propyl)-ammonio-propyloxy]-phenyl}-15-(4-dodecyloxy-phenyl)-porphyrin dichloride ("Compound 31"); and

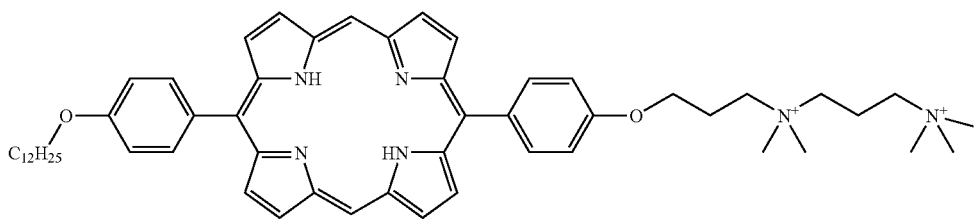

Preferably, this compound is provided as a dichloride salt.

(j) 5-[4(3-Dimethyldecyl-ammoniopropyloxy)-phenyl]-15-{4-[3-dimethyl-(3-dimethylaminopropyl)-ammoniopropyloxy]-phenyl}-porphyrin dichloride ("Compound 32").

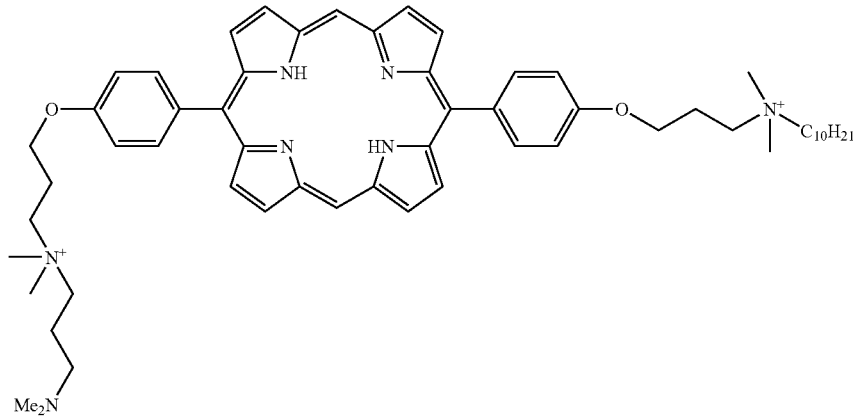

Preferably, this compound is provided as a dichloride salt.

It will be appreciated that the above compounds may alternatively be in a metallated form, i.e. they may comprise a chelated metallic element or metalloid element within the porphyrin ring.

A third aspect of the invention provides a compound for use as a selective photodynamic therapy agent, i.e. for selectively killing microorganisms, wherein the compound is a compound according to the first or second aspect of the invention.

By 'selective' we mean the photodynamic therapy agent is preferentially toxic to one or more microorganisms (such as bacteria, mycoplasmas, yeasts, fungi and/or viruses) compared to mammalian e.g. human, host cells. Preferably, the toxicity of the compound to a target microorganism is at least two-fold greater than the toxicity of that compound to mammalian cells (such as human skin cells), more preferably at least three-fold, at least four-fold, at least five-fold, at least six-fold, at least eight-fold, at least ten-fold, at least fifteen-fold or at least twenty fold. Most preferably, the compound of the invention is substantially non-toxic to mammalian cells.

In this way, when the compounds of the invention are used to treat bacterial infections, for example, dosing regimes can be selected such that bacterial cells are destroyed with minimal damage to healthy host tissue (e.g. skin cells). Thus, the photodynamic therapy agents preferably exhibit a 'therapeutic window'.

A fourth aspect of the invention provides a pharmaceutical formulation comprising a compound according to the first or second aspect of the invention in admixture with a pharmaceutically or veterinarily acceptable adjuvant, diluent or carrier.

The compounds of the invention can be formulated at various concentrations, depending on the efficacy/toxicity of the compound being used and the indication for which it is being used. Preferably, the formulation comprises the compound of the invention at a concentration of between 0.1 µM and 1 mM, more preferably between 1 µM and 100 µM, between 5 µM and 50 µM, between 10 µM and 50 µM, between 20 µM and 40 µM and most preferably about 30 µM. For in vitro applications, formulations may comprise a lower concentration of a compound of the invention, for example between 0.0025 µM and 1 µM.

It will be appreciated by persons skilled in the art that the compounds of the invention will generally be administered in admixture with a suitable pharmaceutical excipient diluent or carrier selected with regard to the intended route of administration and standard pharmaceutical practice (for example, see *Remington: The Science and Practice of Pharmacy*, 19$^{th}$ edition, 1995, ed. Alfonso Gennaro, Mack Publishing Company, Pennsylvania, USA).

For example, for application topically, e.g. to the skin or a wound site, the compounds of the invention can be administered in the form of a lotion, solution, cream, gel, ointment or dusting powder (for example, see Remington, supra, pages 1586 to 1597). Thus, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxpropylene compound, emulsifying was and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, e-lauryl sulphate, an alcohol (e.g. ethanol, cetearyl alcohol, 2-octyldodecanol, benzyl alcohol) and water.

In a preferred embodiment, the formulation (e.g. lotion, solution, cream, gel or ointment) is water-based.

Formulations suitable for topical administration in the mouth further include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

The compounds of the invention can also be administered intranasally of by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A$^3$ or 1,1,1,2,3,3,3-heptafluoropropane (HFA 227A$^3$), carbon dioxide or other suitable gas. In the case of a pressurised aerosol, the dosage unit may be determined by providing a valve to deliver a metered amount. The pressurised container, pump, spray or nebuliser may contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains at least 1 mg of a compound of the invention for delivery to the patient. It will be appreciated that he overall dose with an aerosol will vary from patient to patient and from indication to indication, and may be administered in a single dose or, more usually, in divided doses throughout the day.

Alternatively, other conventional administration routes known in the art may also be employed; for example the compounds of the invention may be delivered orally, buccally or sublingually in the form of tablets, capsules, ovules, elixirs, solutions or suspensions, which may contain flavouring or colouring agents, for immediate-, delayed- or controlled-release applications. The compounds of invention may also be administered intra-ocularly (see below), intra-aurally or via intracavernosal injection.

The compounds of the invention can also be administered parenterally, for example, intravenously, intra-arterially, intraperitoneally, intrathecally, intraventricularly, intrasternally, intraeranially, intra-muscularly or subcutaneously (including via an array of fine needles or using needle-free Powderject® technology), or they may be administered by infusion techniques. They are best used in the form of a sterile aqueous solution which may contain other substances, for example, enough salts or glucose to make the solution isotonic with blood. The aqueous solutions should be suitable buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain ant-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

The compounds of the invention may also be administered by the ocular route, particularly for treating diseases of the eye. For ophthalmic use, the compounds of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For veterinary use, a compound of the invention is administered as a suitably acceptable formulation in accordance with normal veterinary practice and the veterinary surgeon will determine the dosing regimen and route of administration which will be most appropriate for a particular animal.

The compounds and/or formulations of the invention may be stored in any suitable container or vessel known in the art. It will be appreciated by persons skilled in the art that the container or vessel should preferably be airtight and/or sterilised. Advantageously, the container or vessel is made of a plastics material, such as polyethylene.

A fifth aspect of the invention provides a compound according to the first or second aspects of the invention for use in medicine and, in particular, in the curative and/or prophylactic treatment of microbial infections.

The compounds of the invention are photosensitive (photodynamic) as they emit reactive oxygen species, such as singlet oxygen or oxygen free radicals, following illumination/irradiation in the presence of oxygen with light of an appropriate wavelength (typically 400 nm to 800 nm, see below). Consequently, the compounds of the invention are suitable for use as photodynamic therapy agents in the curative and/or prophylactic treatment of a medical condition for which a photodynamic agent is indicated (for example, see Smith, 2002, *Curr Probl Cancer.* 26(2):67-108; Hopper, 2000, *Lancet Oncol.* 1:212-9; Dougherty, 2002, *J Clin Laser Med Surg.* 20(1):3-7; Ceburkow & Gollnick, 2000, *Eur J Dermatol.* 10(7):568-75).

Preferably, the compounds of the invention are for use in the curative and/or prophylactic treatment of bacterial infections such as Gram positive cocci (e.g. *Streptococcus*), Gram negative cocci (e.g. *Neisseria*), Gram positive bacilli (e.g. *Corynebacterium* species), Gram negative bacilli (e.g. *Escherichia coli*), acid-fast bacilli (e.g. a typical *Mycobacterium*) and including infections causing abscesses, cysts, dermatological infections, wound infections, arthritis, urinary tract infections, pancreatitis, pelvic inflammatory disease, peritonitis, prostatitis, infections of the vagina, oral cavity (including dental infections), eye and/or ear, ulcers and other localised infections; actinomyces infections; fungal infections such as *Candida albicans*, *Aspergillus* and *Blastomyces*; viral infections such as HIV, encephalitis, gastro-enteritis, haemorrhagic fever, hantavirus, viral hepatitis, herpes virus (e.g. cytomegalovirus, Epstein-Barr, herpesvirus simiae, herpes simplex and varicella-zoster); protozoal infections such as amoebiasis, babesiosis, coccidiosis, cryptosporidiosis, giardiasis, Leishmaniasis, Trichomoniasis, toxoplasmosis and malaria; helminthic infections such as caused by nematodes, cestodes and trematodes, e.g. ascariasis, hook worm, lymphatic filariasis, onchocerciasis, schistosomiasis and toxocariasis; and inflammatory diseases such as soft-tissue rhematism, osteoarthritis, rheumatoid arthritis and spondyloarthropathies.

More preferably, the compounds of the invention are for use in the curative and/or prophylactic treatment of infections by Gram positive bacteria and/or Gram negative bacteria. Most preferably, the compounds of the invention are for use in the curative and/or prophylactic treatment of infections by Gram positive bacteria.

The compounds of the invention are preferably used to kill microorganisms, e.g. bacteria, mycoplasmas, yeasts, fungi and viruses. The compounds of the invention are particularly suitable for killing bacteria which have developed resistance to conventional antibiotic treatments, such as methicillin-resistant *Staphylococcus aureus* (MRSA).

It will be appreciated by persons skilled in the art that the compounds of the invention are suitable to treat all infections where target microorganisms can be found on a light-accessible surface or in a light accessible area (e.g. epidermis, oral cavity, nasal cavity, sinuses, ears, eyes, lungs, uro-genital tract, and gastrointestinal tract). In addition, the compounds of the invention are suitable to treat infections on surfaces or areas which are made accessible to light transiently, such as infected bones temporarily exposed during surgical procedures. Infections of the peritoneal cavity, such as those resulting from burst appendicitis are light-accessible via at least laparoscopic devices.

Dosage of the compounds of the invention will depend on several factors; including the particular compounds used, the formulation, route of administration and the indication for which the compound is used. Typically, however, dosages will range from 0.01 to 20 mg of compound per kilogram of body weight, preferably from 0.1 to 15 mg/kg, for example from 1 to 10 mg/kg of body weight.

In a preferred embodiment, the compounds of the invention are used in combination with conventional antimicrobial agents. For example, the compounds may be used in combination with one or more of the following conventional antibiotics; anti-bacterial agents, for example natural and synthetic penicillins and cephalosporins, sulphonanides, crythromycin, kanomycin, tetracycline, chloramphenicol, rifampicin and including gentamicin, ampicillin, benzypenicillin, benethamine penicillin, benzathine penicillin, phenethicillin, phenoxy-methyl penicillin, procaine penicillin, cloxacillin, flucloxacillin, methicillin sodium, amoxicillin, bacampicillin hydrochloride, ciclacillin, mazlocillin, pivampicillin, talampicillin hydrochloride, carfecillin sodium, peperacillin, ticarcillin, mecillinam, pirmecillinan, cefaclor, cefadroxil, cefotaxime, cefoxitin, cefsulodin sodium, ceftazidime, ceftizoxime, cefuroxime, cephalexin, cephalothin, cephamandole, cephazolin, cephradine, latamoxef disodium, aztreonam, chlortetracycline hydrochloride, clomocycline sodium, demeclocydine hydrochloride, doxycycline, lyme-cycline, minocycline, oxytetracycline, amikacin, framycetin sulphate, neomycin sulphate, netilmicin, tobramycin, colistin, sodium fusidate, polymyxin B sulphate, spectinomycin, vancomycin, calcium suphaloxate, sulfametopyraxine suphadiazine, sulphadimidine, sulphaguanidine, suphaurea, capreomycin, metronidazole, tinidazole, cinoxacin, ciprofloxacin, nitrofurantoin, hexamine, streptomycin, carbenicillin, colistimethate, polymyxin B, furazolidone, nalidixic acid, trimethoprim-sulfamethoxazole, clindamycin, lincomycin, cycloserine, isoniazid, ethambutol, ethionamide, pyrazinamide and the like; anti-fungal agents, for example miconazole, ketoconazole, itraconazole, fluconazole, amphotericin, flucytosine, griseofulvin, natamycin, nystatin, and the like; and anti-viral agents such as acyclovir, AZT, ddI, amantadine hydrochloride, inosine pranobex, vidarabine, and the like.

In a further preferred embodiment, the compounds of the invention are co-administered with penetration enhancing agents, such as poly-(ethyleneimine), or antibiotic agents which exhibit such penetration-enhancing capability (e.g. polymyxin or colistin).

The compounds of the invention are particularly suited for use in the curative or prophylactic treatment of one or more of the following indications:

Impetigo

Impetigo is a highly communicable infection. It is the most common infection in children.

Impetigo have two classic forms nonbullous and bullous. The nonbullous impetigo, also named impetigo contagiosa accounts for approximately 70% of cases. Lesions normally resolve in 2 to 3 weeks without treatment. Impetigo also may complicate other skin diseases such as scabies, varicella, atopic dermatitis, and Darier's disease.

(a) Nonbullous Impetigo

Type of Bacteria

Nonbullous is an infection caused principally by Group A beta-haemolytic streptococci (*Streptococcus pyogenes*), *Staphylococcus aureus*, or a combination of these two organisms (see Andrews' diseases of the skin: clinical dermatology 9th ed. (2000) edited by Odom R B editor Saunders p. 312-4). Non-Group A (Group B, C, and G) streptococci may be responsible for rare cases of impetigo, and Group B streptococci are associated with impetigo in the newborn.

Type of Wounds

Nonbullous is a superficial, intraepidermal unilocular vesiculopustular infection.

Lesions of non bullous impetigo commonly begin on the skin of the face or extremities following trauma. As a rule, intact skin is resistant to impetiginazation.

The clinical presentation of impetigo evolves in an orderly fashion from a small vesicle or pustule, which progresses into honey-coloured crusted plaque. Lesions usually are less than 2 cm in diameter. Lesions tend to dry, leaving fine crusts without cicatrisation. Lesions are usually minimally symptomatic. Rarely, erythema associated with mild pain or slight pruritus may be present. The infection spreads to contiguous and distal areas through the inoculation of other wound from scratching.

Site of Bacteria

Nonbullouos impetigo is a superficial streptococcal or staphylococcal infection which is localised to the subcorneal (just beneath the stratum corneum) layer of the skin (see FIG. 1). More particularly, infection in impetigo is confined histopathogically to highly differentiated, upper epidermal keratinocytes. Once the bacteria invade a break in the skin, they begin to multiply.

The histopathology is that of an extremely superficial inflammation about the funnel-shaped upper portion of the pilosebaceous follicles. A subcorneal vesicopustule is formed, containing a few scattered cocci, together with debris of polymorphonuclear leukocytes and epidermal cells. In the dermis, there is a mild inflammatory reaction—vascular dilation, oedema, and infiltration of polymorphonuclear leukocyts (Andrews' diseases of the skin, supra., p. 312-4).

(b) Bullous Impetigo

Type of Bacteria

Bullous impetigo is caused primarily by strains of *Staphylococcus aureus* which produce exfoliative toxins (Sadick et al., 1997, *Dermatologic Clinics* 15(2): 341-9).

Type of Wounds

Bullous impetigo is histologically characterised by subcorneal cleavage and infiltrate with polymorphonuclear leucocytes migrating through the epidermis and accumulating between granular and stratum corneum skin layers. Small or large superficial fragile bullae are present on the trunk and extremities.

Flaccid bullae and moist erosions with surrounding erythema are characteristic of this subcorneal infections. Often, only the remnants of ruptured bullae are seen at the time of presentation. The separation of the epidermis is due to an exotoxin produced by *Staphylococcus aureus*.

Sites of Bacteria

Bullous impetigo is a superficial staphylococcal infection that occurs in and just beneath the stratum corneum (see FIG. 1). Bullous impetigo is considered due to exfoliative toxin produced by some *Staphylococcus aureus* attached to stratum corneum cells.

Atopic Dermatitis (AD)

Atopic dermatitis, also named atopic eczema, is a chronic inflammation of the skin resulting in an itchy rash, especially in the flexures i.e. behind the knees, in front of the elbows, wrists, neck, and eyelids. Infection of the rash is common, and causes further inflammation and itch.

Eczema typically manifests in those aged 1-6 months. Approximately 60% of patients have their first outbreak by 1 year and 90% by 5 years. Onset of atopic dermatitis in adolescence or later is uncommon and should prompt consideration of another diagnosis. Disease manifestations vary with age.

Type of Bacteria

Bacteria and their superantigens contribute to the pathogenesis of AD.

*Staphylococcus aureus* colonises the skin of 90% of AD patients (chronic eczematous lesions) and only 5% of non-atopic patients. The colonisation density of *Staphylococcus aureus* can reach up to $10^7$ colony forming units $cm^{-2}$ without clinical signs of infection in patients with AD. In addition, the apparently normal non-lesional skin of atopic patients contains increased numbers of *Staphylococcus aureus*.

The reason for the overgrowth of *Staphylococcus aureus* in atopic dermatitis, though much less severely or not at all in diseases such as psoriasis, is not known. Protein A elicits a much less vigorous response in atopics than in normals or psoriatics, but this may be the result rather than a cause of colonisation. Attention has recently turned to the skin lipids and there is some evidence that fatty acids which may control staphylococcal colonisation are deficient in atopics.

Superantigens are a unique group of proteins produced by bacteria and viruses that bypass certain elements of the conventional, antigen-mediated immune sequence. Whereas conventional antigens activate approximately 0.01% to 0.01% of the body's T cells, a superantigen has the ability to stimulate 5% to 30% of the T-cell population. *S. aureus* may exacerbate or maintain skin inflammation in AD by secreting a group of exotoxins that act as superantigens. AD patients possess an altered skin barrier secondary to an insufficiency of ceramides within the stratum corneum. It has been proposed that penetration of the skin by these exotoxins may cause activation of T cells, macrophages, LCs, and mast cells, thereby leading to the release of cytokines and mast cell mediators. It is conceivable that these events may provide the basis for inflammation in chronic AD. Speculation remains whether *S. aureus* colonisation and local superantigen secretion is a primary or secondary phenomenon in AD (Andrews' diseases of skin, Chap. 5, Atopic Dermatitis, Eczema, and non-infections immunodeficiency disorders. p. 69-76).

Cutaneous viral, fungal, and bacterial infections occur more commonly in AD patients. Viral infections are consistent with a T cell defect and include herpes simples (local or generalised, i.e. exzema herpeticum), molluscum contagiosum, and human papilloma virus. Superficial fungal infections with *Trichophyton rubrum* and *Pityrosporon ovale* also occur frequently. Bacterial infections, specifically those with *S. aureus*, are extremely common. Superinfection results in honey-coloured crusting, extensive serous weeping or folliculitis.

Type of Wounds

Acute lesions appear as erythematous papules, vesicles, and erosions; chronic disease consists of fibrotic papules and thickened, lichenified skin.

A finding of increasing numbers of pathogenic staphylococci is frequently associated with weeping, crusting, folliculitis and adenopathy. Secondary staphylococcal infection is frequent and local oedema and regional adenopathy commonly occur during atopic dermatitis. Impetigo can be a sort of secondary infection of atopic dermatitis.

The histology of atopic dermatitis ranges from acute spongiotic dermatitis to lichen simplex chronicus, depending on the morphology of the skin lesion biopsied.

Sites of Bacteria

*Staphylococcus aureus* cell walls exhibit receptors, the so-called adhesins, for epidermal and dermal fibronectin and fribrinogen. It has been demonstrated that the binding of *Staphylococcus aureus* was mediated by fibrinogen and fibronectin in AD patients. As the skin of AD patients lacks an intact stratum corneum, dermal fibronectin might be uncovered and increase the adherence of *Staphylococcus aureus*. Fibrillar and amorphous structures have been traced between *Staphylococcus aureus* cells and corneocytes and may results in a bacterial biofilm. It has been observed that *Staphylococcus aureus* penetrates into intracellular spaces suggesting that the skin surface lipids are deteriorated in AD patients (see Breuer K et al., 2002, *British Journal of Dermatology* 147: 55-61).

Ulcers

Skin ulcers, such as diabetic foot ulcers, pressure ulcers, and chronic venous ulcers, are open sores or lesions of the skin characterised by the wasting away of tissue and sometimes accompanied by formation of put. Skin ulcers may have different causes, and affect different populations, but they all tend to heal very slowly, if at all, and can be quite difficult and expensive to treat.

Type of Bacteria

Superficial pressure ulcers are not associated with major infection problems. Aerobic microorganisms at low levels will contaminate pressure ulcers, but will not impede timely healing. However, deep full-thickness pressure ulcers can become secondarily infected, and osteomyelitis can occur. Those pressure ulcers with necrotic tissue contain high levels of aerobic and anaerobic microorganisms as compared to non-necrotic ulcers; foul smell is usually present when anaerobes invade the tissues. Thus, a treatment strategy is to clear necrotic tissue from the wound, producing a decrease in anaerobe presence.

The infections of pressure ulcers are typically polymicrobial and can contain *Streptococcus pyogenes, enterococci,* anaerobic *streptococci, Enterobacteriaece, Pseudomonas airuginosa, Bacteroides fragilis* and *Staphylococcus aureus*.

Type of Wounds

Stage I pressure ulcer: Nonblanchable erythema of intact skin, considered to be heralding lesion of skin ulceration.

Stage II pressure ulcer: Partial thickness skin loss involving the epidermis and/or dermis. The ulcer is superficial and presents clinically as an abrasion, blister, or shallow crater. Because the epidermis may be interrupted by an abrasion, blister, or shallow crater, the ulcer should be evaluated for sings of secondary infections.

Stage III: Full thickness skin loss involving damage or necrosis of subcutaneous tissue which may extend down to, but not through, underlying fascia. The ulcer presents clinically as a deep crater with or without undermining of adjacent tissue.

Stage IV: Full thickness skin loss with extensive destruction, tissue necrosis, or damage to muscle, bone, or supporting structures, such as tendons or joint capsules.

Sites of Bacteria

There are three microbiological states that are possible in a wound: contamination, colonisation and infection. Contamination in characterised as the simple presence of microorganisms in the wound but without proliferation. It is generally accepted that all wounds, regardless of aetiology, are contaminated. Colonisation is characterised as the presence and proliferation of microorganisms in the wound but without host reaction. Colonisation is a common condition in chronic wounds such as venous ulcers and pressure ulcers and does not necessarily delay the healing process. When bacteria invade healthy tissues and continue to proliferate to the extent that their presence and by-products elicit or overwhelm the host immune response, this microbial state is known as infection. The classic signs and symptoms of infection include local redness, pain and swelling, fever and changes in the amount and character of wound exudates.

Lung Infections

The compounds of the invention are also suitable for treating a patient having an infectious disease of the lung, by administering to the subject a compound of the invention and irradiating (i.e. illuminating) the lung with light having a wavelength that causes the compound to produce an antimicrobial effect. Lung infection can occur with a variety of bacterial genera and species, which include *Mycobacterium tuberculosis* (tuberculosis), *Pseudomonas* (primary cause of death of cystic fibrosis patients), *Streptococcus, Staphylococcus pneumoniae, Klebsiella, Toxoplasma*, etc. Lung infection can also occur with a variety of virus strains and opportunistic pathogens (fungi, parasites). As pathogens of the lung are increasingly resistant to classical antibiotic therapies, photodynamic therapy offers an alternative method for eliminating these harmful organisms.

The compound of the invention can be administered to the lung in a variety of ways. For example the compound can be administered by the respiratory tract (i.e. intra-tracheally, intra-bronchially, or intra-alveolarly) or through the body wall of the chest. The light source can be applied through these routes as well with the help of flexible fibre optics for example. The illumination/irradiation can be directed to the base of the lung, to the apex of the lung, or both.

Further Indications

The compounds of the invention are also suitable for the curative and/or prophylactic treatment of the following:

Infections of burn sites and skin grafts; otitis (ear infection), bacterial conjunctivitis and other eye infections, periodonititis and other dental infections, and infected bones exposed during surgical procedures.

Thus, further aspects of the invention provide the following:

(i) Use of a compound of the invention in the preparation of a medicament for use in photodynamic therapy;

(ii) Use of a compound of the invention in the preparation of a medicament for killing and/or preventing growth of microorganisms, such as bacteria, yeasts, fungi and viruses (for example, the medicament may be used to prevent or reduce the spread or transfer of a pathogen to other subjects, e.g. patients, healthcare workers, etc.);

(iii) Use of a compound of the invention in the preparation of a medicament for the curative and/or prophylactic treatment of a dermatological infection;
(iv) Use of a compound of the invention in the preparation of a medicament for the curative and/or prophylactic treatment of an infection of the lungs;
(v) Use of a compound of the invention in the preparation of a medicament for the curative and/or prophylactic treatment of a wound infection and/or an ulcer;
(vi) A method for treating a patient in need of treatment with a photodynamic therapy agent comprising administering to the patient a compound of the invention and illuminating/irradiating the compound; and
(vii) A method for preventing wound infection comprising contacting the wound with a compound of the invention and illuminating/irradiating the compound (such that a reactive oxygen species is generated).

In use, the photosensitive compounds of the invention are illuminated/irradiated, i.e. activated, using conventional techniques known in the field of photodynamic therapy. Preferably, the compounds are illuminated/irradiated at a wavelength of between 400 nm and 800 nm. More preferably, the compounds are illuminated/irradiated at a wavelength corresponding to one or more of the absorption windows for porphyrin, which lie at around 417 nm (Soret band), 485 nm, 515 nm, 550 nm, 590 nm and 650 nm. Most preferably, the compounds are illuminated/irradiated at a wavelength of about 417 nm.

The optimal wavelength will depend on the particular compound and the indication for which is being used. For example, for impetigo, a wavelength of 510 to 560 nm is preferred due to the lesion colour. For open wounds, a wavelength of 560 to 700 is preferred, with preference towards the higher wavelength, in order to minimise activation of haemoglobin (minimum at 690 nm).

It will be appreciated by persons skilled in the art that illumination/irradiation may take place at various time points after application of the compound of the invention. Typically, the compound is illuminated/irradiated between 5 minutes and 2 hours or between 10 minutes and 1 hour. Optimal illumination times may be determined by experimentation.

Where the compound of the invention is applied to the skin, the wavelength of light can be selected so as to control the depth of penetration. For example, for deep penetration longer wavelengths are preferred. Light intensity and overall light dose may also be varied to control the depth of penetration.

Preferably, the photodynamic therapy agent only penetrates the stratum corneum.

Likewise, the optimal duration of the exposure of the compound to illumination/radiation will depend on the particular compound and the indication for which is being used. Typically, however, the illumination time is between 1 and 30 minutes, more preferably between 5 and 20 minutes, for example 10 minutes.

The total amount of illumination/radiation will vary according to the treatment and localisation of the tissues to be treated. Generally, the amount of illumination/radiation is between 10 and 100 $J/cm^2$, preferably between 10 and 350 $J/cm^2$.

Suitable light sources include the PDT 450L, PDT 650L and PDT 1200 lamps from Waldmann AG, Germany. Alternately, white light may be used for compound activation.

The compounds of the invention may also be used to kill microorganisms in vitro. Thus, a further aspect of the invention provides a sterilising solution comprising a compound according to the first and/or second aspects of the invention. The solution may also take the form of a handwash or concentrate to be diluted prior to use.

Preferably, the compound of the invention is present in solution at a concentration of 1 to 100 µg/ml.

Preferably, the solution further comprises a surface-active agent or surfactant. Suitable surfactants include anionic surfactants (e.g. an aliphatic sulphonate), amphoteric and/or zwitterionic surfactants (e.g. derivatives of aliphatic quaternary ammonium, phosphonium and sulfonium compounds) and nonionic surfactants (e.g. aliphatic alcohols, acids, amides or alkyl phenols with alkylene oxides.

Conveniently, the surface-active agent is present at a concentration of 0.5 to 5 weight percent.

The sterilising solutions of the invention are particularly suited for use in hospital environments. For example, the sterilising solutions may be used to sterilise surgical instruments and surgical theatre surfaces, as well as the hands and gloves of theatre personnel. In addition, the sterilising solutions may be used during surgery, for example to sterilise exposed bones. in all cases, the solution is applied to the surface to be sterilised and then illuminated/irradiated so as to produce a reactive oxygen species (see above)

Thus, a further aspect of the invention provides a method for killing microorganisms in vitro comprising contacting the microorganisms to be killed with a compound of the invention and illuminating/irradiating the compound.

DETAILED DESCRIPTION OF THE DRAWINGS

Preferred, non-limiting embodiments of the invention will now be described by way of example, with reference to the accompanying drawings in which.

Figure 5:
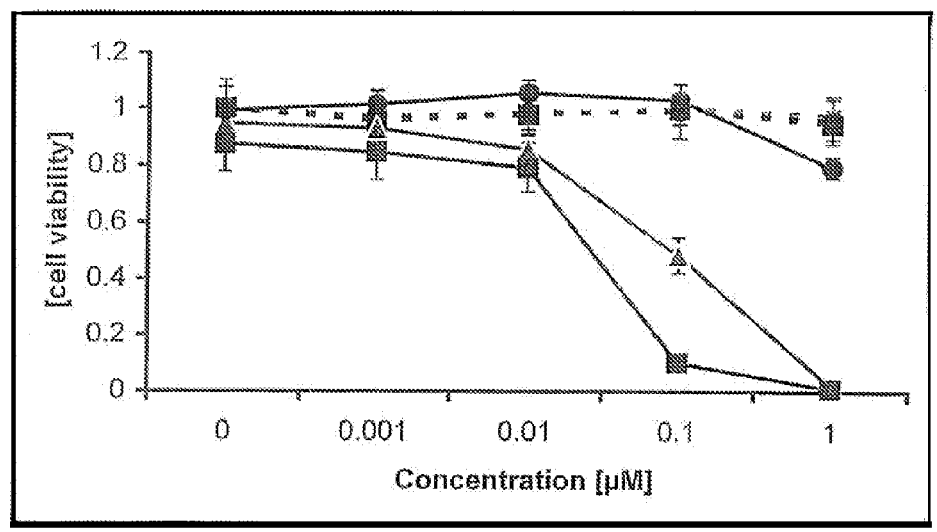

FIG. 5 shows the effects of sodium azide (50 mM) and $D_2O$ on human dermal fibroblast (NHDF) cells incubated with Compound 10, with and without illumination using a light source (236, Waldmann). Triangle/solid line: Compound 10+PBS buffer+light; Squares/solid line: Compound 10+$D_2O$+light; Circles/solid line: Compound 10+sodium azide+light; Triangles/dotted line: Compound 10+PBS buffer w/o light; Squares/dotted line: Compound 10+D$_2$O w/o light; Circles/dotted line: Compound 10+sodium azide w/o light. (n=3, mean±Std).

Figure 6:
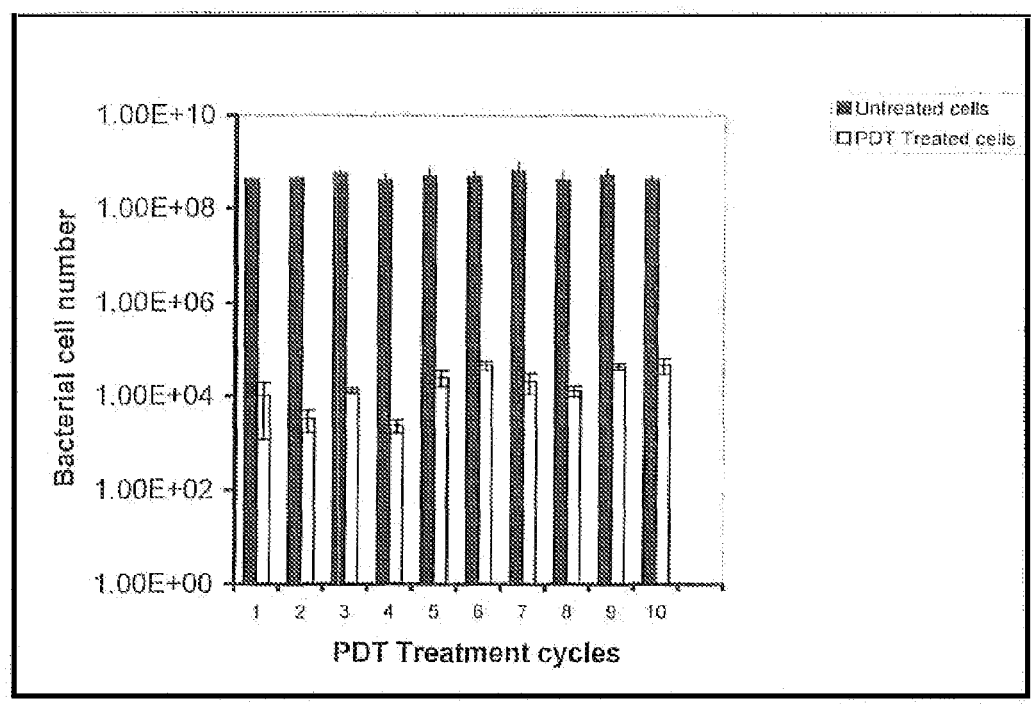

FIG. 6 shows the absence of resistance build-up by *S. aureus* BAA-44 following repeated treatments with Compound 10. Data shown as mean with 95% confidence limit error bars.

Figure 7:
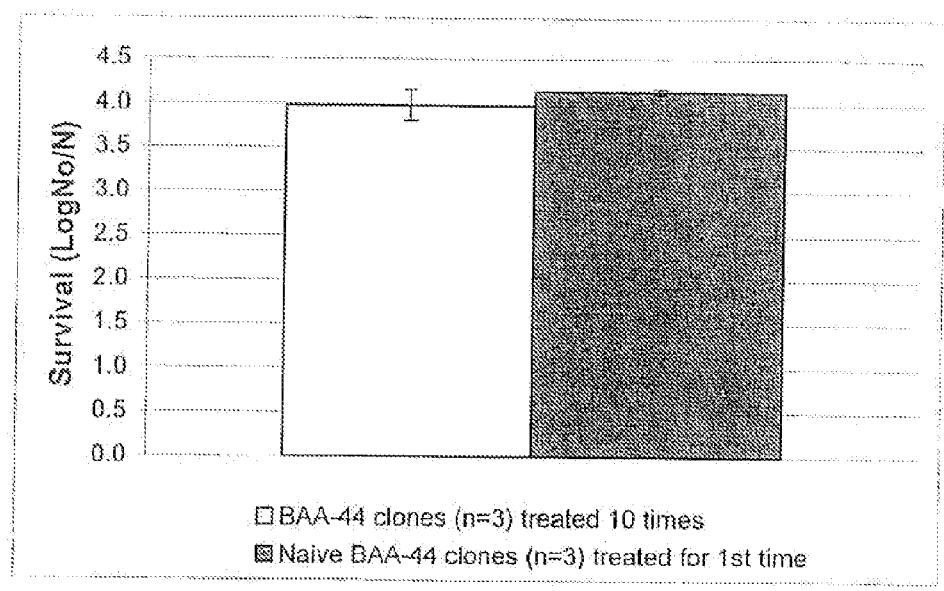

FIG. 7 shows a comparison of survival of clones exposed nine times to PDT treatments with Compound 10 and naïve, untreated clones.

Figure 8:
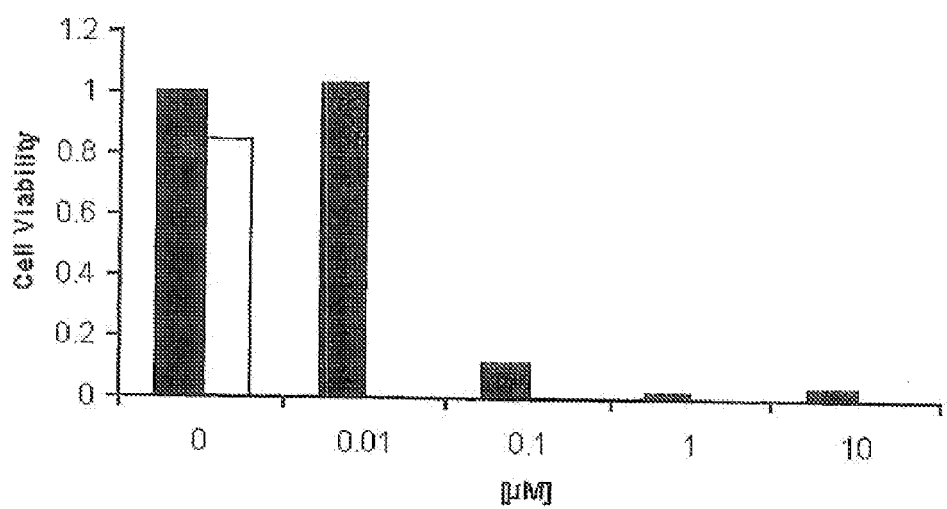

FIG. 8 shows the toxicity of 'Compound 8' against human fibroblasts (shaded bars) and *S. aureus* BAA-44 (open bars) at varying doses.

Figure 9:
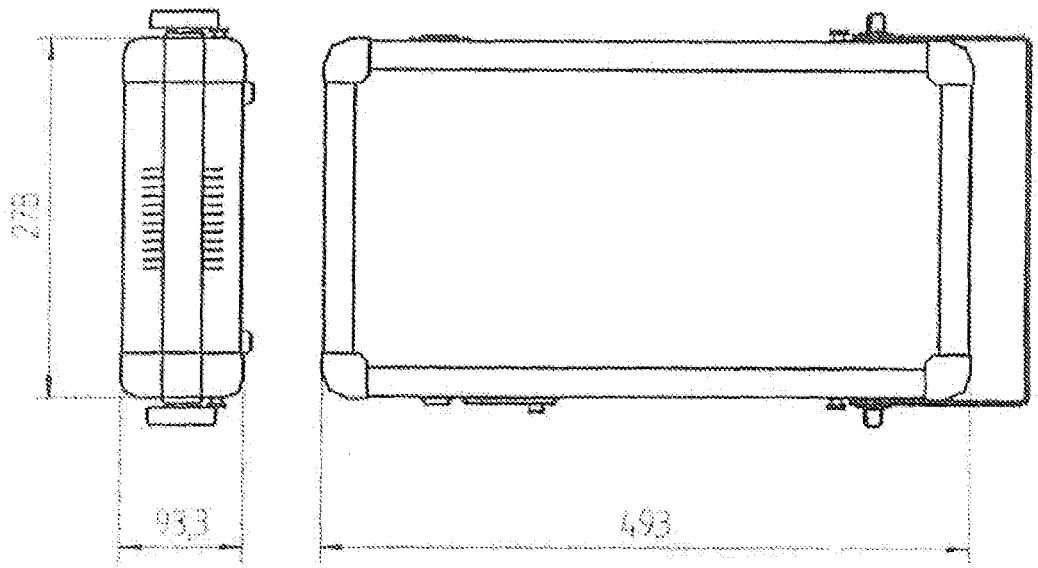

FIG. 9 shows a dimensional drawing of a 236 light source (Waldmann).

Figure 10A:
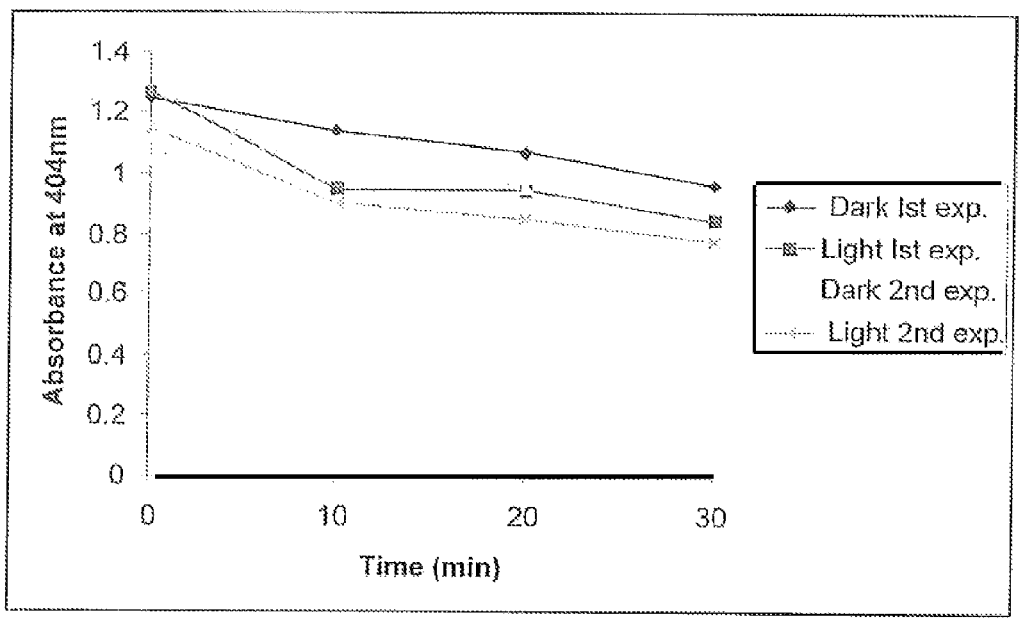
Figure 10B:
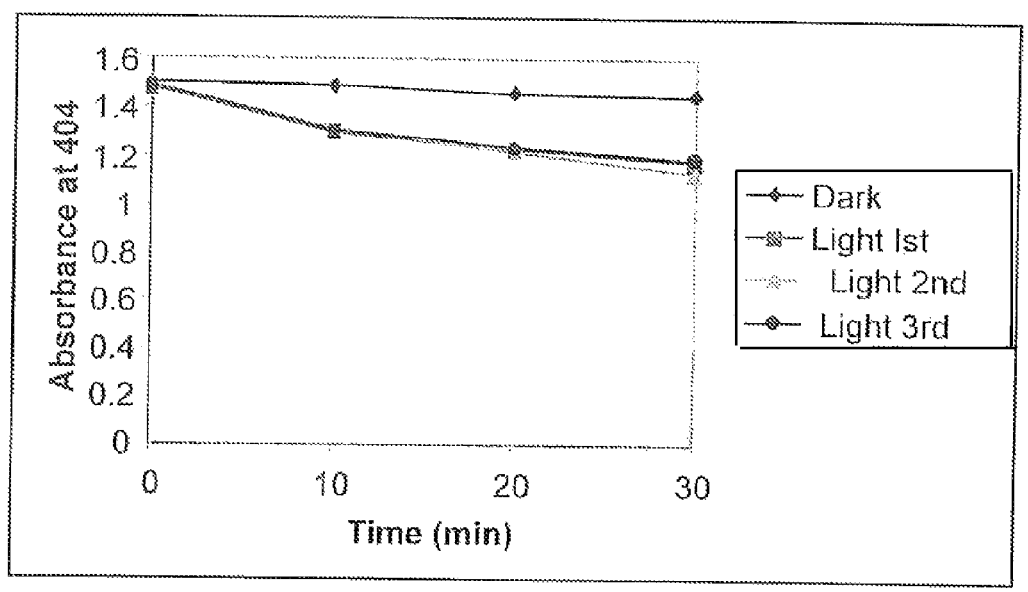

FIG. 10 shows photobleaching of 10 μM Compound 10 illuminated for various times with blue light at (A) 15 mW/cm$^2$ and (B) 150 mW/cm$^2$.

Figure 11A:
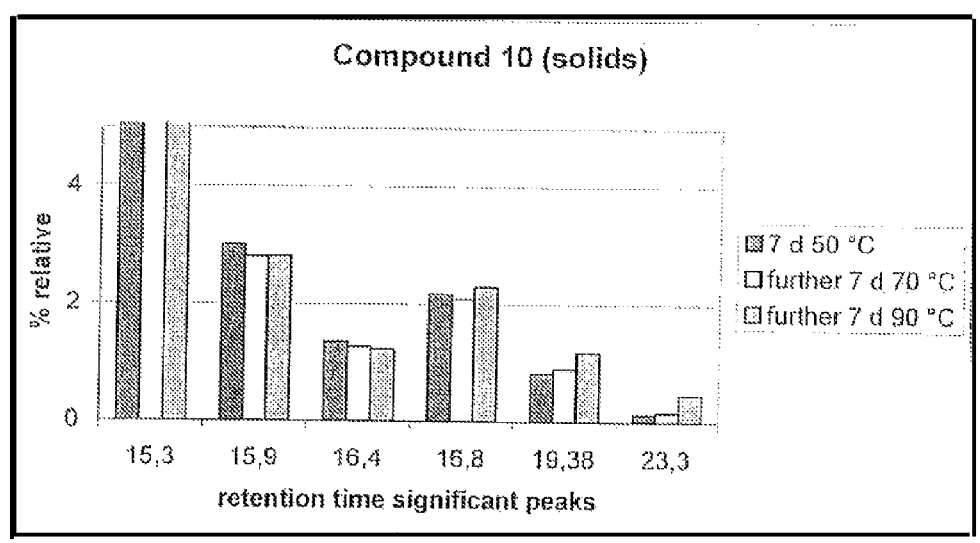
Figure 11B:
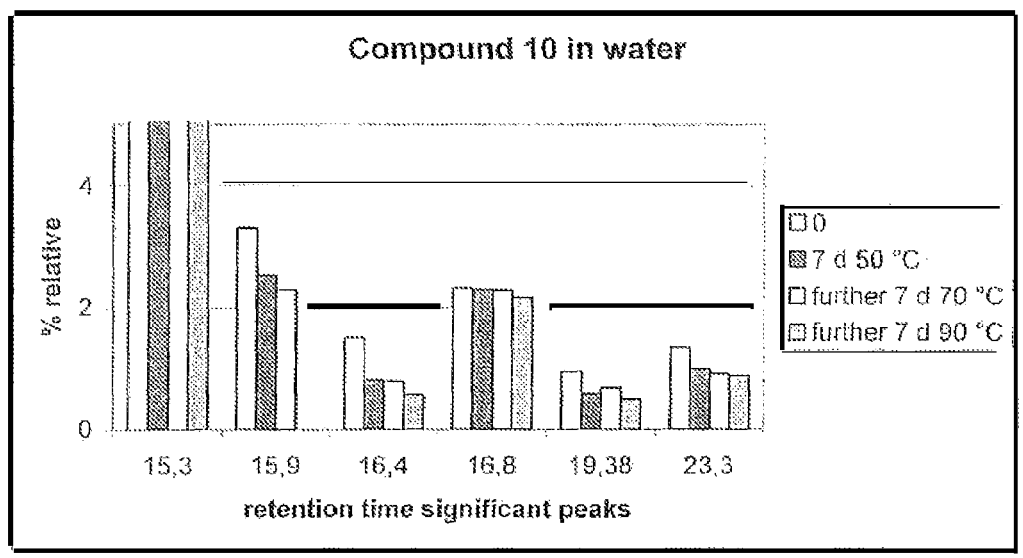
Figure 11C:
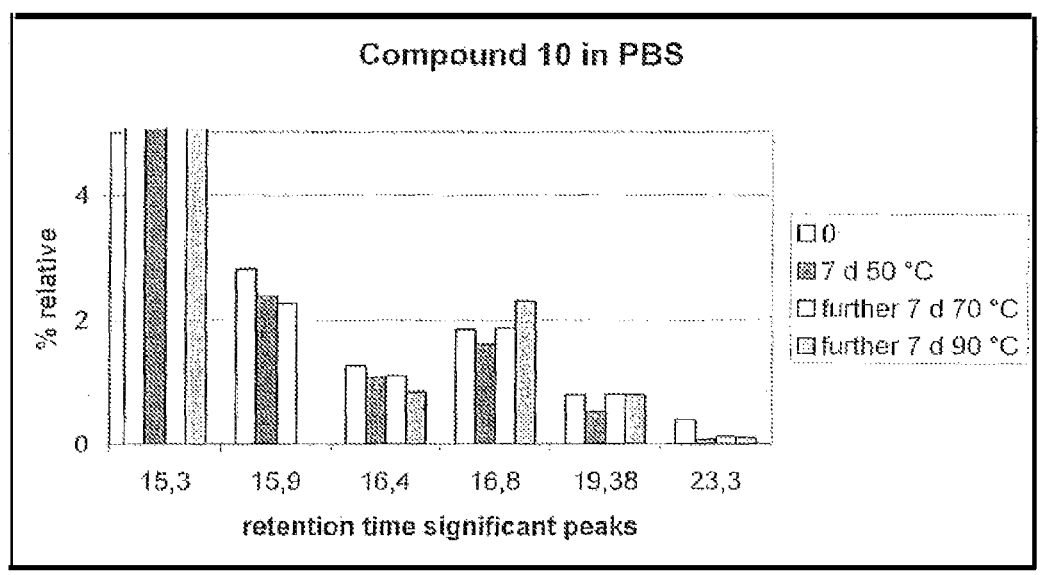

FIG. 11 shows the chemical stability of Compound 10 formulated (A) as a solid, (B) in water and (C) in PBS.

Figure 12:
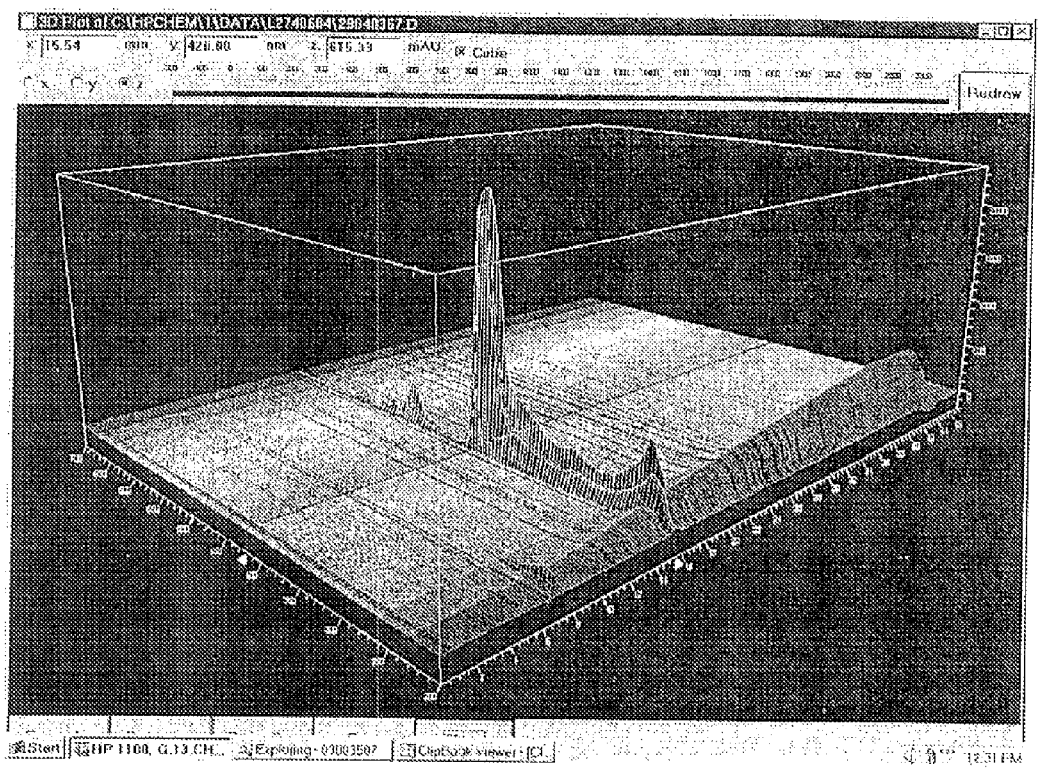
Figure 13A:
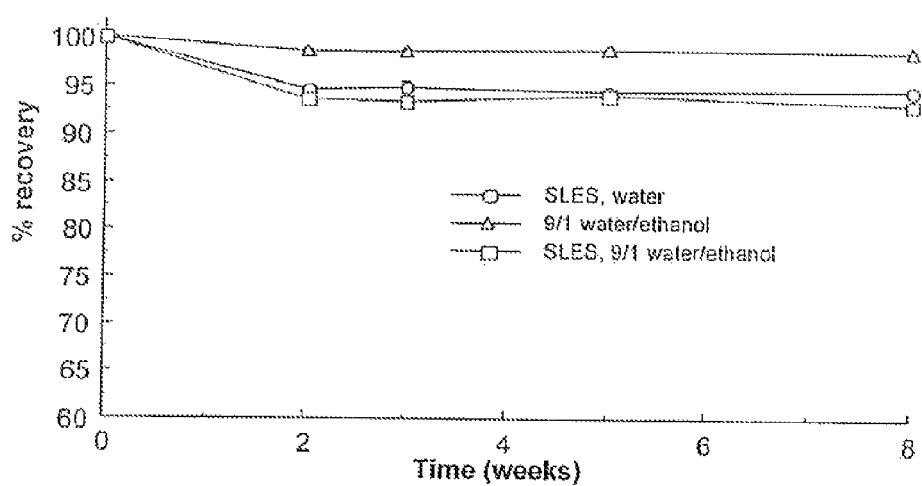
Figure 13B:
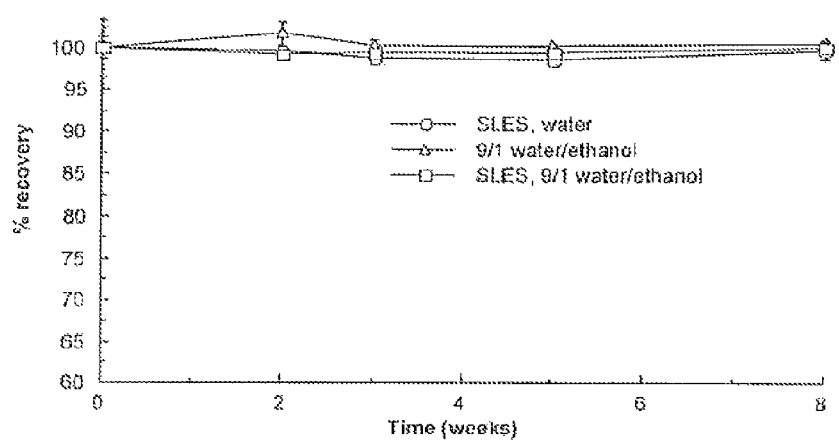
Figure 13C:
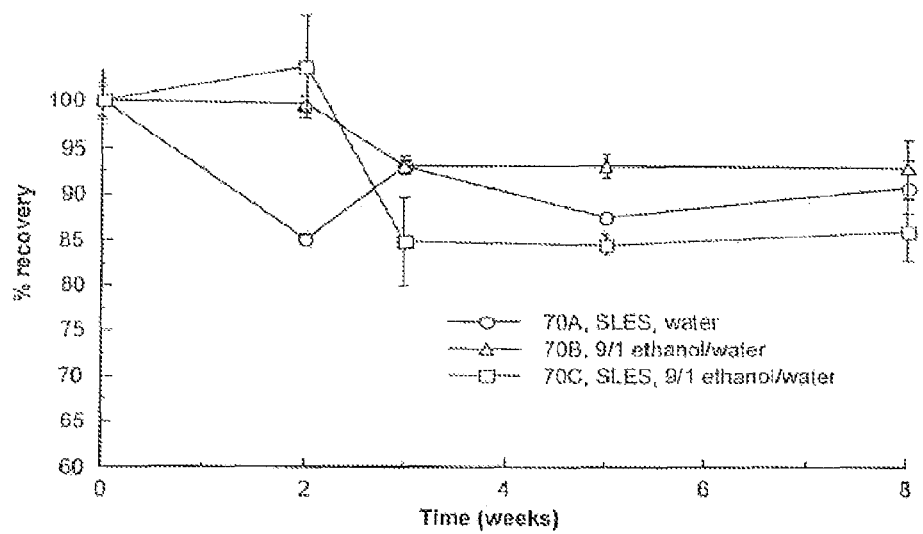
Figure 13D:
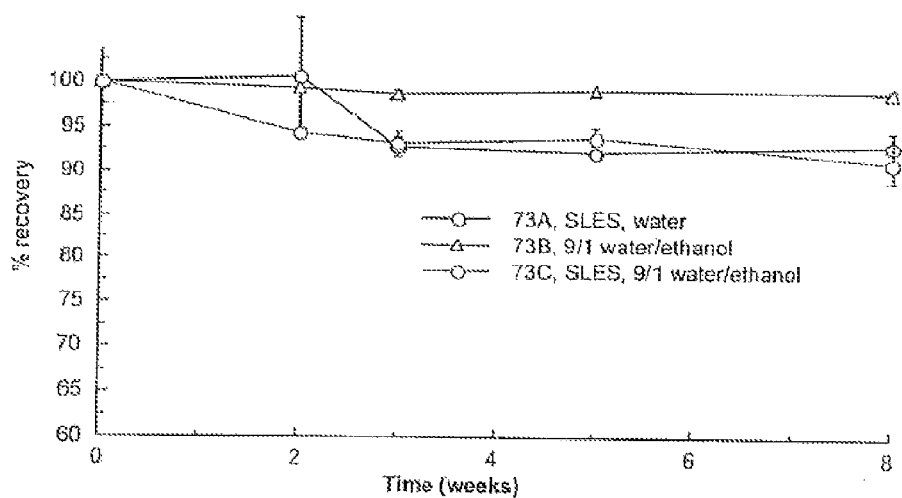

FIG. 12 shows a 3D plot of the stability (measured by HPLC) of Compound 10 after 21 days in PBS buffer.

FIG. 13 shows the stability over 8 weeks of various formulations of (A) Compound 1, (B) Compound 8, (C) Compound 12 and (D) Compound 10.

Figure 14A:
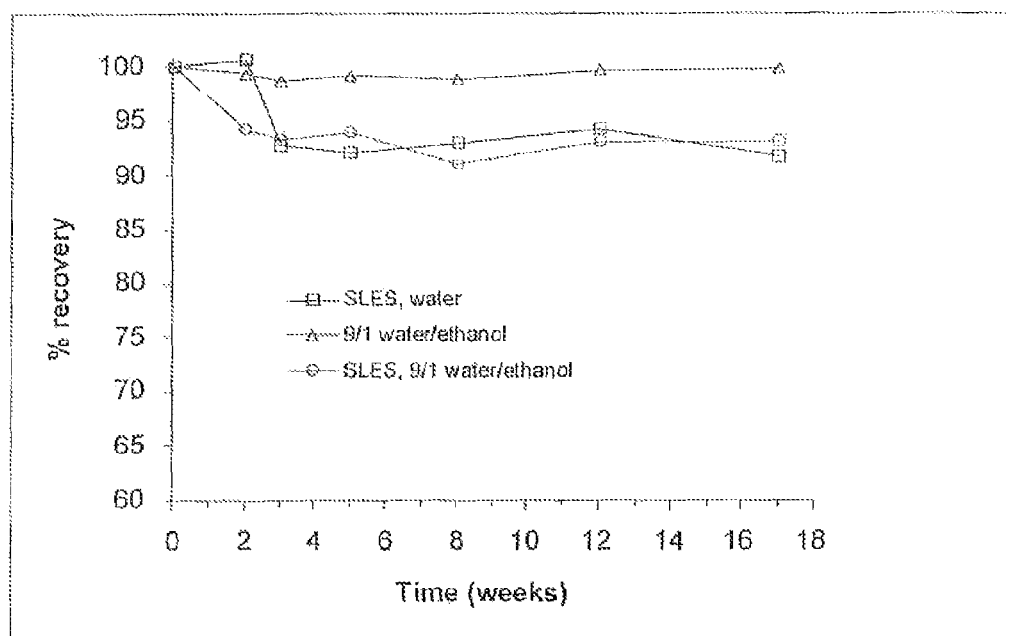
Figure 14B:
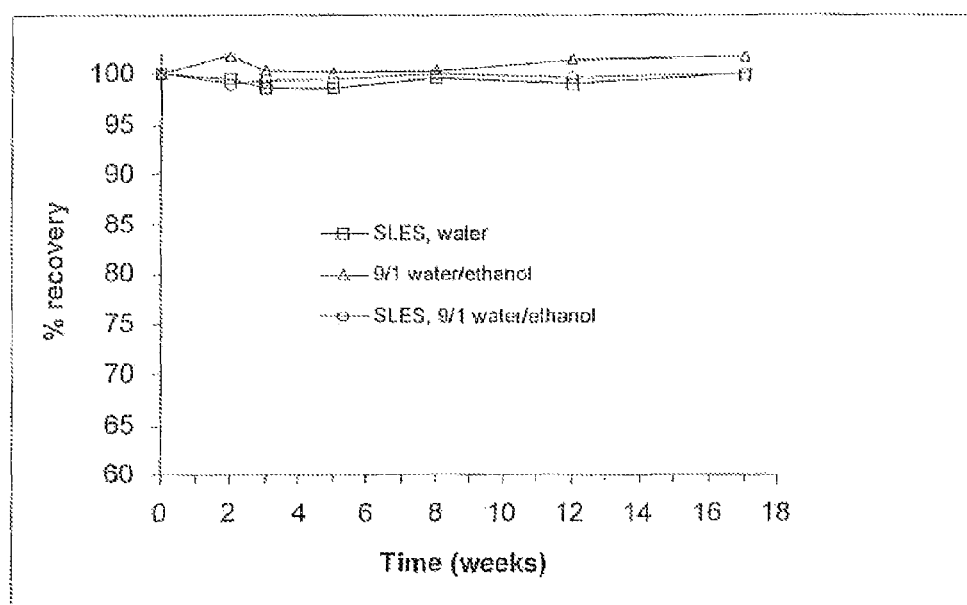

FIG. 14 shows the extended stability over 17 weeks of various formulations of (A) Compound 10 and (B) Compound 8.

EXAMPLES

Example A

Synthesis of Exemplary Compounds

Materials and Methods
NMR-Measurements
Proton NMR spectra were recorded on a Bruker B-ACS60 (300 MHz) instrument using TMS as internal standard. The chemical shifts are given in ppm and coupling constants in Hz in the indicated solvent. Some abbreviation for NMR: single (s), broad singlet (bs), doublet (d), triplet (t), quartet (q), multiplet (m).
Chemicals
All solvents and reagents were purchased from Aldrich, Fluka, Merck and Lancaster and used without further purification.
Dipyrrolmethane was prepared as described by C Brücker et al., *J. Porphyrins Phthalocyanines*, 2 445 (1998).
Chromatography
Column chromatography was carried out using silica gel (Merck Silicagel 60, Fluka 60, 0.040-0.063 mm) and Sephadex LH-20 (Pharmacia). All solvents (Synopharm) for chromatography were technical pure grade.
Abbreviations
  DDQ: 2,3-dichloro-5,6-dicyano-p-benzoquinone
  DMF: N,N-dimethylformamide
  TFA: trifluoroacetic acid
Synthesis Routes for Test Compounds
  The following test compounds were synthesised:
Exemplary Compounds of the Invention
  Compounds 6, 8 to 10, 12, 23, 25, 28, 31 and 32.

Reference Compounds (For Use as Comparative Controls)
  Compounds 1, 3, 16, 19, 26, 29, 33, 36, 37, 39, 41 and 46 to 51.
Chemical Intermediates
  Compounds 2, 4, 5, 7, 11, 13 to 15, 17, 18, 20 to 22, 24, 27, 30, 34, 35, 38, 40 and 42 to 45.

COMPOUND 1

5,10,15,20-tetrakis-[4-(3-Trimethylammonio-propyloxy)-phenyl]-porphyrin tetrachloride

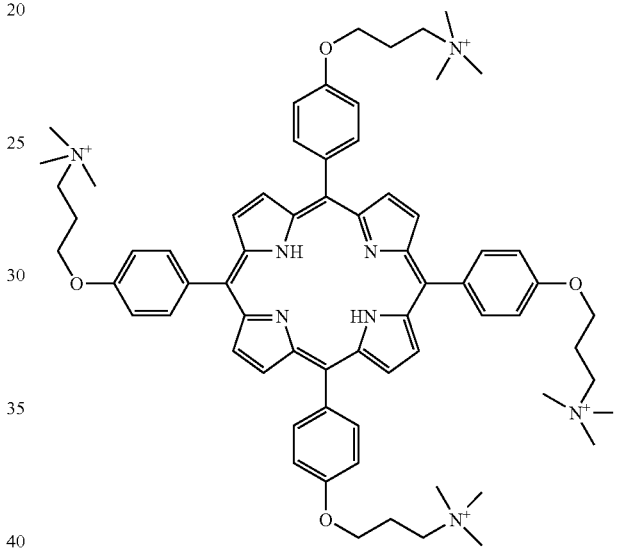

To a vigorously-stirred suspension of 5,10,15,20-tetrakis-(4-hydroxy-phenyl)-porphyrin (50 mg, 0.07 mmol) and K$_2$CO$_3$ (230 mg, 1.7 mmol) in DMF (20 mL), a solution of (1-bromopropyl)-trimethylammonium bromide (0.27 g, 1.05 mmol) in DMF (5 mL) is added dropwise at 50° C. during 30 mins. The mixture is stirred at 50° C. for 15 h. After removal of DMF under reduced pressure, the residue obtained is dissolved in methanol (5 mL) and filtered through a pad of silica gel (depth 2 cm) supported on a steel frit (diameter 3.5 cm). After washing with methanol (1 L), the pad is eluted with acetic acid. After evaporation of solvent from the eluate, the residue obtained is purified by chromatography on a column (2.5×40 cm) of Sephadex LH20 eluting with n-butanol:water:acetic acid (4:5:1, by vol., upper phase). The recovered material is dissolved in the minimum volume of methanol and the solution is passed through a short column (3.5×20 cm) of anion exchange resin (Amberlite IRA 400, chloride form). The recovered tetrachloride salt is dried under high vacuum and obtained as violet crystals.

$^1$H-NMR: $\delta_H$ (300 MHz, CD$_3$OD): 2.35-2.50 (bs, 8 H), 3.25-3.35 (bs, 36 H), 3.65-3.75 (bs, 8 H), 4.35 (m, 8 H), 7.30, 8.10 (2×d, $^3$J 8.5 Hz, 16 H), 8.80-9.00 (bs, 8 H).

COMPOUND 2

5,10,15-tris-(4-Hydroxy-phenyl)-20-(4-undecyloxy-phenyl)-porphyrin

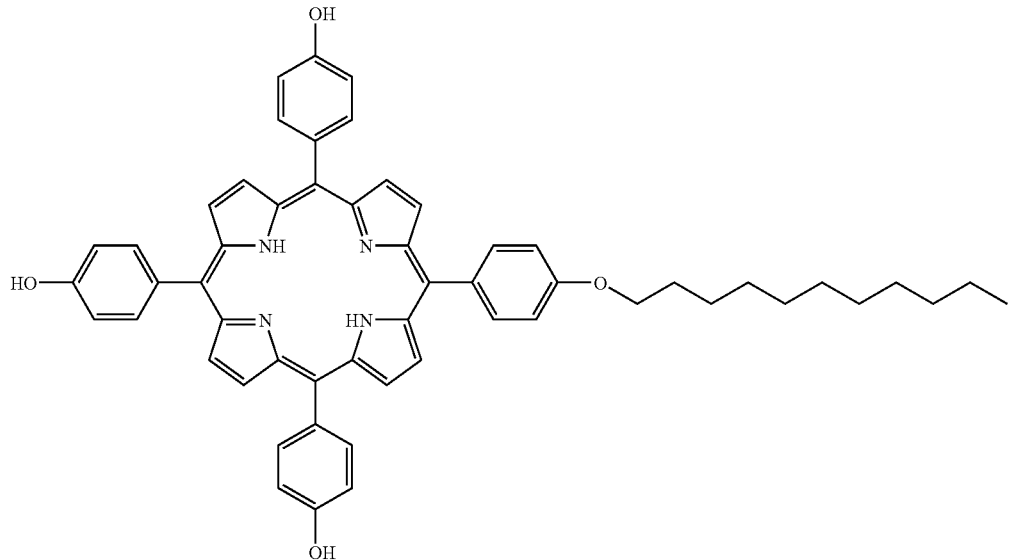

To a vigorously-stirred suspension of 5,10,15,20-tetrakis-(4-hydroxy-phenyl)-porphyrin (400 mg, 0.59 mmol) and $K_2CO_3$ (1.0 g, 7.1 mmol) in DMF (10 mL) is added dropwise at 50° C. during 30 mins and the mixture is stirred at the same temperature for 1.5 h. After removal by filtration of $K_2CO_3$ and removal under reduced pressure of DMF, the residue obtained is dissolved in dichloromethane (200 mL), washed with water (3×150 mL) and the solution dried ($Na_2SO_4$). The solvent is evaporated under reduced pressure and the residue obtained is dissolved in toluene:ethanol (5:1 by vol., ca. 10 mL) and purified by chromatography using a column (5×5 cm) of silica gel (Merck 60). The column is eluted with toluene followed by toluene:ethyl acetate (2:1 by vol.) and the desired material recovered by evaporation of solvent from the appropriate fractions is dried under high vacuum. The product is obtained as violet crystals.

$^1$H-NMR $\delta_H$ (300 Mz, d6-acetone): 0.95 (t, $^3J$ 7.5 Hz, 3 H), 1.25-1.35 (m, 14 H), 1.58 (quint, $^3J$ 7.5 Hz, 2 H), 1.85 (quint, $^3J$ 7.5 Hz, 2 H), 4.16 (t, $^3J$ 7.5 Hz, 2 H), 7.20 (d, $^3J$ 8.1 Hz, 2 H), 7.25 (d, $^3J$ 8.2 Hz, 6 H), 8.00-8.15 (m, 8 H), 8.80-9.10 (m, 8 H).

COMPOUND 3

5,10,15-tris-[4-(3-Trimethylammonio-propyloxy)-phenyl]-20-(4-undecyloxy-phenyl)-porphyrin trichloride

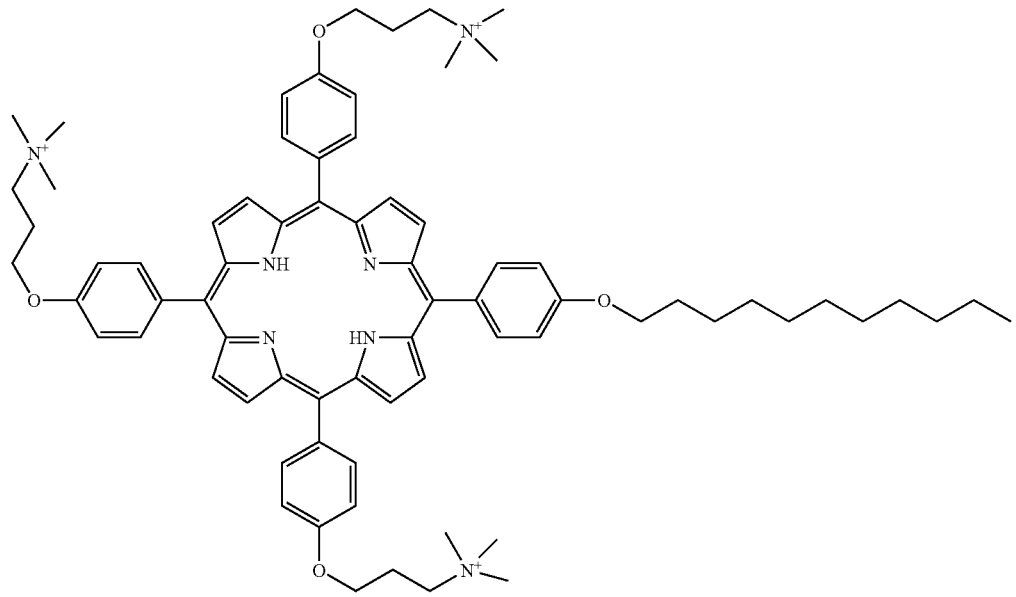

To a vigorously-stirred suspension of Compound 2 (100 mg, 0.12 mmol) and K$_2$CO$_3$ (230 mg, 1.7 mmol) in DMF (30 mL), a solution of (1-bromopropyl)-trimethylammonium bromide (0.3 g, 16.6 mmol) in DMF (10 mL) is added at 50° C. and the mixture is stirred at this temperature for 12 h. After removal of the DMF under reduced pressure, the residue obtained is dissolved in methanol (5 mL) and filtered through a pad of silica gel (depth 2 cm) supported on a steel frit (diameter 3.5 cm). After washing with methanol (ca. 1 L), the pad is eluted with acetic aced:methanol:water (3:2:1, by vol.). After evaporation of the solvent from the eluate under reduced pressure, the residue obtained is purified by chromatography on a column (2.5×40 cm) of Sephadex LH-20 eluting with n-butanol:water:acetic acid (5:4:1, by vol., upper phase). After removal of the solvent from appropriate fractions of the eluate under reduced pressure, the residue obtained is dissolved in methanol (5 mL) and the solution is passed through a short column (3.5×20 cm) of anion exchange resin (Amberlite IRA 400, chloride form). The final product is obtained as the trichloride salt, after removal of solvent and drying under high vacuum, as violet crystals.

$^1$H-NMR: $\delta_H$ (300 MHz, CD$_2$OD): 0.80 (t, $^3$J 7.5 Hz, 3 H), 1.15-1.45 (m, 16 H), 1.50-1.60 (bs, 2 H), 2.25-2.45 (bs, 6 H), 3.25-3.35 (bs, 27 H), 3.75-3.85 (bs, 6 H), 4.18 (t, $^3$J 7.5 Hz, 2 H), 4.40-4.45 (bs, 6 H), 7.20-7.40, 7.95-8.15 (2×m, 16 H), 8.60-9.00 (bs, 8 H).

COMPOUND 4

5-(3,5-Dimethoxy-phenyl)-15-undecyl-porphyrin

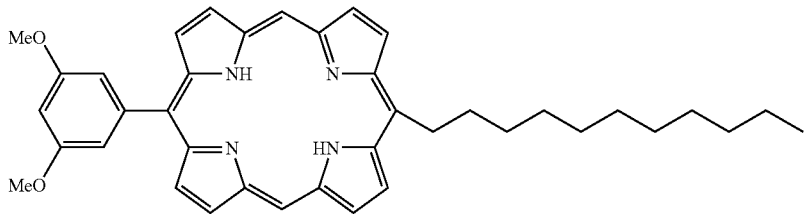

To a stirred solution of dipyrrolemethane (0.62 g, 4.2 mmol) in dichloromethane (5 mL) is added 3,5-dimethoxy-benzaldehyde (0.35 g, 2.1 mmol) and dodecanal (0.464 g, 2.52 mmol) in degassed dichloromethane (1 L). TFA (0.07 mL, 3.0 mmol) is added dropwise. The solution is stirred at room temperature in the dark for 17 h under argon. After addition of DDG (2.7 g, 12 mmol), the mixture is stirred at room temperature for a further hour. Purification of material recovered after removal of solvent under reduced pressure by chromatography on a column (400 g) of silica gel (Merck 60) with toluene for elution yields the product as violet crystals.

$^1$H-NMR: $\delta_H$ (300 Mz, CDCl$_3$): 0.80 (t, $^3$J 7.5 Hz, 3 H), 1.10-1.25 (m, 12 H), 1.40 (m, 2H), 1.75 (quint, $^3$J 7.5 Hz, 2 H), 2.45 (quint, $^3$J 7.5 Hz, 2 H), 3.90 (s, 6H), 4.90 (t, $^3$J 7.5 Hz, 2 H), 6.80 (m, 1 H), 7.35 (m, 2 H), 9.00, 9.25 9.30, 9.50 (4×d, $^3$J 4.7 Hz, 4×2 H), 10.15 (s, 2H).

COMPOUND 5

5-(15-Undecyl-porphyrin-5-yl)-benzene-1,3-diol

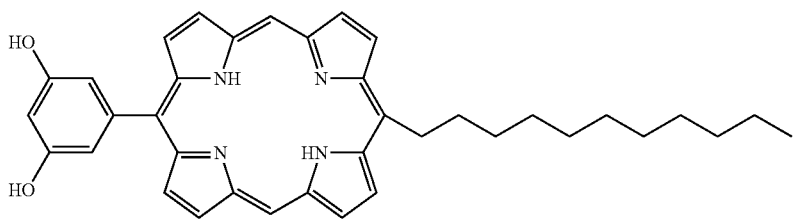

To a solution of Compound 4 (80 mg, 0.133 mmol) in anhydrous dichloromethane (80 mL) under an argon atmosphere, BBr$_3$ (5 mL, 1M in dichloromethane) is added dropwise at −70° C. and the mixture is stirred for 1 h at this temperature and then warmed to room temperature and stirred overnight. The mixture is cooled to −10° C. and hydrolysed by the addition of water (2 mL) and stirring for 1 h. NaHCO$_3$ (3 g) is added directly for neutralisation. The mixture is stirred for a further 12 h and after filtration of NaHCO$_3$ and removal of dichoromethane under vacuum the residue obtained is purified by column chromatography using silica gel eluting with dichloromethane. After evaporation of solvent from appropriate combined fractions and drying of the residue obtained under high vacuum the product is obtained as violet crystals.

$^1$H-NMR: $\delta_H$ (300 Mz, d6-acetone): 0.75 (t, $^3$J 7.5 Hz, 3 H), 1.05-1.25 (m, 12 H), 1.30-1.40 (m, 2H), 1.45-1.50 (m, 2 H), 2.40 (quint, $^3$J 7.5 Hz, 2 H), 4.90 (t, $^3$J 7.5 Hz, 2 H), 6.65 (m, 1 H), 7.18 (m, 2 H), 8.60-8.65, 9.00-9.05, 9.35-9.40, 9.55-9.60 (4×m, 8 H), 10.25 (s, 2H).

COMPOUND 6

5-[3,5-bis-(3-Trimethylammonio-propyloxy)-phenyl]-15-undecyl-porphyrin dichloride

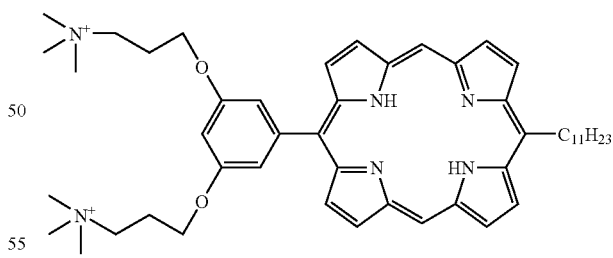

To a vigorously-stirred suspension of Compound 5 (80 mg, 0.14 mmol) and K$_2$CO$_3$ (230 mg, 1.7 mmol) in DMF (30 mL) is added (1-bromopropyl)-trimethylammonium bromide (0.3 g, 16.6 mmol) at 50° C. The mixture is stirred at this temperature for 18 h. After removal of the DMF under reduced pressure, the residue obtained is dissolved in methanol (5 mL) and filtered through a pad of silica gel (depth 2 cm) supported on a steel frit (diameter 3.5 cm). After washing the pad with methanol (ca. 1 L) the crude product is eluted with acetic acid:methanol:water (3:2:1, by vol.). Appropriate fractions are collect and, after evaporation of the solvent under reduced pressure, the residue obtained is purified by chromatography on a column (2.5×40 cm) of Sephadex LH-20 eluting with n-butanol:water:acetic acid (5:4:1, by vol., upper phase). After removal of the solvent from appropriate fractions under reduced pressure, the residue obtained is dissolved in methanol (5 mL) and the solution is passed through a short column (3.5×20 cm) of anion exchange resin (Amberlite IRA 400, chloride form). After collection of the eluate, solvent is removed under reduced pressure and the residue obtained is dried under high vacuum to yield the dichloride salt as violet crystals.

$^1$H—HMR: $\delta_H$ (300 Mz, CD$_3$OD): 0.75 (t, $^3$J 7.5 Hz, 3 H), 1.05-1.20 (m, 14 H), 1.45-1.50 (m, 2 H), 2.05-2.15 (m, 4 H), 2.15-2.20 (m, 2 H), 2.95 (s, 18 H), 3.35-3.45 (m, 4 H), 3.95 (t, $^3$J 7.5 Hz, 4 H), 4.55 (t, $^3$J 7.5 Hz, 2 H), 6.85 (m, 1 H), 7.35 (m, 2 H), 8.85-8.90, 9.15-9.20, (3×m, 8 H), 10.10 (s, 2 H).

COMPOUND 7

5,15-bis-[4-(3-Bromo-propyloxy)-phenyl]-porphyrin

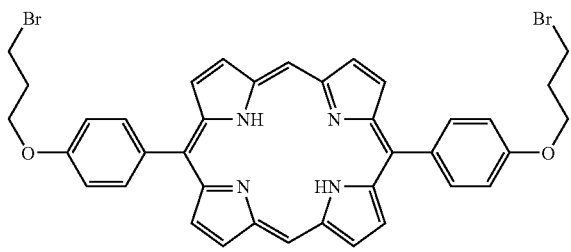

To a stirred solution of dipyrrolemethane (0.61 g, 4.1 mmol) and 4-(3-bromopropyloxy)-benzaldehyde (1.03 g, 4.2 mmol) in degassed dichloromethane (1 L), TFA (0.07 mL, 1.5 mmol) is added dropwise. The solution is stirred at room temperature in the dark under argon for 17 h. After addition of DDQ (2.76 g, 0.012 mmol), the mixture is stirred at room temperature for a further hour. Filtration through silica gel (Fluka 60, 100 g) using dichloromethane for elution gives raw product which, after recrystallisation from dichloromethane: n-hexane, yields pure product as violet crystals.

$^1$H-NMR: $\delta_H$ (300 Mz, C$_6$D$_6$): −3.15 (2 H), 2.00 (quint, $^3$J 7.5 Hz, 4 H), 3.30 (t, $^3$J 7.5 Hz, 4 H), 3.90 (t, $^3$J 7.5 Hz, 4 H), 7.15-7.18, 7.95-8.15 (2×4 H), 9.15-9.20, (m, 8 H), 10.05 (s, 2H).

COMPOUND 8

5,15-bis-(4-{3-[(3-Dimethylamino-propyl)-dimethyl ammonio]-propyloxy}-phenyl)-porphyrin dichloride

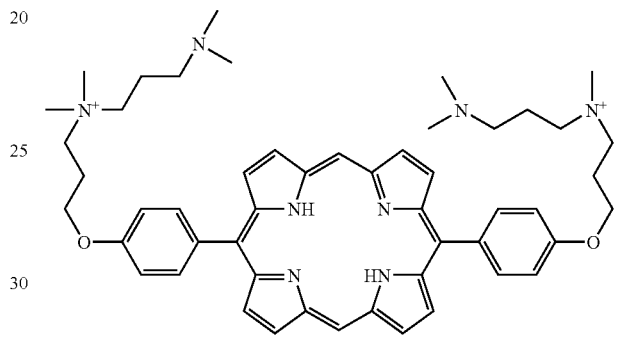

Compound 7 (200 mg, 0.27 mmol) is dissolved in absolute DMF (40 mL) with N,N,N',N'-tetramethyl-1,3-propanediamine (5 mL, 13.9 mmol) and the solution is stirred at 50° C. under argon overnight. After evaporation of the solvent under reduced pressure, the residue obtained is dissolved in methanol (5 mL) and the solution is filtered through a pad of silica gel (depth 2 cm) supported on a steel frit (diameter 3.5 cm). The pad is eluted with methanol (ca. 1 L) followed by acetic acid:methanol:water (3:2:1, by vol.). After evaporation of the solvent from appropriate fractions, the raw product obtained is dissolved in methanol (5 mL) and further purified by chromatography on a column (2.5×40 cm) of Sephadex LH-20 using n-butanol:water:acetic acid (4:5:1, by vol., upper phase) as the developing phase. The first fraction eluted is the desired product. After removal of solvent under reduced pressure the residue obtained is dissolved in methanol (5 mL) and passed through a short column (3.5×20 cm) of anion exchange resin (Amberlite IRA 400, chloride form). After removal of solvent under reduced pressure from the eluate, the residue is crystallised from diethylether and dried under high vacuum to give the product as violet crystals.

$^1$H-NMR: $\delta_H$ (300 MHz, CD$_3$OD): 2.20-2.35 (m, 4 H), 2.40-2.50 (m, 4 H), 2.80 (s, 12 H), 3.05 (4 H, t, $^3$J 7.8, 2 H), 3.25 (s, 12 H), 3.45-3.55 (bs, 4 H), 3.65-3.75 (m, 4 H), 4.30 (t, $^3$J 4.2 Hz, 4 H), 7.40, 8.10 (2×d, $^3$J 7.5 Hz, 2×4 H), 8.95, 9.45 (2×d, $^3$J 4.2 Hz, 8 H), 10.40 (s, 2 H).

COMPOUND 9

5,15-bis-[4-(3-Triethylammonio-propyloxy)-phenyl]-porphyrin dichloride

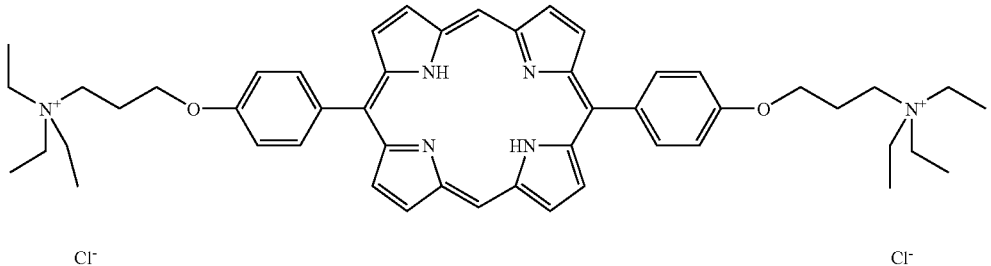

To a solution of Compound 7 (50 mg, 0.068 mmol) in absolute DMF (20 mL) is added triethylamine (4.7 mL, 0.034 mol, 500 eq.). The mixture is stirred at 60° C. for 24 h. The solvent is removed under reduced pressure and the residue obtained is dissolved in methanol (5 mL) and filtered through a pad of silica gel (depth 2 cm) supported on a steel frit (diameter 3.5 cm). After washing with methanol (ca. 1 L) the pad is eluted with acetic acid:methanol:water (3:2:1, by vol.). After evaporation of the solvent from the eluted fraction, the raw product obtained is dissolved in methanol (5 mL) and purified by chromatography on a column (2.5×40 cm) of Sephadex LH-20 eluting with n-butanol:water:acetic acid (4:5:1, by vol., upper phase). The solvents are removed under reduced pressure from appropriate fractions, the residue obtained is dissolved in methanol (5 mL) and the solution is passed through a short column (3.5×20 cm) of anion exchange resin (Amberlite IRA 400, chloride form) to yield the product as a violet solid after evaporation of solvent.

$^1$H-NMR: $\delta_H$ (300 Mz, CD$_3$OD): 1.25 (m, 18H), 2.13 (m, 4H), the signals for —CH$_2$NCH$_2$ (16H) are in the area 3.00-3.40 as a part of the multiplet covered by the solvent signals, 4.15 (t, 4H, $^3$J=7.5 Hz), 7.36 (d, 4H, $^3$J=7.5 Hz), 8.15 (d, 4H, $^3$J=7.5 Hz), 9.05 (d, 4H, $^3$J=7.5 Hz), 9.54 (d, 4H, $^3$J=7.5 Hz), 10.45 (s, 2H)

COMPOUND 10

5,15-bis-[4-(3-Trimethylammonio-propyloxy)-phenyl]-porphyrin dichloride

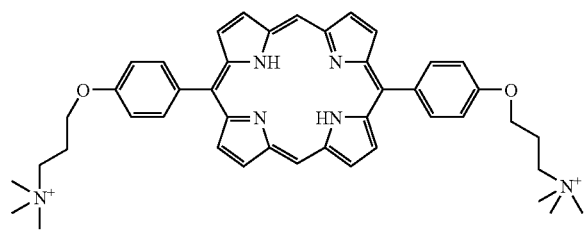

A solution of Compound 7 (300 mg, 0.41 mmol) in absolute DMF (50 mL) is transferred into a 100 mL autoclave. After addition of trimethylamine (4.5 g), the mixture is stirred at 50° C. for 16 h. After evaporation of the solvent, the residue obtained is dissolved in methanol (5 mL) and the solution is filtered through a pad of silica gel (depth 2 cm) supported on a steel frit (diameter 3.5 cm). After washing with methanol (ca. 1 L) the pad is eluted with acetic acid:methanol:water (3:2:1, by vol.). After evaporation of the solvent from appropriate fractions, the residue obtained is dissolved in methanol (5 mL) and purified by chromatography on a column (2.5×40 cm) of Sephadex LH-20, eluting with n-butanol:water:acetic acid (4:5:1, by vol., upper phase). Two fractions are obtained, the first-eluting of which is the desired product. The solvent is removed under reduced pressure and the residue obtained is redissolved in methanol (5 mL) and the solution is passed through a short column (3.5×20 cm) of anion exchange resin (Amberlite IRA 400, chloride form). After evaporation of the solvent under reduced pressure, the residue is crystallised from methanol:diethyl ether and dried under high vacuum to give the product as violet crystals.

$^1$H-NMR: $\delta_H$ (300 Mz, CD$_3$OD): 2.40-2.60 (m, 4 H), 3.30-3.25 (bs, 18 H), 3.75-3.80 (m, 4 H), 4.40(t, $^3$J 7.5 Hz, 4 H), 7.40-8.20 (2×d, $^3$J 8.5 Hz, 8 H), 9.05, 9.50 (2×d, $^3$J 4.5 Hz, 8 H), 10.45 (s, 2 H).

COMPOUND 11

5,15-bis-[3-(3-Bromo-propyloxy)-phenyl]-porphyin

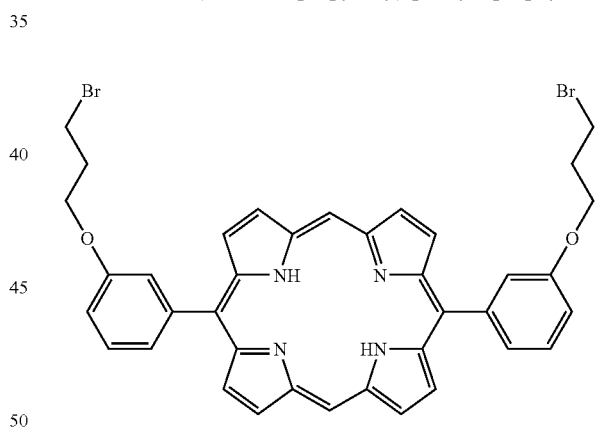

To a stirred solution of dipyrrolemethane (1.22 g, 8.2 mmol) and 3-(3-bromo-propyloxy)-benzaldehyde (2.06 g, 8.2 mmol) in degassed dichloromethane (2 L), TFA (0.14 mL, 3 mmol) is added dropwise. The solution is stirred at room temperature in the dark for 17 h under argon. After addition of DDQ (5.4 g, 0.024 mol), the mixture is stirred at room temperature for a further 1 h. After removal of solvents under reduced pressure, the residue obtained is dissolved in dichloromethane (5 mL) and passed through a column (300 g) of silica (Fluka 60) using dichloromethane as eluent to give raw product which is crystallised from dichloromethane:methanol to yield pure material as violet crystals.

$^1$H-NMR: $\delta_H$ (300 Mz, CDCl$_3$): −3.20 (2 H, s) 2.40 (quint, $^3$J 7.5 Hz, 4 H), 3.65 (t, $^3$J 7.5 Hz, 4 H), 4.25 (t, $^3$J 7.5 Hz, 4 H), 7.20-7.25, 7.60-7.65, 7.75-7.80 (3×m, 8 H), 9.05, 9.25, (2×d, $^3$J 4.2 Hz, 8 H), 10.25 (s, 2 H).

COMPOUND 12

5,15-bis-[3-(3-trimethylammonio-propyloxy)-phenyl]-porphyrin dichloride

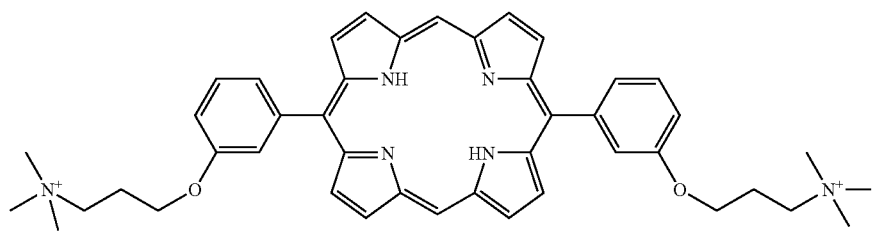

A solution of Compound 11 (400 mg, 0.543 mmol) in DMF (50 mL) is transferred into a 100 mL autoclave. After addition of trimethylamine (6.3 g), the mixture is stirred at 50° C. for 8 h. After evaporation of the solvent under reduced pressure, the residue obtained is dissolved in methanol (5 mL) and the solution is filtered through a pad of silica gel (depth 2 cm) supported on a steel frit (diameter 3.5 cm). After washing the pad with methanol (ca. 1 L), elution with acetic acid:methanol:water (3:2:1, by vol.) affords fractions which, after evaporation of the solvent under reduced pressure, gives a solid residue. This dissolved in methanol (5 mL) and purified by chromatography on a column (2.5×40 cm) of Sephadex LH-20 eluting with n-butanol:water:acetic acid (4:5:1, by vol., upper phase). Two fractions are eluted from the column, the first of which is the desired product. After removal of the solvent under reduced pressure, the residue obtained is dissolved in methanol (5 mL). The solution is passed through a short column (3.5×20 cm) of anion exchange resin(Amberlite IRA 400, chloride form), the solvent is removed under reduced pressure and the raw product is crystallised from methanol:diethylether to give violet crystals which are dried under high vacuum.

$^1$H-NMR: $\delta_H$ (300 Mz, CD$_3$OD): 2.30-2.35 (m, 4 H), 3.15 (s, 18 H), 3.95-5.05 (m, 4 H), 4.20-4.25 (m, 4 H), 7.40-7.45, 7.65-7.70, 7.80-7.85 (3×m, 8 H), 9.00-9.05, 9.40-9.45, (2×m, 8 H), 10.40 (m, 2 H).

COMPOUND 13

5,15-bis-(4-Hydroxy-phenyl)-10,20-bis-(4-undecyloxy-phenyl)-porphyrin

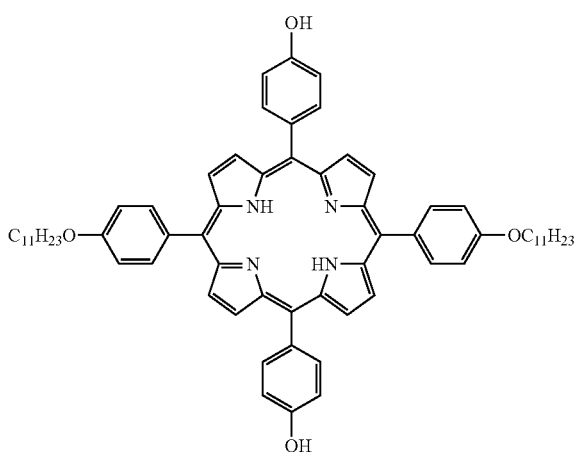

The third fraction eluted from the column during the chromatographic separation described for the synthesis of Compound 2 is characterised as 5,15-bis-(4-hydroxy-phenyl)-10,20-bis-(4-undecyloxy-phenyl)-porphyrin.

$^1$H-NMR: $\delta_H$ (300 MHz, CDCl$_3$): −2.88 (2 H, s) 0.85 (t, $^3$J 7.5 Hz, 6 H), 1.20-1.40 (m, 28 H), 1.55 (br m, 4 H), 1.80 (quint, $^3$J 7.5 Hz, 4 H), 4.15 (t, $^3$J 7.5 Hz, 4 H), 6.65, 7.15 (d, $^3$J 8.1 Hz, 8 H), 7.80, 8.00 (d, $^3$J 8.1 Hz, 8 H), 8.75-8.80 (m, 8 H).

trans-Regioisomer geometry is assigned by $^1$H—$^{13}$C-2D-NMR in d-acetic acid.

COMPOUND 14

5,10-bis-(4-Hydroxy-phenyl)-15,20-bis-(4-undecyloxy-phenyl)-porphyrin

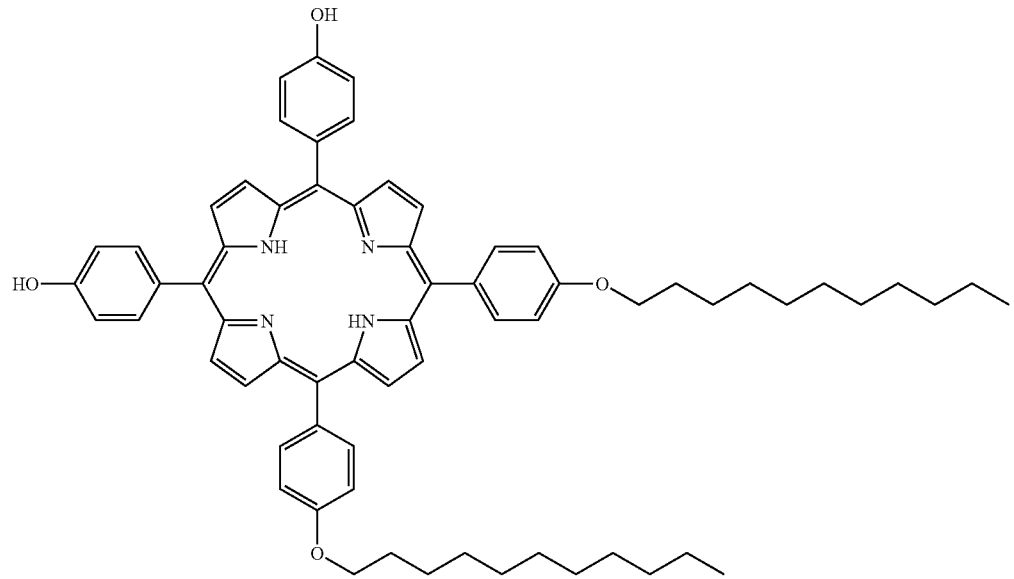

The fourth fraction eluted from the column during the chromatographic separation described for the synthesis of Compound 2 is characterised as 5,10-bis-(4-hydroxyphenyl)-15,20-bis-(4-undecyloxy-phenyl)-porphyrin $^1$H-NMR $\delta_H$ (300 MHz, CDCl$_3$): −2.80 (2 H, s), 0.90 (t, $^3$J 7.5 Hz, 6 H), 1.20-1.60 (m, 28 H), 1.65 (quint, $^3$J 7.5 Hz, 4 H), 2.00 (quint, $^3$J 7.5 Hz, 4 H), 4.22 (t, $^3$J 7.5 Hz, 4 H), 7.15 (d, $^3$J 8.1 Hz, 4 H), 7.25 (d, $^3$J 8.2 Hz, 4 H), 8.10 (d, $^3$J 8.2 Hz, 4 H), 8.15 (d, $^3$J 8.2 Hz, 4 H), 8.80-8.90 (m, 8 H).

cis-Regioisomer geometry is assigned by $^1$H—$^{13}$C-2D-NMR in d-acetic acid.

COMPOUND 15

5,10,15-tris-[4-(3-Bromo-propyloxy)-phenyl]-20-(4-undecyloxy-phenyl)-porphyrin

Under an argon atmosphere, Compound 2 (200 mg, 0.24 mmol) is dissolved in absolute DMF (40 mL) in the presence of K$_2$CO$_3$ (500 mg) and 1,3-dibromopropane (1.02 mL, 10 mmol). The mixture is heated overnight at 80° C. Work-ups is as the procedure given for Compound 2 described above. The product is purified by column chromatography on silica gel (Merck 60) eluting with hexane:ethyl acetate (5:1, by vol.).

$^1$H-NMR: $\delta_H$ (300 MHz, CDCl$_3$): −2.75 (2 H, s), 0.85 (t, $^3$J 7.5 Hz, 3 H), 1.20-1.45 (m, 14 H), 1.50 (quint, $^3$J 7.5 Hz, 2 H), 1.90 (quint, $^3$J 7.5 Hz, 2 H), 2.40 (quint, $^3$J 7.4 Hz, 6 H), 3.65 (t, $^3$J 7.4 Hz, 6 H), 4.16 (t, $^3$J 7.5 Hz, 2 H), 4.25 (t, $^3$J 7.5 Hz, 6 H), 7.18-7.20 (m, 8 H), 8.00-8.05 (m, 8 H), 8.75-8.85 (m, 8 H).

COMPOUND 16

5,10,15-tris-[4-(3-Triethylammonio-propyloxy)-phenyl]-20-(4-undecyloxy-phenyl)-porphyrin trichloride

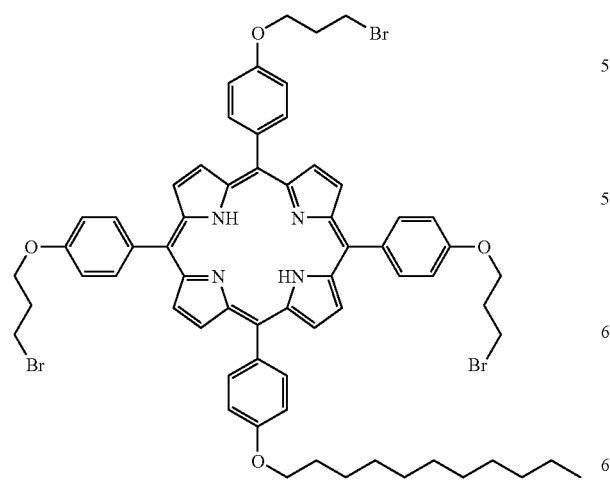

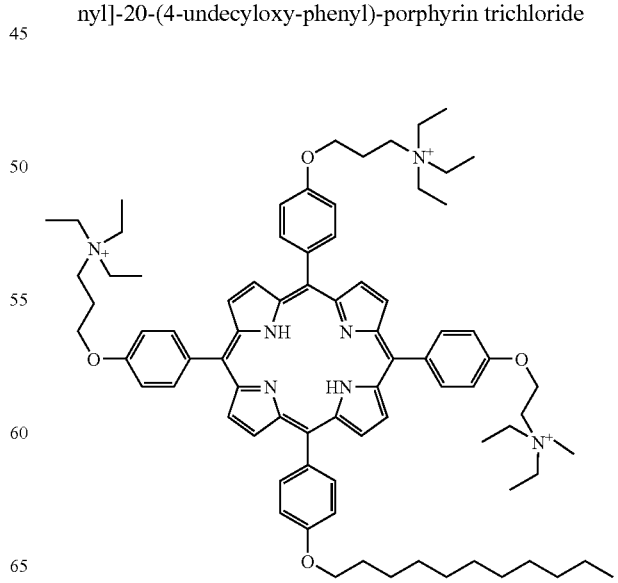

Compound 15 (200 mg, 0.17 mmol) is dissolved in absolute DMF (40 mL) with triethylamine (5 mL, 34.5 mmol, 208 eq.). The mixture is heated to 50° C. for 48 h. After removal of DMF under vacuum, the residue obtained is dissolved in methanol and purified by column chromatography using silica gel (Merck, 60) eluting with methanol:water:acetic acid (2:1:3, by vol.) and then acetic acid:pyridine (1:1, by vol.). Removal of solvent from appropriate fractions under vacuum affords raw product which is dissolved in methanol:aqueous NaCl (1M) (5 mL, 1:1, by vol.). The mixture is stirred for 30 mins and filtered through a pad of silica gel (depth 2 cm) supported on a steel frit (diameter 3.5 cm). After washing the pad with methanol (200 mL) it is eluted with methanol:water: acetic acid (2:1:3, by vol.). After evaporation of solvent from appropriate combined fractions, the residue obtained is dissolved in methanol (2 mL) and dichloromethane (5 mL) is added dropwise. The precipitated white gel is collected by filtration and the solvent is removed under high vacuum.

$^1$H-NMR: $\delta_H$ (300 MHz, CD$_3$OD): 0.90 (t, $^3$J 7.5 Hz, 3 H), 1.20-1.45 (m, 43H), 1.45-1.65 (bs, 2 H), 2.25-2.40 (bs, 6 H), 3.35-3.45 (bs, 24 H), 3.50-3.60 (bs, 6 H), 4.25 (t, $^3$J 7.5 Hz, 2 H), 4.40-4.45 (bs, 6 H), 7.25-7.40, 8.10-8.20 (m, 16 H), 8.80-9.10 (bs, 8 H).

COMPOUND 17

5-[4-(3-Hydroxy-phenyl)]-15-(3-undecyloxy-phenyl)-porphyrin 5-15-bis-(3Hydroxy-phenyl)-porphyrin (Wiehe, A., Simonenko, E. J., Senge, M. O. and Roeder, B. *Journal of Porphyrins and Phthalocyanines* 5, 758-761 (2001)) (86 mg, 0.17 mmol) is dissolved and K$_2$CO$_3$ (250 mg, 7.1 mmol) is suspended in DMF (40 mL). To the vigorously-stirred mixture a solution of 1-bromoundecane (0.04 mL, 0.17 mmol) in DMF (5 mL) is added dropwise at 50° C. during 30 mins and the mixture is heated at the temperature for 1 h. After removal by filtration of K$_2$CO$_3$, DMF is removed under high vacuum. The residue obtained is purified by column chromatography using silica gel (Merck 60) eluting with n-hexane:ethyl acetate (10:1, by vol.). The 2nd fraction is collected and dried under high vacuum to give the product.

$^1$H-NMR: $\delta_H$ (300 Mz, CDCl$_3$); −3.15 (2 H), 0.75 (t, $^3$J 7.5 Hz, 3 H), 1.10-1.30 (m, 14 H, 1.35 (m, 2 H), 1.80 (quint, $^3$J 7.5 Hz, 2 H), 4.05 (t, $^3$J 7.5 Hz, 2 H), 6.85-6.90, 7.20-7.25, 7.35-7.45, 7.50-7,65, 7.75-7.80 (5×m, 8 H), 8.85, 8.95, 9.10, 9.20 (4×dm $^3$J 4.9 Hz, 4×2 H), 10.15 (s, 2 H).

COMPOUND 18

5,10,15-tris-(3-Hydroxy-phenyl)-20-(3-dodecyloxy-phenyl)-porphyrin

3-Hydroxybenzaldehyde (1.8 g, 14.8 mmol, 3 equiv.) and 3-dodecyloxybenzaldehyde (1.35 g, 4.9 mmol, 1 eqv.) are dissolved in a mixture of acetic acid (145 mL) and nitrobenzene (98 mL, 960 mmol) and heated to 120° C. Pyrrole (1.35 mL, 19.6 mmol, 4 eqv.) is added in one portion and the mixture is stirred at 120° C. for 1 h. After cooling to room temperature, solvents are removed in vacuo at 50° C. The product is isolated by chromatography on a column (500 g) of silica using toluene as eluent. The desired product is obtained as the fifth fraction from the column and is re-chromatographed using a smaller (200 g) silica coulmn eluted with toluene. The product is obtained as a violet solid after evaporation of the solvent.

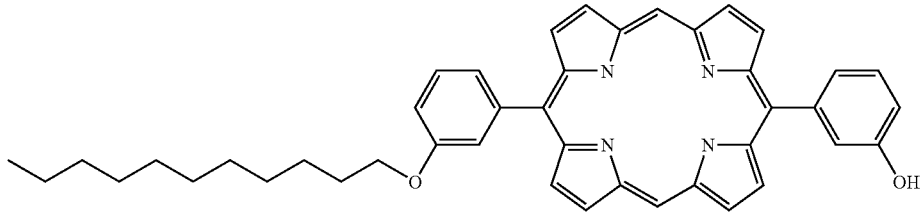

$^1$H-NMR: $\delta_H$ (300 MHz, CDCl$_3$): 0.64 (t, 3 H, $^3$J 6.8 Hz), 0.94-1.15 (m, 16 H), 1.25 (bs, 2 H), 1.62 (bs, 2 H), 3.90 (bs, 2 H), 6.33-6.95 (m, 8 H), 7.08-7.60 (m, 8 H), 8.02-8.47 (m, 4 H), 8.51-8.70 (m, 4 H)

COMPOUND 19

5-{3-[bis-(2-Diethylamino-ethyl)-aminopropyloxy]-phenyl}-15-(3-undecyloxy-phenyl)-porphyrin

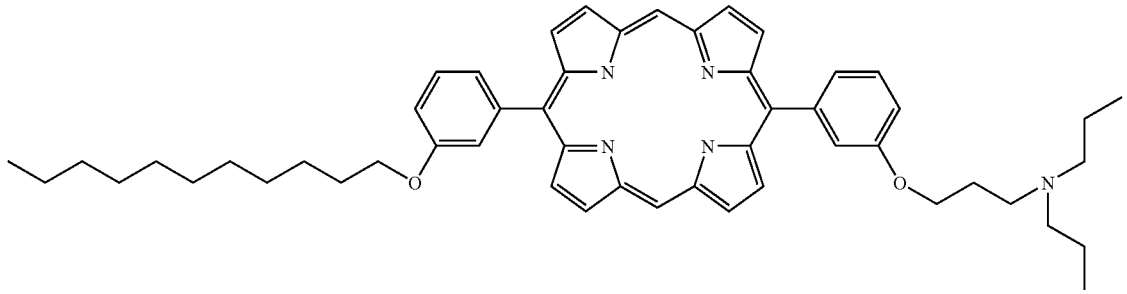

Compound 17 (50 mg, 0.065 mmol) is dissolved with N,N,N',N'-tetraethyldiethylenetriamine (1 mL, 39 mmol) in THF (10 mL) and the mixture is stirred at room temperature for 4 days. After evaporation of the solvent, the residue is dissolved in diethyl ether (20 mL) and the solution is washed with water (5×30 mL). The organic phase is dried (Na$_2$SO$_4$) and concentrated under high vacuum. The mixture is purified by column chromatography (silica gel, Merck 60) eluting with n-hexane:ethyl acetate (5:1, by vol.) followed by n-hexane:ethyl acetate:triethyl amine (10:10:1, by vol.). After collection of appropriate fractions and removal of solvent under reduced pressure, pure product is obtained by crystallisation of the residue from diethyl ether:methanol.

$^1$H-NMR: $\delta_H$ (300 Mz, CDCl$_3$): 0.80 (t, $^3$J 7.5 Hz, 3 H), 0.9 (t, $^3$J 7.5 Hz, 12 H), 1.20-1.40 (m, 14 H), 1.45 (quint, $^3$J 7.5 Hz, 2 H), 1.80 (quint, $^3$J 7.5 Hz, 2 H), 1.95 (quint, $^3$J 7.5 Hz, 2 H), 2.40-2.60 (m, 16 H), 2.65 (t, $^3$J 7.5 Hz, 2 H), 4.10 (t, $^3$J 7.5 Hz, 2 H), 4.20 (t, $^3$J 7.5 Hz, 2 H), 7.30-7.40, 7.55-7.65, 7.75-7.80 (333 m, 8 H), 910-9.15, 9.20-9.25 (2×m, 2×4 H), 10.15 (s, 2 H).

COMPOUND 20

5-[4-(3-Bromo-propyloxy)-phenyl]-15-(4-dodecyloxy-phenyl)-porphyrin

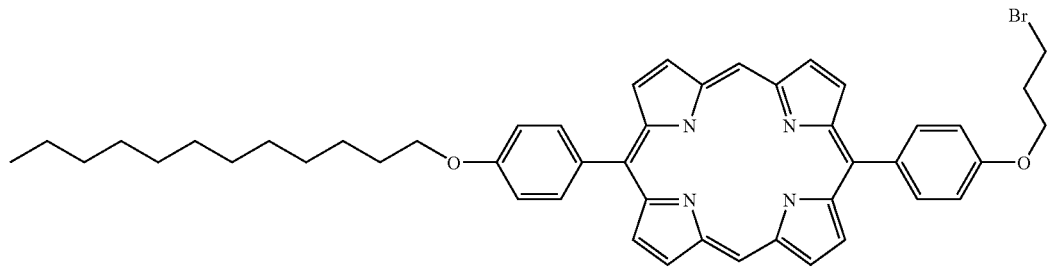

To a stirred solution of dipyrrolemethane (0.31 g, 2.1 mmol), 4-3-bromo-proyloxy)-benzaldehyde (0.27 g, 1.1 mmol) and 4-dodecyloxy-benzaldehyde (0.32 g, 1.1 mmol) in degassed dichloromethane (500 mL) TFA (0.035 mL, 1.5 mmol) is added dropwise. The solution is stirred at room temperature in the dark for 17 h under argon. After addition of DDQ (1.38 g, 6 mmol), the mixture is stirred at room temperature for a further hour. Purification by column chromatography using silica gel (Merck 60, 400 g) with toluene as eluent affords the product (2$^{nd}$ fraction) together with Compound 7 (3$^{rd}$ fraction).

$^1$H-NMR: $\delta_H$ (300 Mz, CDCl$_3$): −3.15 (2 H), s), 0.09 (t, $^3$J 7.5 Hz, 3 H), 1.20-1.40 (m, 16 H), 1.55 (quint, $^3$J 7.5 Hz, 2 H), 1.90 (quint, $^3$J 7.5 Hz, 2 H), 2.40 (quint, $^3$J 7.5 Hz, 2 H), 7.20-7.30, 8.10-8.15 (2×m, 8 H), 9.10-9.15, 9.25-9.30 (2×m, 2×4 H), 10.20 (s, 2 H).

COMPOUND 21

5,10,15,20-tetrakis-(3-Hydroxy-phenyl)-porphyrin

3-Hydroxybenzaldehyde (0.910 g, 7.45 mmol) is dissolved in propionic acid (50 mL) and heated to 140° C. Pyrrole (0.52 mL, 7.45 mmol) is added in one portion and the mixture heated at reflux for 2 h. Stirring is continued for an additional 12 h at room temperature. Propionic acid is removed in vacuo and the residue dissolved in acetone and purified by chromatography on a column (250 g) of silica which is eluted with toluene containing a continuously increasing proportion of ethyl acetate. The product is eluted with toluene:ethyl acetate (6:1 by vol.). Solvent is removed in vacuo to afford the product as a violet solid.

$^1$H-NMR: $\delta_H$ (300 MHz, d6-acetone): 7.18 (d, 4H, $^3$J=8.25 Hz), 7.49 (t, 4H), $^3$J–8.25 Hz), 7.56-7.62 (m, 8H), 8.81 (m, 8 H)

COMPOUND 22

5,10,15-tris-[4-(3-Bromo-propyloxy)-phenyl]-20-(4-dodecyloxy-phenyl)-porphyrin

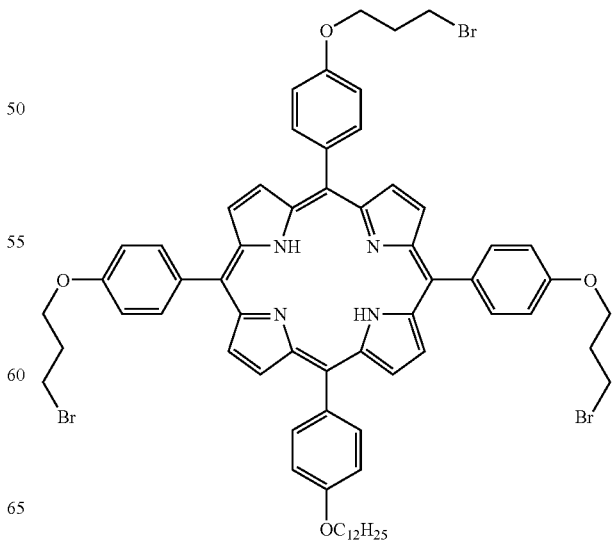

To a stirred solution of pyrrole (0.7 ml, 10 mmol), 4-(3-bromoproyloxy)-benzaldehyde (1.8 g, 7.5 mmol) and 4-n-dodecyloxy)-benzaldehyde(0.725 g, 2.5 mmol) in degassed dichloromehtane (1 L) is added TFA (0.085 ml, 10 mmol) dropwise. The reaction solution is stirred under argon at room temperature in the dark for 17 h. After addition of DDQ (6.9 g, 30 mmol), the reaction mixture is stirred at room temperature for a further 1 h. The solvents are removed under reduced pressure and the residue re-dissolved in toluene. Chromatographic purification on a column (3.5×30 cm) of silica gel (Merck 60) using toluene:n-hexane (1:4 by vol.) as eluent gives crude product which is purified by recrystallisation from methanol:dichloromethane, giving violet crystals.

$^1$H-NMR: $\delta_H$ (300 MHz, CDCl$_3$): 0.90 (t, $^3$J 7.5 Hz, 3 H), 1.20-1.45 (m, 16 H), 1.60 (quint, $^3$J 7.5 Hz, 2 H), 1.90 (quint, $^3$J 7.5 Hz, 2 H), 2.50 (quint, $^3$J 7.4 Hz, 6 H), 3.75 (t, $^3$J 7.4 Hz, 6 H), 4.20 (t, $^3$J 7.5 Hz, 2 H), 4.35 (t, $^3$J 7.5 Hz, 6 H), 7.25-7.30 (m, 8 H), 8.15-8.30 (m, 8 H), 8.80-8.85 (m, 8 H).

COMPOUND 23

5-{4-[3-Dimethyl-(3-dimethylaminopropyl)-ammonio-propyloxy]phenyl}-15-(4-dodecyloxy-phenyl)-porphyrin chloride

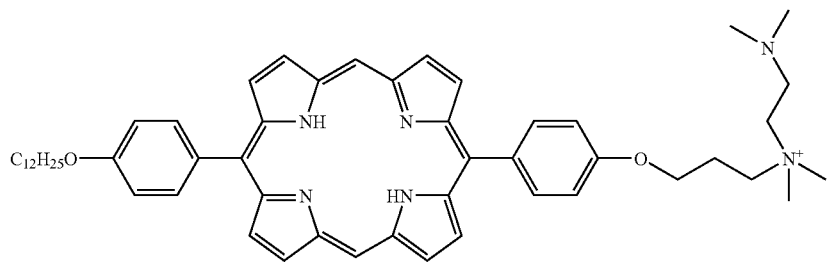

Compound 20 (30 mg, 0.038 mmol) is dissolved with N,N,N',N'-tetramethyl-1,3-propanediamine (156 mg, 1.2 mmol) in THF:DMF(1:1 by vol., 20 mL) and stirred at 50° C. for 18 h. After evaporation of the solvent under reduced pressure, the residue is dissolved in dichloromethane and purified by column chromatography (silica gel Merck 60) eluting with acetic acid:methanol:water (3:2:1, by vol.). After combining appropriate fractions and removal of solvent under reduced pressure, the residue is crystallised from dichloromethane:hexane to afford the product as violet crystals.

$^1$H-NMR: $\delta_H$ (300 Mz, CDCl$_3$1% acetic acid): 0.85 (m, 3 H), 1.20-1.40 (m, 18 H), 1.55-1.60 (m, 2 H), 1.60-1.65 (m, 4H), 2.10-2.20 (bs, 8 H), 3.15-3.25 (m, 8 H), 3.75 (bs, 2 H), 4.20 (bs, 2 H), 4.35 (bs, 2 H), 7.15-7.20, 8.10-8.15 (2×m, 8 H), 8.95-9.00, 9.10-9.25-9.30 (3×bs, 8 H), 10.20 (s, 2H).

COMPOUND 24

5,15-bis-(3-Methoxy-phenyl)-10-undecyl-porphyrin

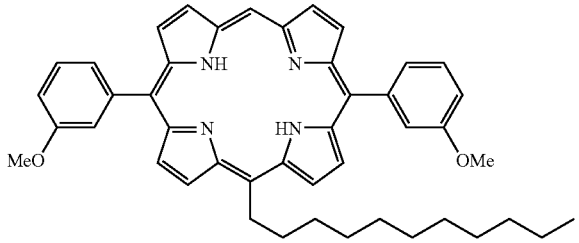

Into a 50 mL flask containing lithium (500 mg, 71 mmol) is added freshly distilled diethyl ether (15 mL) under an argon atmosphere. The suspension is refluxed for 1 hour, cooled to 15° C. and treated with a solution of a n-undecylbromide (6.58 g, 71 mmol) in ether (6 mL) added dropwise via syringe. The mixture is cooled to 7-10° C. and, after 5 min, when the suspension becomes slightly cloudy and bright spots appear on the lithium metal, the remainder of the n-undecylbromide solution is added at an even rate over a period of 30 min while the internal temperature is maintained at below 10° C. Upon completion of addition, the mixture is stirred further for 1 h at 10° C. The suspension is filtered under argon to remove excess lithium and lithium bromide.

5,15-bis-(3-Methoxy-phenyl)-porphyrin (100 mg, 0.19 mmol) is dissolved in anhydrous THF (30 mL at −50° C. under an argon atmosphere. The organolithium reagent described above (5 mL) is added dropwise to the mixture. After 5 min the cooling bath is removed and the mixture is warmed to room temperature. After stirring at room temperature for 15 min the reaction is quenched by slow addition of water (2 mL). After 15 min the mixture is oxidized by the addition of DDQ (4 mL, 0.4 mmol, 0.1 M in THF) and stirred for a further 15 min. The mixture is filtered through alumna (neutral, Brockman grade+) and purified by column chromatography on silica gel eluting with hexane:dichloromethane (4:1 by vol.) The first fraction is collected and crystallised from methanol:dichloromethane.

$^1$H-NMR: $\delta_H$ (300 Mz, CDCl$_3$): −3.05 (bs, 2 H), 0.80 (t, $^3$J 7.5 Hz, 3 H), 1.10-1.20 (m, 12 H), 1.25 (m, 2 H), 1.70 (quint, $^3$J 7.5 Hz, 2 H), 2.40 (quint, $^3$J 7.5 Hz, 2 H), 3.85 (s, 6H), 4.95 (t, $^3$J 7.5 Hz, 2 H), 7.20-7.23, 7.50-7.60, 7.65-7.75 (3×m, 8 H), 8.85-8.90, 9.10-9.15, 9.35-9.40 (3×m, 8 H), 9.95 (s, 1H).

COMPOUND 25

3-[({3-[(3-{4-[15-(4-Dodecyloxy-phenyl)-porphyrin-5-yl]-phenoxy}-propyl)-dimethyl-ammonio]-propyl}-dimethyl-ammonio)-propyl]-trimethyl-ammonium trichloride

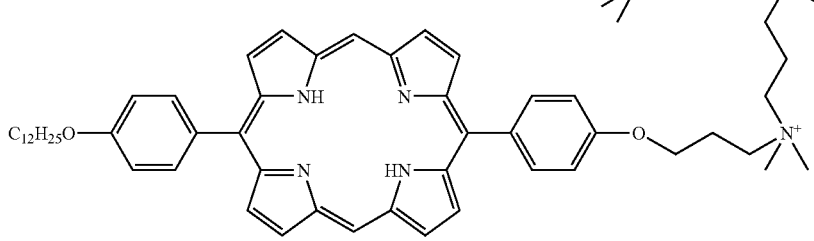
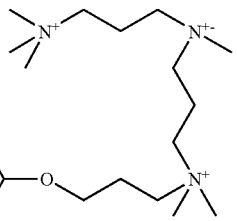

Compound 23 (20 mg, 0.022 mmol) and (1-bromopropyl)-trimethyl-ammonium bromide (26 mg, 0.1 mmol) are dissolved in DMP(15 ml) and stirred overnight at 50° C. After evaporation of the solvent under reduced pressure, the residue is dissolved in methanol (5 ml) and applied to a pad (3 cm deep) of silica gel which is washed with methanol (500 ml) followed by acetic acid:methanol:water (3:2:1 by vol.). After evaporation of the solvent the residue is purified by column chromatography (silica gel Merck 60) using at first acetic acid:methanol:water (3:2:1 by vol.) and then pyridine:acetic acid (1:1 by vol.). The second fraction eluted is collected and dried under vacuum. The residue is dissolved in methanol (2 ml) and purified by chromatography on a column (2.5×40 cm) of Sephadex LH-20 which is eluted with n-butanol:acetic acid: water (5:1:4 by vol., upper phase). After removal of solvent under reduced pressure, the residue is dried under vacuum at 80° C. NMR spectroscopy indicates the product is contaminated with a small proportion of elimination products.

COMPOUND 26

5,10,15-bis-[4-(3-Diethylamino-propyloxy)-phenyl]-20-(4-dodecyloxy-phenyl)-porphyrin

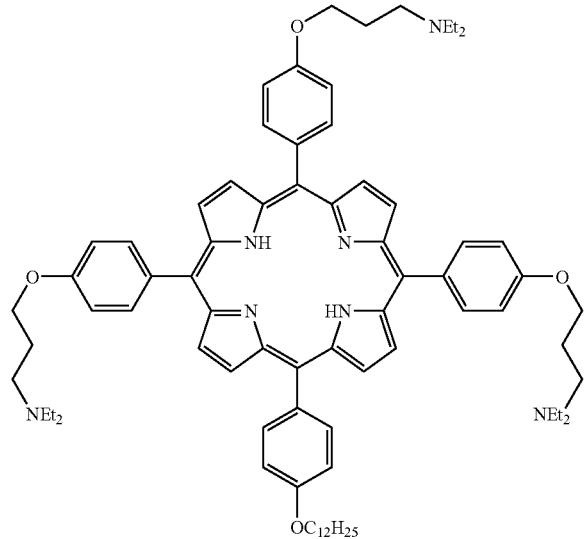

Compound 22 (50 mg, 0.06 mmol) and freshly distilled diethylamine (5 ml) are dissolved in absolute DMF (30 ml) under argon. The reaction mixture is stirred at room temperature for 20 h and poured into ethyl acetate (50 ml). The mixture is washed with water (4×50 ml) and, after drying the combined organic phases ($Na_1SO_4$), evaporation of solvent affords a residue which is purified by chromatography on a column (2.5×30 cm) of silica (Merck 60) which is eluted with ethyl acetate:hexane:triethyl amine (10:10:1, by vol.). Fractions are combined as appropriate, the solvent evaporated under reduced pressure and the residue dried under high vacuum. Recrystallisation from dichloromethane:n-hexane affords pure product.

$^1$H-NMR: $\delta_H$ (300 MHz, $CDCl_3$): 0.85 (t, $^3J$ 7.5 Hz, 3 H), 1.05 (m, 18 H), 1.20-1.45 (m, 18 H), 1.55 (quint, $^3J$ 7.5 Hz, 2 H), 2.15 (quint, $^3J$ 7.5 Hz, 6 H), 2.75 (quint, $^3J$ 7.4 Hz, 6 H), 3.15-3.25 (m, 12 H), 4.15 (t, $^3J$ 7.5 Hz, 2 H), 4.25 (t, $^3J$ 7.5 Hz, 6 H), 7.15-7.20 (m, 8 H), 8.00-8.05 (m, 8 H), 7.95-8.05 (m, 8 H).

COMPOUND 27

5,15-bis-(3-Hydroxy-phenyl)-10-undecyl-porphyrin

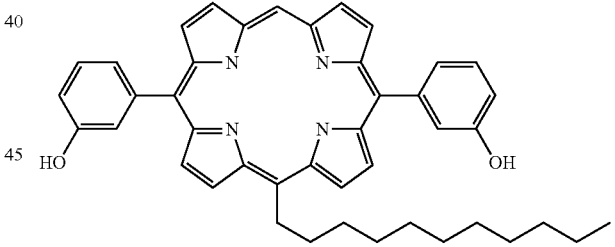

To a solution of Compound 24 (95 mg, 0.14 mmol) in anhydrous dichloromethane (80 mL) under an argon atmosphere $BBr_3$, (6 mL, 1M in dichloromethane) is added dropwise at −70° C. and the mixture is stirred for 1 h. The mixture is warmed to room temperature and stirred overnight then cooled to −10° C. and hydrolysed by addition of 2 mL water during 1 h. $NaHCO_3$ (3 g) is added directly to neutralisation. The mixture is stirred for a further 12 h. After removal of $NaHCO_3$ by filtration and of dichloromethane under vacuum, the residue obtained is purified by column chromatography using silica gel eluting with dichloromethane. After removal of solvent from appropriate combined fractions and drying under high vacuum the product is obtained as violet crystals.

$^1$H-NMR: $\delta_H$(300 Mz, $CDCl_3$): 3.05 (bs, 2 H, s) 0.85 (t, $^3J$ 7.5 Hz, 3 H), 1.20-1.40 (m, 12 H), 1.50 (m, 2 H), 1.80 (quint, $^3J$ 7.5 Hz, 2 H), 2.55 (quint, $^3J$ 7.5 Hz, 2 H), 5.00 (t, $^3J$ 7.5 Hz, 2 H), 7.15-7.25, 7.50-7.60, 7.80-7.90 (3×m, 8 H), 8.95-9.00, 9.20-9.25, 9.50-9.60 (3×m, 8 H), 10.15 (s, 1H).

45
COMPOUND 28

5,15-bis-[3-(3-Trimethylammmonio-proploxy)-phenyl]-10-undecyl-porphyrin dichloride

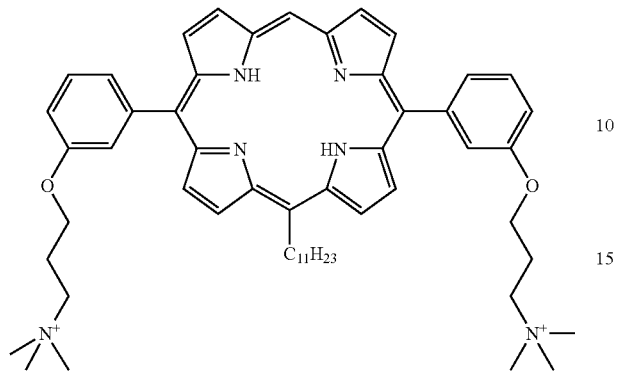

46
COMPOUND 29

5,10-bis-[4-(3-Trimethylammonio-propyloxy)-phenyl]-15,20-bis-(4-undecyloxy-phenyl)-porphyrin dichloride

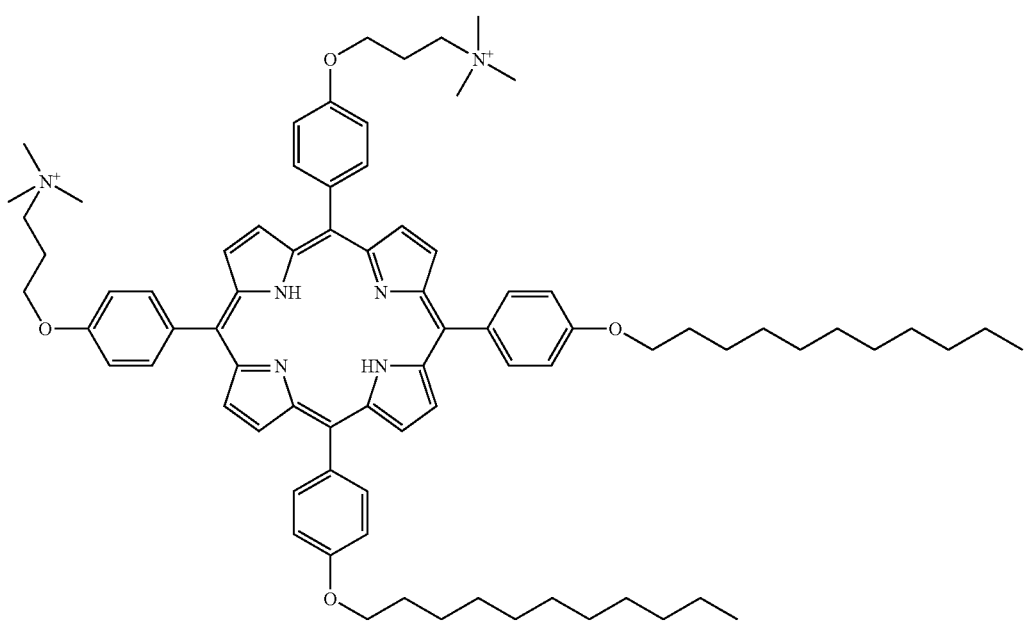

To a solution of Compound 27 (50 mg, 0.08 mmol) in DMF (20 mL) under an argon atmosphere $K_2CO_3$ (100 mg, 0.72 mmol) and (3-bromopropyl)-trimethlammonium bromide (300 mg, 1.2 mmol) are added and the mixture is stirred at 50° C. for 18 h. After removal of solvent under high vacuum the residue obtained is dissolved in methanol (5 mL) and filtered through a pad of silica gel (depth 2 cm) supported on a steel frit (diameter 3.5 cm). After washing the pad with methanol (500 mL) it is eluted with acetic acid:methanol:water (3:2:1, v:v). After drying of appropriate combined fractions under high vacuum the residue is dissolved in methanol and purified by column chromatography on Sephadex LH-20 eluting with n-butanol:acetic acid:water (5:1:4, by vol., upper phase). After evaporation of solvent the residue obtained from the first fraction eluted is dissolved in methanol and passed through a short column of anion exchange resin (Amberlite IRA 400, chloride form) to give, after evaporation of solvent, the pure product.

$^1$H-NMR: $\delta_H$ (300 Mz, $CD_3OD$): 0.85 (t, $^3J$ 7.5 Hz, 3 H), 1.20-1.40 (m, 12 H), 1.50 (m, 2 H), 1.80 (m, 2 H), 2.40 (bs, 4 H), 2.55 (m, 2 H), 3.20 (bs, 18 H), 3.65 (bs, 4 H), 4.35 (bs, 4 H), 5.10 (m, 2 H), 7.50-7.55, 7.70-7.85 (2×m, 8 H), 8.95-9.00, 9.25-9.24, 9.50-9.70 (3×bs, 8 H), 10.15 (bs, 1H).

Compound 14 (50 mg, 0.05 mmol) is dissolved and $K_2CO_3$ (150 mg, 1.1 mmol) is suspended in DMF (30 mL). To the vigorously-stirred mixture a solution of (1-bromopropyl)-trimethylammonium bromide (0.3 g, 16.6 mmol) in DMF (10 mL) is added dropwise at 50° C. and the mixture is heated for 18 h. After removal of DMF under high vacuum, the residue obtained is dissolved in methanol (5 mL) and filtered through a pad of silica gel (depth 2 cm) supported on a steel frit (diameter 3.5 cm). After washing the pad with methanol (ca. 500 mL) it is eluted with acetic acid:methanol:water (3:2:1, by vol.). After evaporation of solvent from appropriate combined fractions the residue obtained is purified by chromatography on a column (2.5×40 cm) of Sephadex LH-20 eluting with n-butanol:water:acetic acid (5:4:1, by vol., upper phase). After removal of solvent under reduced pressure the residue obtained is dissolved in methanol and passed through a short column (3.5×20 cm) of anion exchange resin (Amberlite IRA 400, chloride form). After evaporation of solvent under reduced pressure, the product is dried under high vacuum.

$^1$H-NMR: $\delta_H$ (300 MHz, $CD_3OD$): 0.80 (t, $^3J$ 7.5 Hz, 6 H), 1.15-1.35 (m, 28 H), 1.35-1.45 (bs, 4 H), 1.70-1.80 (bs, 4 H), 2.30-2.40 (bs, 4 H), 3.15-3.30 (bs, 18 H), 3.65-3.75 (bs, 4 H), 4.00-4.05 (m, 4 H), 4.30-4.40 (bs, 4 H), 7.00-7.15, 7.20-7.30, 7.80-95, 7.95-8.15 (4×m, 4×4 H), 8.60-9.00 (bs, 8 H).

COMPOUND 30

5,10,15-tris-(3-Hydroxy-phenyl)-20-(3-undecyloxy-phenyl)-porphyrin

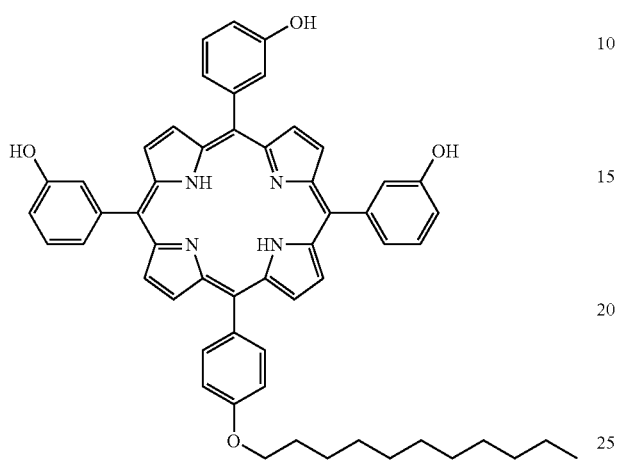

Pyrrole (1.31 g, 19.6 mmol) is added in one portion to a mixture of 3-hydroxybenzaldehyde (1.8 g, 14.8 mmol) in acetic acid (145 mL) and nitrobenzene (118 g, 960 mmol) preheated to 130° C. and the mixture is stirred for 1 hour at 120° C. The mixture is cooled and solvent removed under high vacuum. The residue is dissolved in dichloromethane (5 mL) and purified by column chromatography using silica gel (Merck 60) eluting with hexane:toluene (4:1, by vol.). The product is obtained after removal of solvent from the eluate under reduced pressure and drying the obtained residue under vacuum.

$^1$H-NMR: $\delta_H$ (300 Mz, CDCl$_3$): 0.75-0.80 (m, 3 H), 1.05-1.35 (m, 14 H), 1.40-1.50 (m, 2 H), 1.75-1.85 (m, 2 H), 3.90-4.10 (m, 2 H), 6.90-7.70 (m, 16 H), 8.45-8.80 (m, 8 H).

Compound 23 (50 mg, 0.055 mmol) is dissolved with methyl iodide (5 mL, 80 mmol) in absolute DMF(30 mL) and the mixture is stirred at 40° C. for 3 h. After evaporation of solvent the residue obtained is dissolved in methanol (5 mL) and filtered through a pad of silica gel (depth 2 cm) supported on a steel frit (diameter 3.5 cm). After washing the pad with methanol (ca. 1 L) it is eluted with dichloromethane:methanol (2:3 by vol., 500 mL) and then acetic acid:water:methanol (3:1:2, by vol.). After removal of solvent from appropriate pooled fractions the residue obtained is dissolved in acetic acid and purified by column chromatography on Sephadex LH-20 eluting with acetic acid. After evaporation of solvent from appropriate pooled fractions and drying the residue obtained under high vacuum, the residue is dissolved in methanol and passed through a small column (3.5×20 cm) of anion exchange resin (Amberlite IRA 400, chloride form). After evaporation of solvent from the eluate, the product is dried under high vacuum.

COMPOUND 31

5-{4-[3-Dimethyl-(3-trimethylammonio-propyl)-ammonio-propyloxy]-phenyl}-15-(4-dodecyloxy-phenyl)-porphyrin dichloride

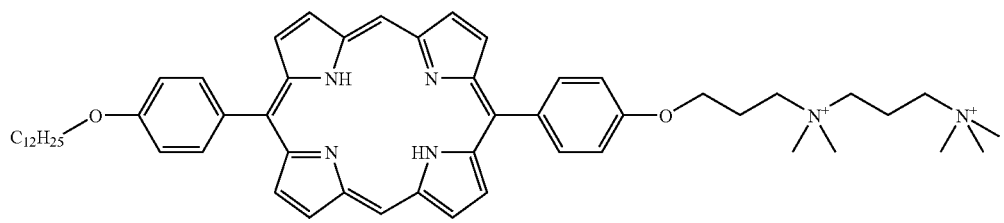

COMPOUND 32

5-[4-(3-Dimethyldecyl-ammoniopropyloxy)-phenyl]-15-{4-[3-dimethyl-(3-dimethylaminopropyl)-ammoniopropyloxy]-phenyl}-porphyrin dichloride

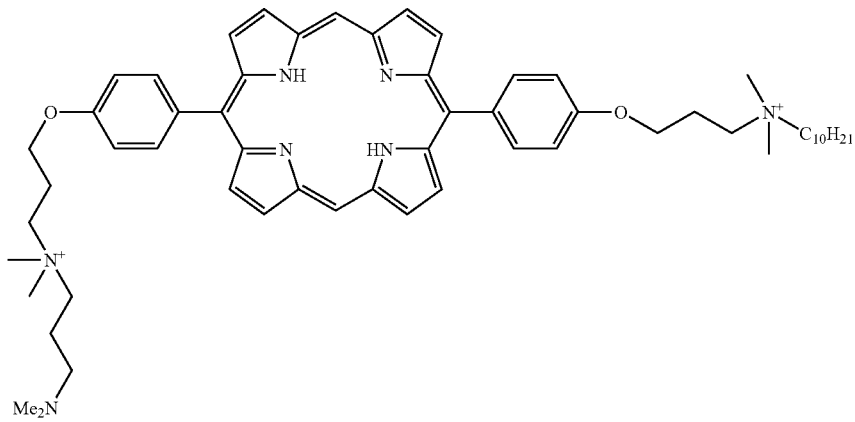

Compound 23 (50 mg, 0.068 mmol) is dissolved with N,N,N',N'-tetramethyl-1,3-propanediamine (354 mg, 1.36 mmol) and N,N-demethyldecylamine (1 g, 2.72 mmol) in DMF:THF(30 mL, 1:1, by vol.) and the mixture is stirred at 50° C. overnight. After evaporation of the solvent under reduced pressure the residue obtained is dissolved in methanol (10 mL) and filtered through a pad of silica gel (depth 2 cm) supported on a steel frit (diameter 3.5 cm). After washing the pad with methanol (ca. 500 mL) it is eluted with acetic acid:methanol:water (3:2:1, by vol.). The first two fractions eluted are combined and after evaporation of the solvent under reduced pressure the residue obtained is dissolved in methanol and purified by chromatography on a column (2.5× 40 cm) of Sephadex LH-20 eluting with n-butanol:water: acetic acid (4:5:1, by vol.). After removal of solvent under reduced pressure from the second fraction eluted, the residue is dissolved in methanol (5 mL) and passed through a short column (3.5×20 cm) of anion exchange resin (Amberlite IRA 400, chloride form). The eluate is evaporated to dryness and the residue obtained is dried under high vacuum to afford the product.

$^1$H-NMR: $\delta_H$ (300 MHz, CD$_3$OD): 0.80 (m, 3 H), 1.05-1.25 (m, 10 H), 1.25-1.40 (bs, 2 H), 1.80-1.90 (bs, 4 H), 2.15-2.30 (bs, 2 H), 2.80-3.60 (m, 20 H), 3.80-3.95 (bs, 4 H), 7.05-7.15, 7.85-8.00 (2×m, 2×4 H), 9.20-9.35 (2×bs, 2×4 H), 10.15 (bs, 2).

COMPOUND 33

5,10,15-tris[3-(3-Trimethyl-ammoniopropyloxy)-phenyl]-20-(3-undecyloxy-phenyl)-porphyrin trichloride

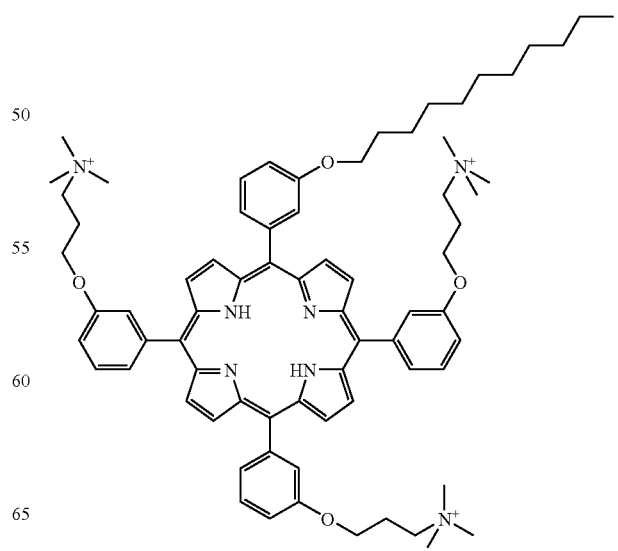

Compound 30 (100 mg, 0.12 mmol) is dissolved and K$_2$CO$_3$ (230 mg, 1.7 mmol) is suspended in DMF (30 mL). To the vigorously-stirred mixture a solution of (1-bromopropyl)-trimethylammonium bromide (0.3 g, 16.6 mmol) in DMF (10 mL) is added dropwise at 50° C. during 30 mins and the mixture is heated for 18 h. After removal of DMF under reduced pressure, the residue obtained is dissolved in methanol (5 mL) and filtered through a pad of silica gel (depth 2 cm) supported on a steel frit (diameter 3.5 cm). After washing the pad with methanol (ca. 500 mL) it is eluted with acetic acid:methanol:water (3:2:1, by vol.). After evaporation of solvent from appropriate combined fractions under reduced pressure, the residue is purified by chromatography on a column (2.5× 40 cm) of Sephadex LH-20 eluting with n-butanol:water:acetic acid (5:4:1, by vol., upper phase). After removal of solvent under reduced pressure from the eluate, the residue obtained is dissolved in methanol and the solution is passed through a short column (3.5×20 cm) of anion exchange resin (Amberlite IRA 400, chloride form). Evaporation of solvent from the eluate gives the product which is dried under high vacuum.

$^1$H-NMR: $\delta_H$ (300 MHz, CD$_3$OD): 0.75-0.80 (m, 3 H), 1.00-1.40 (m, 18 H), 1.60-1.80 (bs, 2 H), 2.25-2.40 (bs, 6 H), 3.29 (bs, 27 H), 3.40-3.60 (m, 6 H), 3.90-4.00 (m, 2 H), 4.05-4.25 (m, 6 H), 7.10-7.20, 7.25-7.40, 7.60-7.80, 7.80-7.90 (4×m, 16H), 8.70-9.00 (bs, 8).

COMPOUND 34

5,15bis-(3-Hydroxy-phenyl)-porphyrin

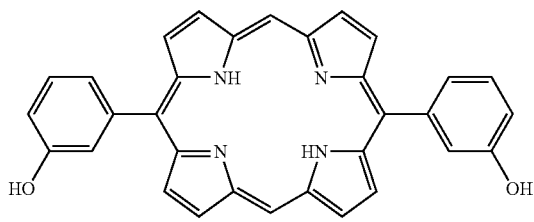

This is prepared as described by Wiehe, A., Simonenko, E. J., Senge, M. O. and Roeder, B. *Journal of Porphyrins and Phthalocyanines* 5, 758-761 (2001).

COMPOUND 35

5,10,15-tris-(4-Hydroxy-phenyl)-20-4-tetradecyloxy-phenyl)-porphyrin

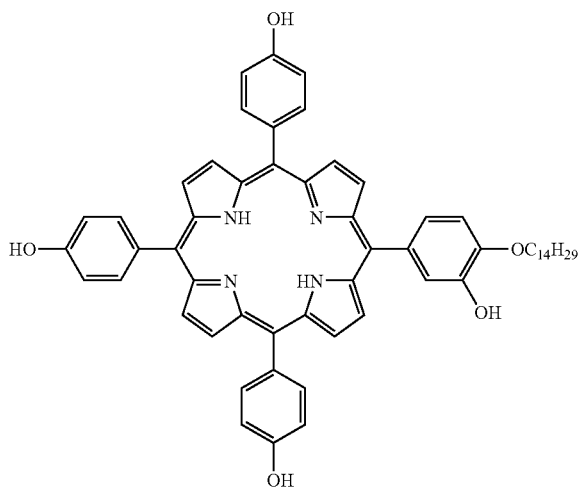

5,10,15,20-tetrakis-(4-Hydroxy-phenyl-porphyrin (170 mg, 0.25 mmol) is dissolved and K$_2$CO$_3$ (0.65 g, mmol) is suspended in DMF (30 mL). To the vigorously stirred reaction mixture a solution of 1-bromotetradecane (0.1 mL, 0.45 mmol) in DMF (10 mL) is added dropwise at 50° C. during 30 mins and the mixture is heated for 1.5 h. After evaporation of solvent, the residue is dissolved in toluene:ethanol (1:1 by vol., ca. 5 mL) and purified by chromatography using a column (5×25 cm) of silica gel (Merck 60) which is washed with toluene. After the elution of the first 3 fractions, elution is continued using toluene:ethyl acetate (2:1 by vol.). The fifth compound eluted is collected, the solvent evaporated and the residue dried under high vacuum to afford product as violet crystals.

$^1$H-NMR: $\delta_H$ (300 MHz, d6-acetone): 0.85 (t, $^3$J 7.5 Hz, 3 H), 1.15-1.55 (m, 20 H), 1.45 (quint, $^3$J 7.5 Hz, 2 H), 1.75 (quint, $^3$J 7.5 Hz, 2 H), 4.10 (t, $^3$J 7.5 Hz, 2 H), 7.20 (d, $^3$J 8.5 Hz, 2 H), 7.25 (d, $^3$J 8.5 Hz, 6 H), 8.00-8.15 (m, 8 H), 8.80-9.10 (m, 8 H).

COMPOUND 36

5,10,15-tris-[4-(3-Trimethyl-ammoniopropyloxy)-phenyl]-20-(4-tetradecyloxy-phenyl)-porphyrin trichloride

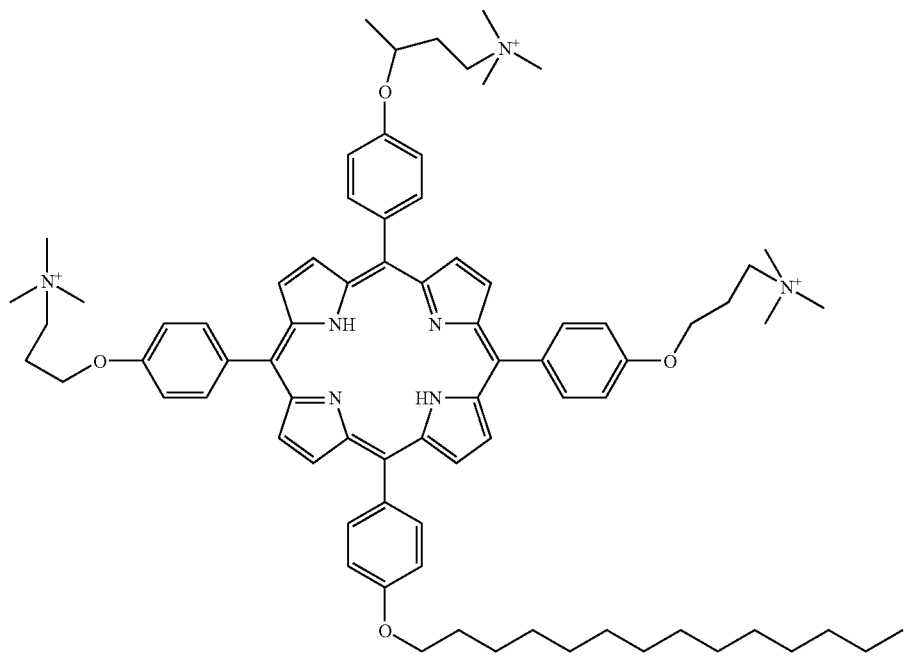

The n-tetradecyloxy-analogue of Compound 2, prepared similarly as described above for Compound 2 but using 1-bromotetradecane in place of 1-bromoundecane. (50 mg, 0.057 mmol) and (1-bromopropyl)-trimethylammonium bromide (210 mg, 0.8 mmol) are dissolved and $K_2CO_3$ (2.30 mg, 1.7 mmol) is suspended in DMF (20 mL). The vigorously stirred mixture is stirred at this temperature for 18 h. After removal of DMF under reduced pressure the residue obtained is dissolved in methanol (5 mL) and filtered through a pad of silica gel (depth 2 cm) supported on a steel frit (diameter 3.5 cm). After washing the pad with methanol (ca. 500 mL) it is eluted with acetic acid:methanol:water (3:2:1, by vol.). After evaporation of the solvent from appropriately combined fractions, the residue obtained is purified by chromatography on a column (2.5×40 cm) of Sephadex LH-20 eluting with n-butanol:water:acetic acid (4:5:1, by vol., upper phase) for separation from the excess of ammonium salt and other contaminating materials. After elution and removal of the solvent from appropriate fractions, the residue obtained is dissolved in methanol (5 mL) and passed through a short column (3.5×20 cm) of anion exchange resin(Amberlite IRA 400, chloride form). Solvent is removed under reduced pressure and the residue obtained is dried under high vacuum to afford the product as violet crystals.

$^1$H-NMR: $\delta_H$ (300 MHz, $CD_3OD$): 0.75 (t, $^3J$ 7.5 Hz, 3 H), 0.95-1.25 (m, 22 H), 1.50-1.65 (bs, 2 H), 2.20-2.40 (bs, 6 H), 3.05-3.15 (bs, 27 H), 3.45-3.60 (bs, 6 H), 3.60-3.80 (bs, 2 H), 4.05-4.25 (bs, 6 H), 6.80-7.25, 7.65-8.05, (2×m, 16H), 8.45-8.95 (bs, 8 H).

COMPOUND 37

5-(4-{3-[2,4,6-tris-(Dimethylaminomethyl)-phenyloxy]-propyloxy}-phenyl)-15-(4-dodecyloxy-phenyl)-porphyrin

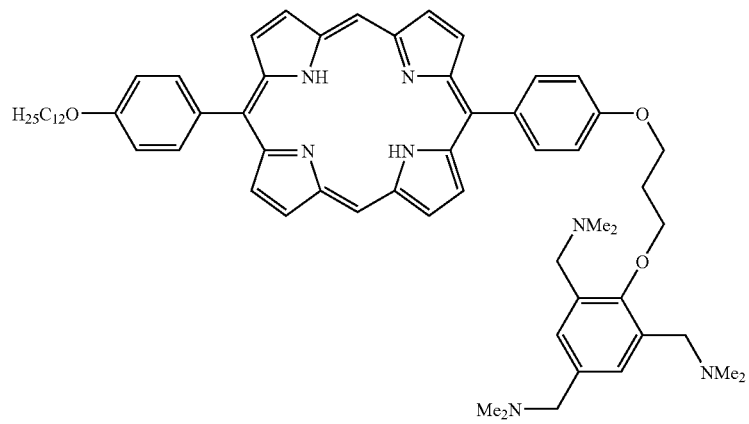

Compound 20 (50 mg, 0.063 mmol) is dissolved in DMF (20 mL) in the presence of 2,4,6-tris-(dimethylaminomethyl)-phenol (1 mL, 3.7 mmol) and stirred at 50° C. overnight. After evaporation of the solvent, the residue is crystallised from dichloromethane:methanol to remove the excess of amine. After filtration, the porphyrins are re-dissolved in dichloromethane and purified by chromatography of a column of silica gel (Merck 60) which is washed with dichloromethane. Evaporation of solvent under reduced pressure and recrystallisation of the residue from dichloromethane: methanol gives the product as violet crystals.

$^1$H-NMR: $\delta_H$ (300 Mz, CDCl$_3$): 3.15 (2 H), 0.85 (t, $^3$J 4.5 Hz, 3 H), 1.20-1.40 (m, 18 H), 1.55 (quint, $^3$J 4.5 Hz, 2 H), 1.90 (quint, $^3$J 4.5 Hz, 2 H), 2.20 (s, 18 H), 2.55 (t, $^3$J 5.2 Hz, 2 H), 3.45 (s, 6 H), 4.15 (t, $^3$J 5.5 Hz, 2 H), 4.20 (t, $^3$J 5.5 Hz, 2 H), 4.35 (t, $^3$J 7.5 Hz, 2 H), 6.85 (2×s, 2 H), 7.20-7.30, 8.10-8.15 (2×m, 8 H), 9.00-9.05, 9.25-9.30 (2×m, 2×4 H), 10.20 (s, 2 H).

pended in DMF (30 mL). To the vigorously stirred reaction mixture a solution of 1-bromodecane (0.016 mL, 0.11 mmol) in DMF (10 mL) is added dropwise at 70° C. during 30 mins and the mixture is stirred for 1.5 h. After evaporation of solvent, the residue is dissolved in toluene:ethanol (1:1 by vol., ca. 3 mL) and purified by chromatography on a column (150 g) of silica gel (Merck 60) using toluene as eluent. After elution of the first 3 fractions, the column is eluted with toluene:ethyl acetate (2:1 by vol.) and the 5$^{th}$ fraction eluted is collected, the solvent removed and the residue dried under high vacuum to give the product as violet crystals.

$^1$H-NMR: $\delta_H$ (300 Mz, d6-acetone): 0.95 (t, $^3$J 7.5 Hz, 3 H), 1.25-1.55 (m, 12 H), 1.55 (quint, $^3$J 7.5 Hz, 2 H), 1.85 (quint, $^3$J 7.5 Hz, 2 H), 4.15 (t, $^3$J 7.5 Hz, 2 H), 7.20 (d, $^3$J 8.5 Hz, 2 H), 7.25 (d, $^3$J 8.5 Hz, 6 H), 8.00-8.15 (m, 8 H), 8.80-9.10 (m, 8 H).

COMPOUND 38

5,10,15-tris-(4-Hydroxy-phenyl)-20-(4-decyloxy-phenyl)-porphyrin

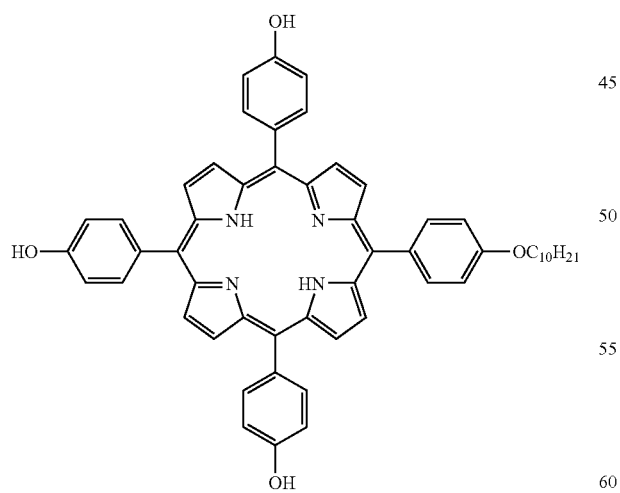

5,10,15,20-tetrakis-(4-Hydroxy-phenyl)-porphyrin (100 mg, 0.15 mmol) is dissolved and K$_2$CO$_3$ (230 mg) is sus-

COMPOUND 39

5,10,15-tris-[4-(3-Trimethylammonio-propyloxy)-phenyl]-20-(4-decyloxy-phenyl)-porphyrin trichloride

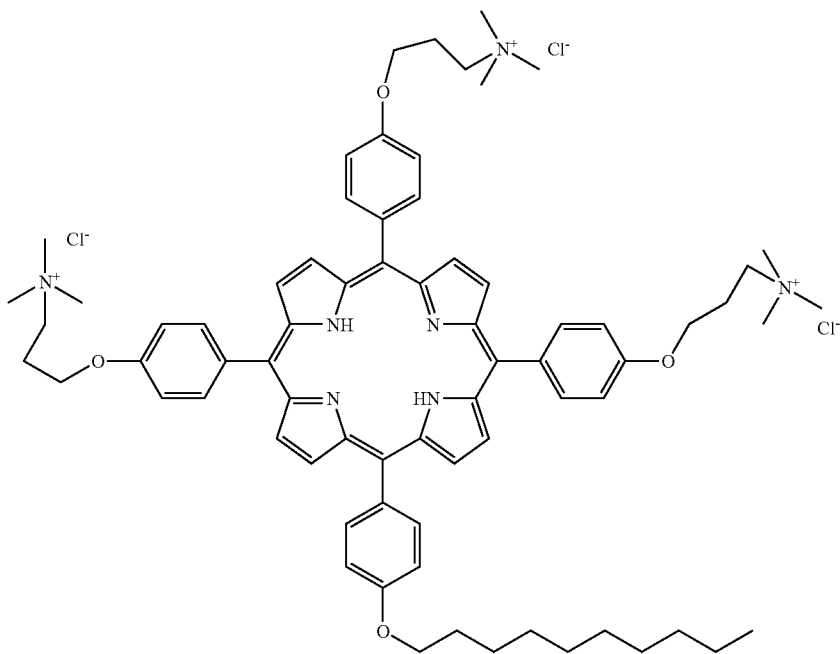

Compound 38 (50 mg, 0.061 mmol) and (1-bromopropyl)-trimethylammonium bromide (210 mg, 0.8 mmol) are dissolved and K$_2$CO$_3$ (230 mg, 1.7 mmol) is suspended in DMF (20 mL). The vigorously stirred reaction mixture is heated at 50° C. for 18 h. After evaporation of solvent, the raw product is dissolved in methanol and purified by chromatography on a column (2.5×40 cm) of Sephadex, eluting with n-butanol:water:acetic acid (4:5:1, by vol., upper phase). After removal of the solvent, the residue is dissolved in methanol and passed through a column (3.5×20 cm) of Amberlite IRA-400 (chloride form). After evaporation of solvent, the product is dried under high vacuum and yields violet crystals.

$^1$H-NMR: $\delta_H$ (300 MHz, CD$_3$OD): 0.90 (t, $^3$J 7.5 Hz, 3 H), 1.20-1.40 (m, 12 H), 1.45-1.60 (bs, 2 H), 1.80-1.90 (bs, 2 H), 2.45-2.55 (bs, 6 H), 3.25-3.35 (bs, 27 H), 3.75-3.85 (bs, 6 H), 4.05-4.25 (m, 2 H), 4.35-4.40 (bs, 6 H), 7.10-7.40, 7.95-8.15 (2×m, 16 H), 8.60-9.00 (bs, 8 H).

COMPOUND 40

5,10,15-tris-(4-Hydroxy-phenyl)-20-(4-tridecyloxy-phenyl)-porphyrin 5,10,15.20-tetrakis-(4-Hydroxy-phenyl)-porphyrin (400 mg, 0.59 mmol) is dissolved and K$_2$CO$_3$ (1.0 g, 7.1 mmol) is suspended in DMF (75 mL). To the vigorously stirred reaction mixture a solution of 1-bromotridecane (0.1 mL, 0.45 mmol) in DMF (10 mL) is added dropwise at 50° C. during 30 mins and the mixture is then heated for 1.5 h. The reaction mixture is cooled to room temperature and poured into water (150 mL). The porphyrins are extracted with ethyl acetate (100 mL) and the extract washed with brine (3×50 mL) and dried ($Na_2SO_4$). After evaporation of solvent, the residue is dissolved in toluene:ethanol (1:1, by vol., ca. 10 mL) and purified by chromatography using a column (200 g) of silica gel (Merck 60) with toluene as the eluent. After the elution of the first three compounds, the eluent is changed to toluene:ethyl acetate (2:1, by vol.). The fifth compound eluted is collected and dried under high vacuum to yield product as violet crystals.

$^1$H-NMR: $\delta_H$ (300 Mz, d6-acetone): 0.85 (t, $^3$J 7.5 Hz, 3 H), 1.20-1.60 (m, 18 H), 1.50 (quint, $^3$J 7.5 Hz, 2 H), 1.80 (quint, $^3$J 7.5 Hz, 2 H), 4.14 (t, $^3$J 7.5 Hz, 2 H), 7.20 (d, $^3$J 8.5 Hz, 2 H), 7.25 (d, $^3$J 8.5 Hz, 6 H), 8.00-8.15 (m, 8 H), 8.80-9.10 (m, 8 H).

COMPOUND 41

5-(4-Tridecyloxy-phenyl)-10,15,20-tris [4-(3-trimethylammonio-propyloxy)phenyl]-porphyrin trichloride Compound 40 (50 mg, 0.057 mmol) and (1-bromopropyl)-trimethylammonium bromide (210 mg, 0.8 mmol) are dissolved and $K_2CO_3$ (230 mg, 1.7 mmol is suspended in DMF (20 mL). The vigorously stirred reaction mixture is heated at 50° C. for 18 h. After removal of DMF, the residue is dissolved in methanol (5 mL) and applied to a pad (2 cm thick) of silica gel which is washed with methanol (ca. 1000 mL) and then eluted with acetic acid:methanol:water (3:2:1 by vol.). After evaporation of the solvent the residue is dissolved in methanol and further purified by chromatography on a column (2.5×40 cm) of Sephadex LH-20 which is eluted with n-butanol:water:acetic acid (4:5:1 by vol., upper phase). After removal of solvent, the residue is dissolved in methanol and passed through a short column (3.5×20 cm) of anion exchange resin (Amberlite IRC 400, chloride form). After evaporation of solvent, the product is dried under high vacuum to afford violet crystals.

$^1$H-NMR: $\delta_H$ (300 MHz, $CD_3OD$): 0.90 (t, $^3$J 7.5 Hz, 3 H), 1.20-1.40 (m, 18 H), 1.45-1.60 (m, 2 H), 1.80-1.90 (bs, 2 H), 2.40-2.55 (bs, 6 H), 3.25-3.35 (bs, 27 H), 3.75-3.85 (bs, 6 H), 4.05-4.25 (m, 2 H), 4.35-4.40 (bs, 6 H), 7.10-7.40, 7.90-8.15 (2×m, 16 H), 8.60-9.00 (bs, 8 H).

COMPOUND 42

5,15-bis-(4-Hydroxy-phenyl)-porphyrin

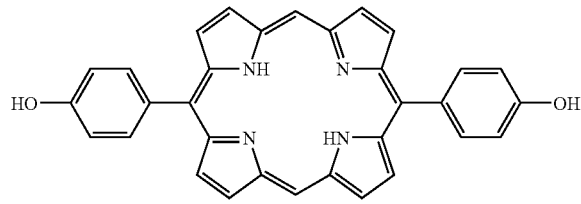

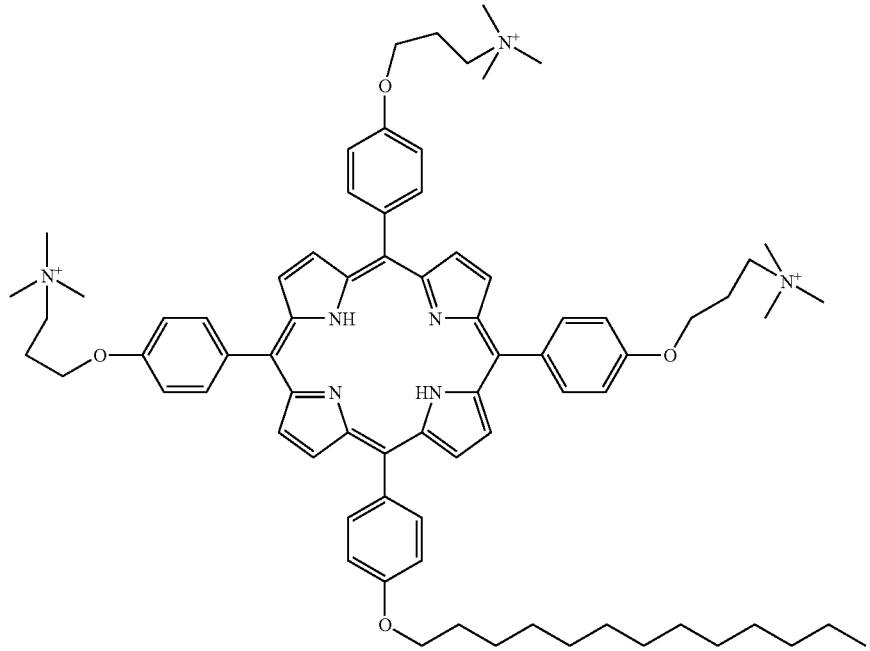

This is prepared as described by Mehta, Goverdhan; Muthusamy, Sengodagounder; Maiya, Bhasker G.; Arounaguiri, S., *J. Chem. Soc. Perkin Trans. I;* 2177-2182 (1999).

COMPOUND 43

5,10,15-tris-(4-Hydroxy-phenyl)-20-(4-octyloxyphenyl)-porphyrin

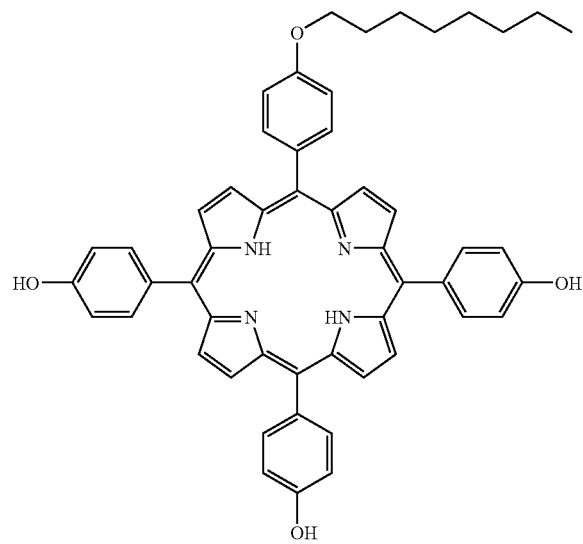

5,10,15,20-tetrakis-(4-Hydroxy-phenyl)-porphyrin (200 mg, 0.294 mmol) is dissolved and potassium carbonate (487 mg, 3.53 mmol, 12 eqv.) is suspended under argon in absolute DMF (50 mL) and the mixture is heated to 55° C. A solution of octyl bromide (35.8 µl, 0.206 mmol, 0.7 eqv.) in absolute DMF (10 mL) is added dropwise during 30 min. and the mixture is stirred at 55° C. for 2 h. The solvent is removed in vacuo at 50° C., water (80 mL) is added and the mixture is extracted with ethyl acetate (3×40 mL). The combined organic fraction is dried ($Na_2SO_4$) and the solvent evaporated. The residue is purified by chromatography on a column (300 g) of silica gel. Tetra-alkylated and tri-alkylated compounds are eluted with toluene:ethyl acetate (30:1 by vol.). The third fraction (di-substituted compound, trans-isomer) is eluted with toluene:ethyl acetate (15:1 by vol.). The fourth fraction (di-substituted compound, cis-isomer) is eluted with toluene:ethyl acetate (10:1 by vol.) and the desired product (mono-alkylated compound) is eluted with toluene:ethylacetate (5:1 by vol.). The solvent is removed under reduced pressure and the residue dried under high vacuum to give the product as a violet solid.

$^1$H-NMR: $\delta_H$ (300 MHz, d6-acetone): 0.75 (t, $^3J$=6.8 Hz), 1.13-1.25 (m, 8H), 1.43 (quint, $^3J$=7.5 Hz), 1.73 (quint, 2 H, $^3J$=7.5 Hz), 3.50 (t, $^3J$=8 Hz), 7.11 (d, 2H, $^3J$=7.5 Hz), 7.16 (d, 6 H, $^3J$=7.5 Hz), 7.90-7.94 (m, 8H), 8.80-8.90 (m, 8 H)

COMPOUND 44

5-(4-Dodecyloxy-phenyl)-10,15,20-tris-(4-hydroxyphenyl)-porphyrin

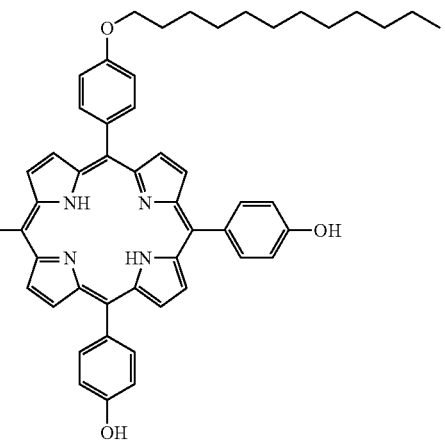

5,10,15,20-tetrakis-(4-Hydroxy-phenyl)-porphyrin (200 mg, 0.294 mmol) is dissolved and potassium carbonate (487 mg, 3.53 mmol, 12 eqv.) in suspended under argon in absolute DMF (50 mL) and the mixture is heated to 55° C. A solution of dodecyl bromide (49.4 µl, 0.206 mmol), 0.7 eqv.) in absolute DMF (10 mL) is added dropwise during 30 min. The mixture is stirred at 55° C. for 2 h. The solvent is removed in vacuo at 50° C., water (80 mL) is added and the mixture extracted with ethyl acetate (3×40 mL). The combined organic fractions are dried ($Na_2SO_4$) and the solvent evaporated. The product is isolated by chromatography on a column (300 g) of silica. Tetra-alkylated and tri-alkylated compounds are eluted with toluene:ethyl acetate (30:1 by vol.), di-substituted compound (trans-isomer) with toluene:ethyl acetate (15:1 by vol.), di-substituted compound (cis-isomer) with toluene:ethyl acetate (10:1 by vol.) and the desired product (mono-alkylated compound) with toluene:ethyl acetate (5:1 by vol). Solvent is removed in vacuo and the residue dried at high vacuum to give product as a violet solid.

$^1$H-NMR: $\delta_H$ (300 MHz, d6-acetone): 0.75 (t, 3H, $^3J$=6.8 Hz), 1.13-1.25 (m, 16H), 1.41 (quint, 2H, $^3J$=7.5 Hz), 1.63 (quint, 2 H, $^3J$=7.5 Hz), 3.89 (t, 2H), $^3J$=6 Hz), 7.11 (d, 2H, $^3J$=7.5 Hz), 7.16 (d, 6H, $^3J$=7.5 Hz), 7.9-7.94 (m, 8H), 8.78-8.83 (m, 8 H)

COMPOUND 45

5,10,15-tris-(4-Hydroxy-phenyl)-20-(4-nonyloxy-phenyl)-porphyrin

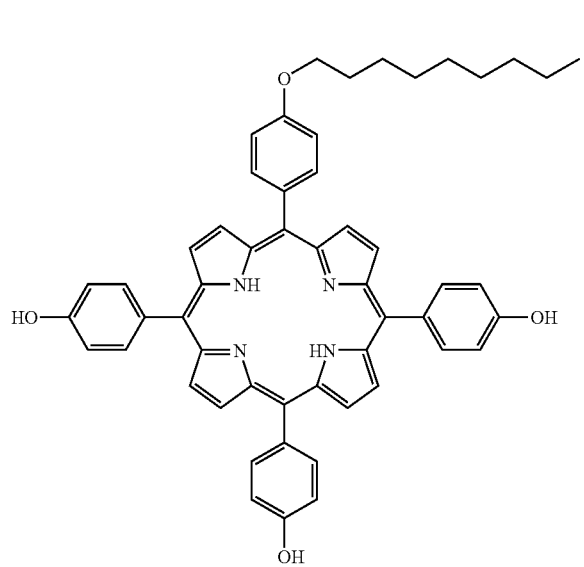

5,10,15,20-tetrakis-(4-Hydroxy-phenyl)-porphyrin (200 mg, 0.294 mmol) is dissolved and potassium carbonate (487 mg, 3.53 mmol, 12 eqv.) is suspended under argon in absolute DMF (50 mL) and the mixture heated to 55° C. A solution nonyl bromide (49.4 µl, 0.206 mmol, 0.7 eqv.) in absolute DMF (10 mL) is added dropwise during 30 min. The mixture is stirred at 55° C. for 2 h. The solvent is removed in vacuo at 50° C., water (80 mL) is added and the mixture extracted with ethyl acetate (3×40 mL). The combined organic extracts are dried (Na$_2$SO$_4$) and solvent removed under reduced pressure. The product is isolated by chromatography on a column (300 g) of silica. Tetra-alkylated and tri-alkylated compounds are eluted with toluene:ethyl acetate (30:1 by vol.), di-substituted compound (trans-isomer) with toluene:ethyl acetate (15:1 by vol.), di-substituted compound (cis-isomer) with toluene:ethyl acetate (10:1 by vol.) and the desired product (mono-alkylated compound) is eluted with toluene:ethyl acetate (5:1 by vol.). The solvent is removed under reduced pressure and the residue dried at high vacuum to afford the product as a violet solid.

$^1$H-NMR: $\delta_H$ (300 MHz, d6-acetone): 0.87 (t, 3H, $^3J$=7.5 Hz), 1.14-1.26 (m, 10H), 1.41 (quint, 2H), 1.70 (quint, 2H, $^3J$=7.5 Hz), 3.92 (t, 2H, $^3J$=7.5 Hz), 7.02 (d, 2H, $^3J$=8.25 Hz), 7.15 (d, 6H, $^3J$=7.5 Hz), 7.85 (d, 2H, $^3J$=8.25 Hz), 7.91 (d, $^3J$=7.5 Hz), 8.76-8.84 (m, 8 H)

COMPOUND 46

5-(4-Octyloxy-phenyl)-10,15,20-tris-[4-(3-trimethy-lammonio-propyloxy)-phenyl]-porphyrin trichloride

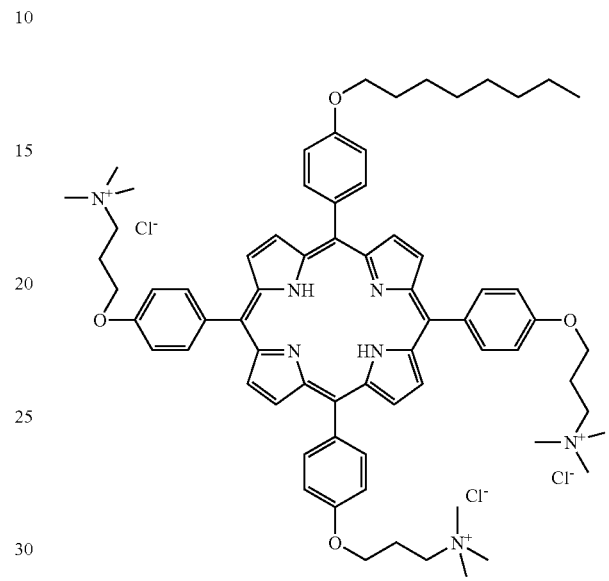

Compound 43 (50 mg, 0.053 mmol) and 3-bromopropyl)-trimethylammonium bromide (164 mg, 0.63 mmol, 10 eqv.) are dissolved and potassium carbonate (130 mg, 0.95 mmol, 15 eqv.) is suspended under argon in absolute DMF (30 mL) and the mixture is stirred at 55° C. for 12 h. The solvent is removed in vacuo at 50° C. and the residue applied to a pad (2 cm deep) of silica. The unreacted ammonium salts are washed off with methanol (1000 mL) and the product is eluted with acetic acid:methanol:water (3:2:1 by vol.). The solvent is removed under reduced pressure and the residue further purified by chromatography on a column (100 g) of Sephadex LH-20 using n-butanol:water:acetic acid (4:5:1 by vol., upper phase) as the eluent. The solvents are removed under reduced pressure and the residue dissolved in methanol and passed through a small column of anion exchange resin (Amberlite IRA 400, chloride form) using methanol as eluent. After evaporation of solvent, the crude product is dissolved in the minimum amount of methanol and diethylether (50 mL) added. The solution is centrifuged for 15 min. The supernatant liquid is evaporated to dryness and the residue dried at high vacuum to give the product as a violet solid.

$^1$H-NMR: $\delta_H$(300 MHz, CD$_3$OD): 0.90 (t, 3H, $^3J$=7.5 Hz), 1.25-1.41 (m, 8H), 1.45 (bs, 2H), 1.87 (bs, 2H), 2.38 (bs, 6H), 3.29 (bs, 27H), 3.67 (t, 6H, $^3J$=7.5 Hz), 4.01 (t, 2H, $^3J$=7.5 Hz), 4.30 (t, 6H, $^3J$=7.5 Hz), 7.11 (d, 2H, $^3J$=7.5 Hz), 7.38 (d, 6H, $^3J$=7.5 Hz), 7.95 (d, 2H, $^3J$=7.5 Hz), 8.11 (d, 6H, $^3J$=7.5 Hz), 8.93 (bs, 8H)

COMPOUND 47

5-(4-Dodecyloxy-phenyl)-10,15,20tris-[4-(3-trimethylammonio-propyloxy)-phenyl]-porphyrin trichloride

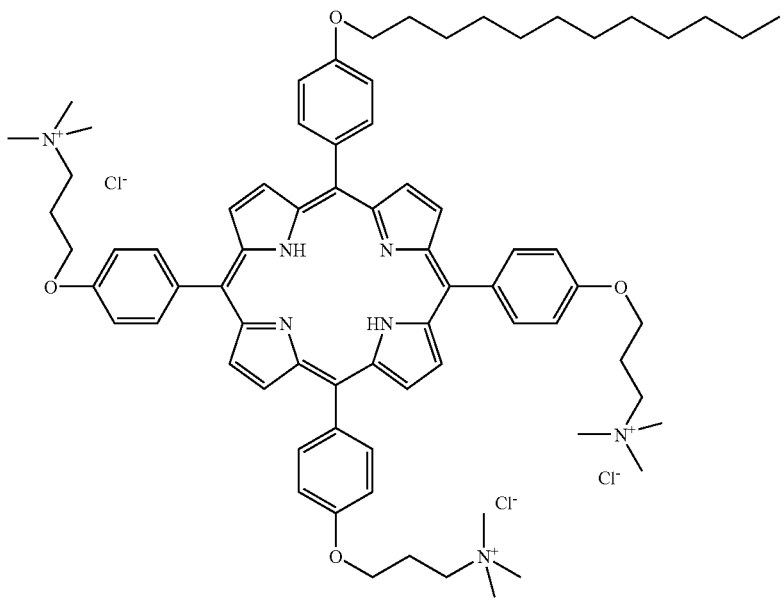

Compound 44 (50 mg, 0.059 mmol) and (3-bromopropyl)-trimethylammonium bromide (1554 mg, 0.59 mmol, 10 eqv.) are dissolved and potassium carbonate (122 mg, 0.885 mmol, 15 eqv.) is suspended under argon in absolute DMF (30 mL) and the mixture is stirred at 55° C. for 12 h. The solvent is removed in vacuo at 50° C. and the residue re-dissolved in a little methanol and applied to a pad of silica (2 cm deep). The unreacted ammonium salts are washed off with methanol (1000 mL). the product is eluted with acetic acid:methanol:water (3:2:1 by vol). The solvents are removed under reduced pressure and the crude product further purified by chromatography on a column (100 g) of Sephadex LH-20 using n-butanol:water:acetic acid (4:5:1 by vol., upper phase) as eluent. The solvents are removed under reduced pressure, the residue re-dissolved in a little methanol and the solution passed through a short column of anion exchange resin (Amberlite IRC 400, chloride form) using methanol as eluent. After removal of solvent the crude product is re-dissolved in the minimum amount of methanol and diethyl ether (50 mL) added. The solution is centrifuged for 15 min. The supernatant liquid is evaporated to dryness and the product dried at high vacuum to give a violet solid.

$^1$H-NMR: $\delta_H$ (300 MHz, CD$_3$OD): 0.88 (t, 3H, $^3$J=7.5 Hz), 1.25-1.37 (m, 16H), 1.48 (bs, 2H), 2.42 (bs, 6H), 3.29 (bs, 27H), 3.68-3.75 (m, 6H), 4.05 (t, 2H), 4.33 (t, 6H) 717 (d, 2H, $^3$J=7.5 Hz), 7.33 (d, 6H, $^3$J=7.5 Hz), 7.99 (d, 2H, $^3$J=7.5 Hz), 8.08 (d, 6H, $^3$J=7.5 Hz), 8.85 (bs, 8H)

COMPOUND 48

5-(4-Nonyloxy-phenyl)-10,15,20-tris-[4-(3-trimethylammonio-propyloxy)-phenyl]-porphyrin trichloride

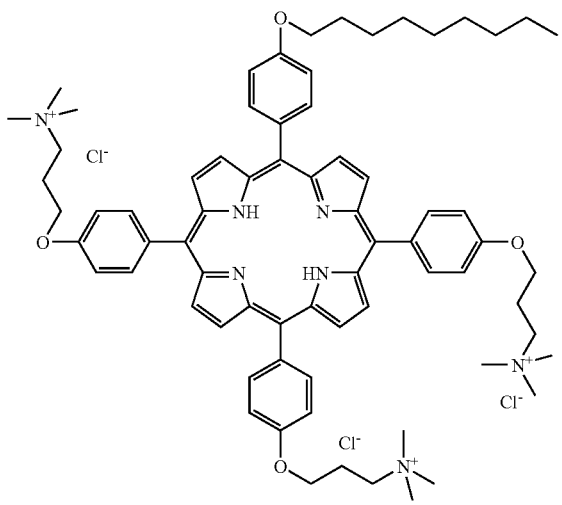

Compound 45 (50 mg, 0.062 mmol) and (3-bromopropyl)-trimethylammonium bromide (162 mg, 0.62 mmol, 10 eqv.) are dissolved and potassium carbonate (128 mg, 0.93 mmol, 15 eqv.) is suspended under argon in absolute DMF (30 mL) and the mixture is stirred at 55° C. for 12 h. The solvent is removed in vacuo at 50° C. and the residue re-dissolved in a little methanol and applied to a pad of silica (2 cm deep). The unreacted ammonium salts are washed off with methanol (1000 mL). The product is eluted with acetic acid:methanol:water (3:2:1 by vol.). The solvents are removed under reduced pressure and the product further purified by chromatography on a column (100 g) of Sephadex LH-20 eluting with n-butanol:water:acetic acid (4:5:1 by vol., upper phase). The solvents are removed under reduced pressure, the residue re-dissolved in a little methanol and the solution is passed through a short column of anion exchange resin (Amberlite IRC 400, chloride form) using methanol as eluent. After removal of solvent, the product is dried at high vacuum to give a violet solid.

$^1$H-NMR: $\delta_H$ (300 MHz, CD$_3$OD): 0.89 (t, 3H, $^3J$=7.5 Hz), 1.18-1.34 (m, 10H), 1.41 (bs, 2H), 1.73 (quint, 2H, $^3J$=7.5 Hz), 2.30-2.44 (m, 6H), 3.31 (bs, 27H), 3.36-3.73 (m, 6H), 3.93 (t, 2H, $^3J$=7.5 Hz), 4.25-4.42 (m, 6H), 7.08 (d, 2H, $^3J$=7.5 Hz), 7.30 (d, 6H, $^3J$=7.5 Hz), 7.93 (d, 2H, $^3J$=7.5 Hz), 8.05 (d, 6H, $^3J$=7.5 Hz), 8.94 (bs, 8H)

COMPOUND 49

5-(4-Octyloxy-phenyl)-10,15,20-tris-[4(5-trimethylammonio-pentyloxy)-phenyl]-porphyrin trichloride

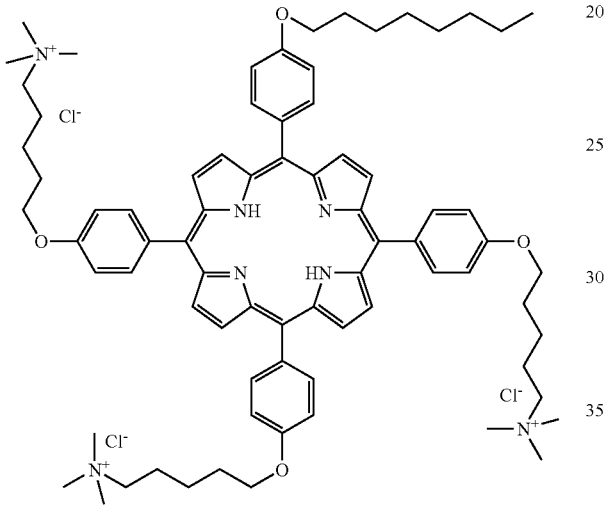

Compound 43 (23 mg, 0.03 mmol) and (5-bromopentyl)-trimethylammonium bromide (84 mg, 0.3 mmol, 10 eqv.) are dissolved and potassium carbonate (62 mg, 0.45 mmol, 15 eqv.) is suspended under argon in absolute DMF (15 mL) and the mixture is stirred at 55° C. for 12 h. The solvent is removed in vacuo at 50° C. and the residue re-dissolved in a little methanol and applied to a pad (2 cm deep) of silica. The unreacted ammonium salts are washed off with methanol (1000 mL). The product is eluted with acetic acid:methanol:water (3:2:1 by vol.). The solvents are removed under reduced pressure and the product further purified by chromatography on a column (100 g) of Sephadex LH-20 using n-butanol:water:acetic acid (4:5:1 by vol., upper phase) as eluent. The solvents are removed under reduced pressure, the residue re-dissolved in a little methanol and the solution passed through a short column of anion exchange resin (Amberlite IRC 400, chloride form) with methanol as eluent. The complete purification process is repeated is impurities, remain in the product. After removal of solvent, the residue is dried at high vacuum to give the product as a violet solid.

$^1$H-NMR: $\delta_H$ (300 MHz, CD$_3$OD): 0.78 (bs, 3H), 1.08-1.35 (m, 10H), 1.45-1.59 (m, 6H), 1.63-1.93 (m, 14H), 3.17-3.32 (m, 6H), 3.31 (bs, 33H), 3.84 (bs, 2H), 4.07 (bs, 6H), 6.93 (bs, 2H), 7.09 (d, 2H, $^3J$=7.5 Hz), 7.74 (bs, 2H), 7.88 (d, 2H, $^3J$=7.5 Hz), 8.71 (bs, 8H)

COMPOUND 50

5,10,15-tris-[4-(5-Trimethylammonio-pentyloxy)-phenyl]-20-(4-undecyloxy-phenyl)-porphyrin trichloride

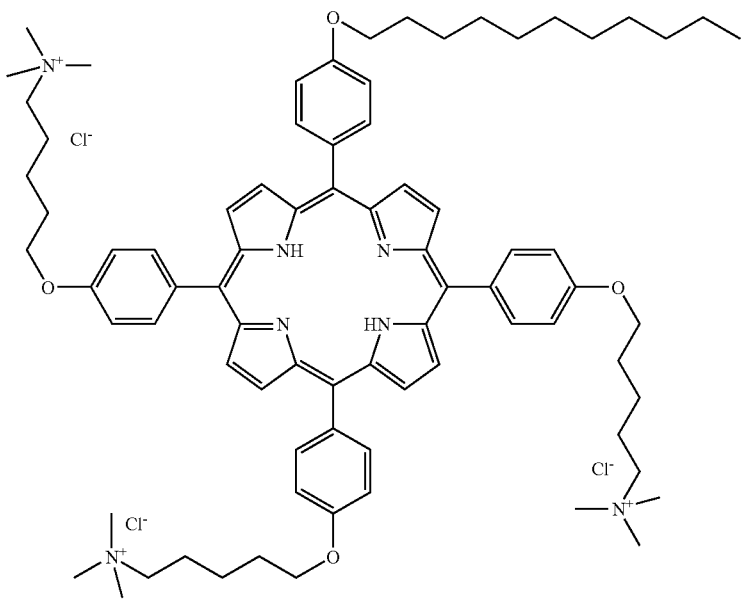

Compound 2 (50 mg, 0.06 mmol) and (5-bromopentyl)-trimethylammonium bromide (174 mg, 0.6 mmol, 10 eqv.) are dissolved and potassium carbonate (124 mg, 0.9 mmol, 15 eqv.) is suspended under argon in absolute DMF (30 mL) and the mixture is stirred at 55° C. for 12 h. The solvent is removed in vacuo at 50° C. and the residue re-dissolved in a little methanol and applied to a pad (2 cm deep) of silica. The unreacted ammonium salts are washed off with methanol (1000 mL). The product is eluted with acetic acid:methanol:water (3:2:1 by vol.). Solvents are removed under reduced pressure and the product further purified by chromatography on a column (100 g) of Sephadex LH-20 eluting with n-butanol:water:acetic acid (4:5:1 by vol., upper phase). Solvents are removed under reduced pressure, the residue re-dissolved in the minimum of methanol and the solution passed through a short column of anion exchange resin (Amberlite IRC 400) with methanol as eluent. The complete purification process is repeated if impurities remain in the product. After removal of solvent, the residue is dried at high vacuum to give the product as a violet solid.

$^1$H-NMR: $\delta_H$ (300 MHz, MeOD): 0.71-0.88 (m, 13H), 0.91-1.38 (m, 14H), 1.48-1.81 (m, 12H), signals for —CH$_2$NCH$_2$ and OCH$_2$-long alkyl chain are part of the multiplet together with the signals for solvent in the area 2.8-3.3, 3.91 (bs, 6H), 6.33 (bs, 2H), 6.86 (bs, 6H), 7.35 (bs, 2H), 7.70 (bs, 6H), 8.65 (bs, 8H)

COMPOUND 51

5,10,15,20-tetrakis-(3-Dodecyloxy-phenyl)-porphyrin

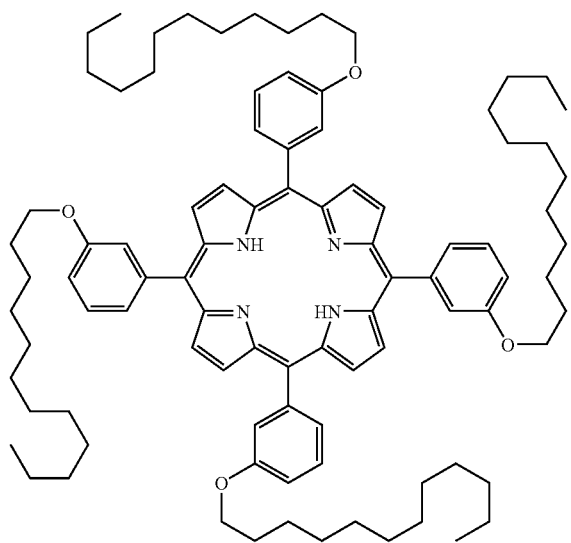

Pyrrole (0.7 mL, 10 mmol) and 3-dodecyloxybenzaldehyde (2.91 g, 10 mmol) are dissolved in degassed dichloromethane (1000 mL) and TFA (0.77 mL, 10 mmol) is added dropwise. The mixture is stirred for 17 h at room temperature in the dark. DDQ (6.81 g, 30 mmol) is added in one portion and the mixture is stirred for a further 1 h at room temperature. The mixture is filtered through a column (400 g) of silica using dichloromethane as eluent followed by dichloromethane to which triethylamine is added to adjust pH value to 8. This purification process is repeated if impurities remain in the product until the pure product is obtained.

$^1$H-NMR: $\delta_H$ (300 MHz, d6-acetone): 0.80 (bs, 12H), 1.03-1.45 (m, 80H), 1.78 (quint, 8H, $^3$J=7.5 Hz), 4.05 (t, 8H, $^3$J=7.5 Hz), 7.24 (d, 4H, $^3$J=7.5 Hz), 7.49-7.55 (m, 4H), 7.68-7.71 (m, 8H), 8.80 (m, 8 H)

Example B

Non-Specific (Dark Toxicity) Profiles and Photodynamic Activity (Light Toxicity) Profiles of Exemplary Compounds on Bacterial Cells Methodology The toxic effects of exemplary compounds of the invention against two bacterial strains, the Gram negative bacterium *Escherichia coli* (strain ATCC 25922) and the Gram positive bacterium *Staphylococcus aureus* (methicillin-resistant strain ATTC BAA-44), were evaluated by measuring the extent of growth inhibition (bacteriostatic effect) and growth inhibition (cytocidal effect) in the dark and upon light exposure. Initial compound screening was undertaken using white light [390-740 nm] (150 mW/cm$^2$) for various timepoints of a concentration of 3 μM (see Table 1). Further experiments were undertaken on those compounds identified from this initial screen using a light source emitting light at a wavelength between 417-420 nm at 15.2 mW/cm$^2$, 13.68 J/cm$^2$ (Waldmann Eclairage SA, France) (see Table 20.

The following protocol was used for the initial screening of the exemplary compounds (Table 1) (see Reddi et al., 2002, *Photochem. Photobiol.* 75(5):462-470):
(i) *E. coli* and *S. aureus* cells were grown overnight on brain heart infusion agar, resuspended in brain heart infusion broth, harvested by centrifugation (3000 g for 15 minutes) and washed once with phosphate buffered saline (PBS) at pH 7.4 consisting 2.7 mM KCl and 0.14 M NaCl.
(ii) The cells were then resuspended in PBS to an optical density at 650 nm of 0.7, which corresponds to a density of 10$^8$ to 10$^9$ cells/ml.
(iii) Next, the cells were incubated in PBS in the dark for 5 minutes with 3.0 μM of the compound to be tested.
(iv) After dark incubation, cells were illuminated with white light (wavelength: 390 to 740 nm) (150 mW/cm$^2$) for up to 30 minutes. During illumination, the cells were kept at 37° C. and magnetically stirred.
(v) Finally, treated and untreated (control) cells were diluted in brain heart infusion broth and maintained at 3720 C. while the absorbance of the suspension at 650 nm was monitored at predetermined time points for determining growth curves.

The percent of growth inhibition in the treated cells was calculated by the following equation:

$$[1-(A_x-A_0)/(A_c-A_0)] \times 100$$

where $A_x$ $A_c$ are the absorbances measured after 3 hours incubation, for the treated and control cell suspensions, respectively, and $A_0$ represents the initial absorbance.

For the further investigation of the exemplary compounds (Table 2), the following protocol was adopted:
(i) Bacteria (*S. aureus* BAA-44 and *E. coli* 25922) were grown in brain heart infusion (BHI) broth until they reached the stationary phase of growth.
(ii) The cells were harvested by centrifugation (3000 g for 15 min) with a table centrifuge, washed with 10 mM PBS at pH 7.4 containing 2.7 mM KCl and 0.14 M NaCl and suspended in PBS at an optical density of 0.7 at 650 nm corresponding to 10$^8$-10$^9$ cells/ml.

(iii) The bacteria, at the desired cell density (~$10^8$ cells/ml) were incubated for 5 min in the dark with various concentrations of the exemplary compounds.
(iv) At the end of the incubation period the cells were washed three times with PBS, suspended in PBS, transferred into a 96-well microtitre plate (200 μl/well) and illuminated for 15 min with the Waldmann light source (15.2 mW/cm$^2$; 13.7 J/cm$^2$). The cells were illuminated from the bottom of the plate laying it on the glass cover of the lamp.
(v) After illumination, cell survival was determined by plating serially diluted aliquots of treated and untreated (i.e. no exemplary compound or light present) cells onto brain heart agar (BHA) and counting the number of colonies after 18-24 h incubation at 37° C.

TABLE 1

Growth inhibition (%) of *E. coli* and *S. aureus* cells irradiated with white light after 5 min incubation with selected test compounds at a concentration of 3 μM.

(A)

| Illumination time (min) | E. coli | | | | S. aureus | | | |
|---|---|---|---|---|---|---|---|---|
| | Cpd 16 | Cpd 3 | Cpd 19 | Cpd 28 | Cpd 16 | Cpd 3 | Cpd 19 | Cpd 28 |
| 0 | 8 | 5 | 3 | 4 | 12 | 21 | 13 | 15 |
| 1 | 34 | 68 | 5 | 21 | 97 | 83 | 33 | 91 |
| 5 | 92 | 99 | 6 | 60 | 100 | 100 | 42 | 100 |
| 10 | 99 | 100 | 5 | 73 | 100 | 100 | 48 | 100 |
| 15 | 100 | 99 | 10 | 81 | 100 | 100 | 54 | 100 |
| 30 | 100 | 99 | 12 | 92 | 100 | 100 | 58 | 100 |

(B)

| Illumination time (min) | E. coli | | | | | S. aureus | | | | |
|---|---|---|---|---|---|---|---|---|---|---|
| | Cpd 29 | Cpd 31 | Cpd 32 | Cpd 6 | Cpd 33 | Cpd 29 | Cpd 31 | Cpd 32 | Cpd 6 | Cpd 33 |
| 0 | ND | ND | 3 | 9 | 6 | 14 | 9 | 23 | 29 | 22 |
| 1 | ND | ND | 10 | 17 | 10 | 43 | 28 | 100 | 100 | 57 |
| 5 | ND | ND | 16 | 30 | 25 | 49 | 38 | 100 | 100 | 99 |
| 10 | ND | ND | 22 | 54 | 53 | 53 | 78 | 100 | 100 | 100 |
| 15 | ND | ND | 22 | 69 | 67 | 55 | 82 | 100 | 100 | 100 |
| 30 | ND | ND | 38 | 93 | 78 | 55 | 83 | 100 | 100 | 100 |

(C)

| Illumination time (min) | E. coli | | S. aureus | |
|---|---|---|---|---|
| | Cpd 36 | Cpd 8 | Cpd 36 | Cpd 8 |
| 0 | 6 | 23 | 22 | 80 |
| 1 | 56 | 69 | 96 | 99 |
| 5 | 84 | 100 | 100 | 100 |
| 10 | 90 | 100 | 100 | 100 |
| 15 | 92 | 100 | 100 | 100 |
| 30 | 95 | 100 | 100 | 100 |

Results

Figure 1:
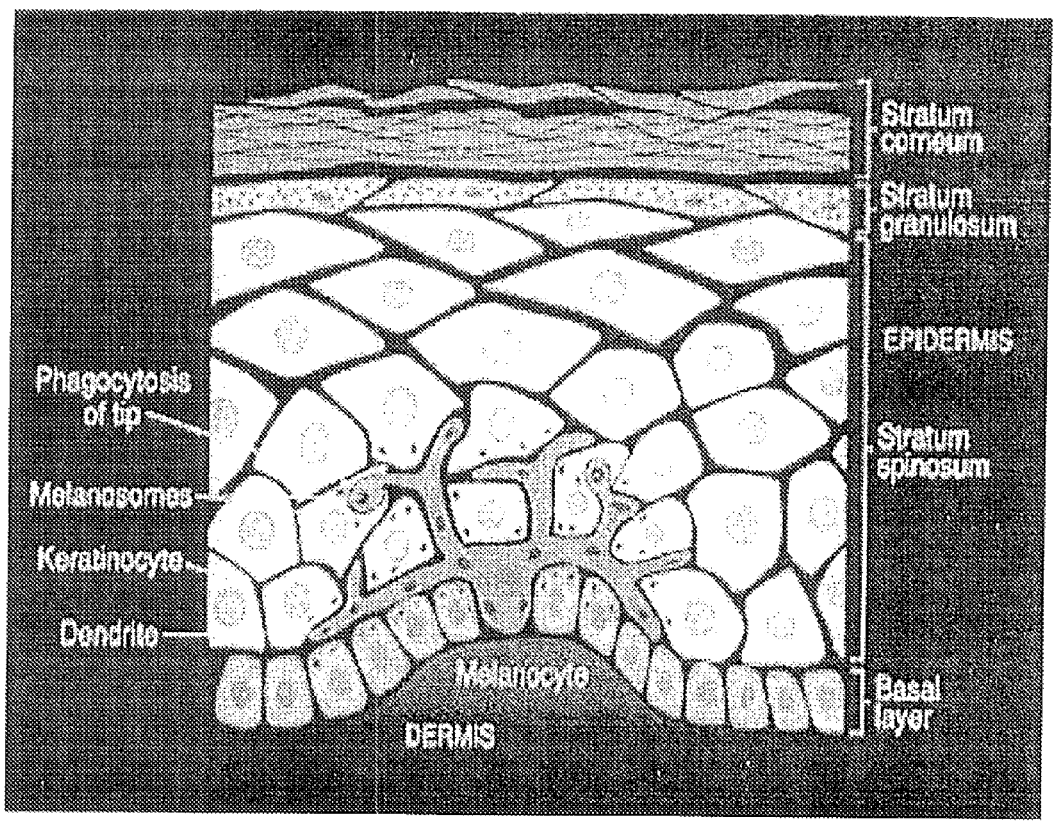
FIG. 1 shows a schematic diagram of the structure of skin.
Figure 2A:
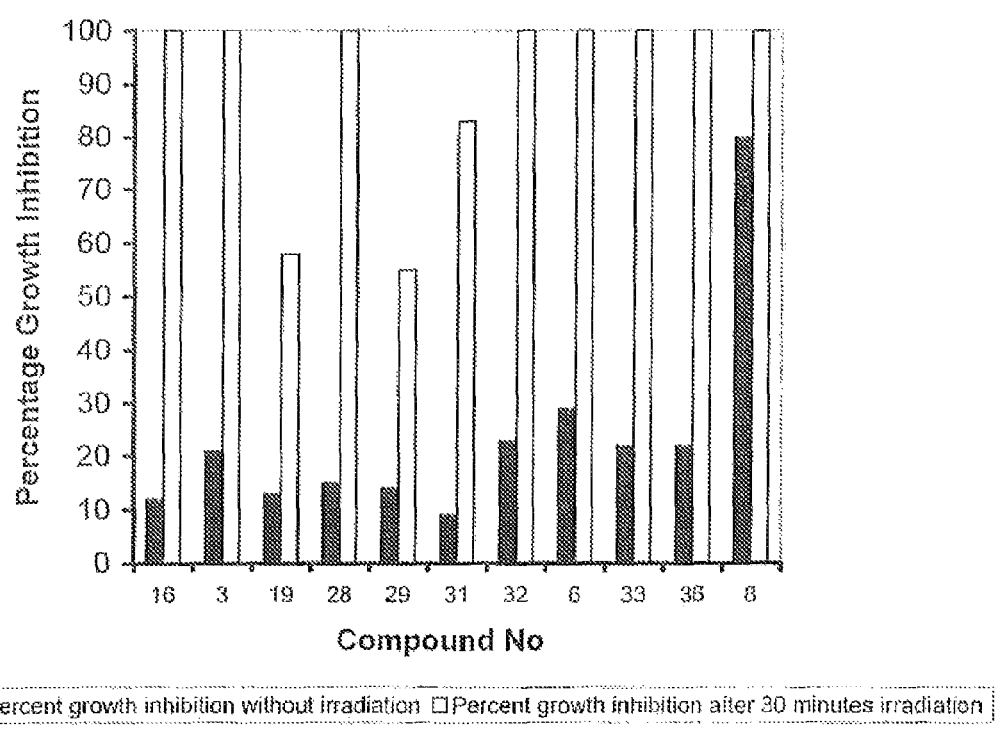
FIG. 2 shows the growth inhibition (%) of (A) S. aureus BAA-44 cells and (B) E. coli ATCC 25922 cells illuminated with white light (150 $mW/cm^2$) for 0 or 30 minutes following pre-incubation for 5 minutes with a test compound at a concentration of 3 µM.
Figure 2B:
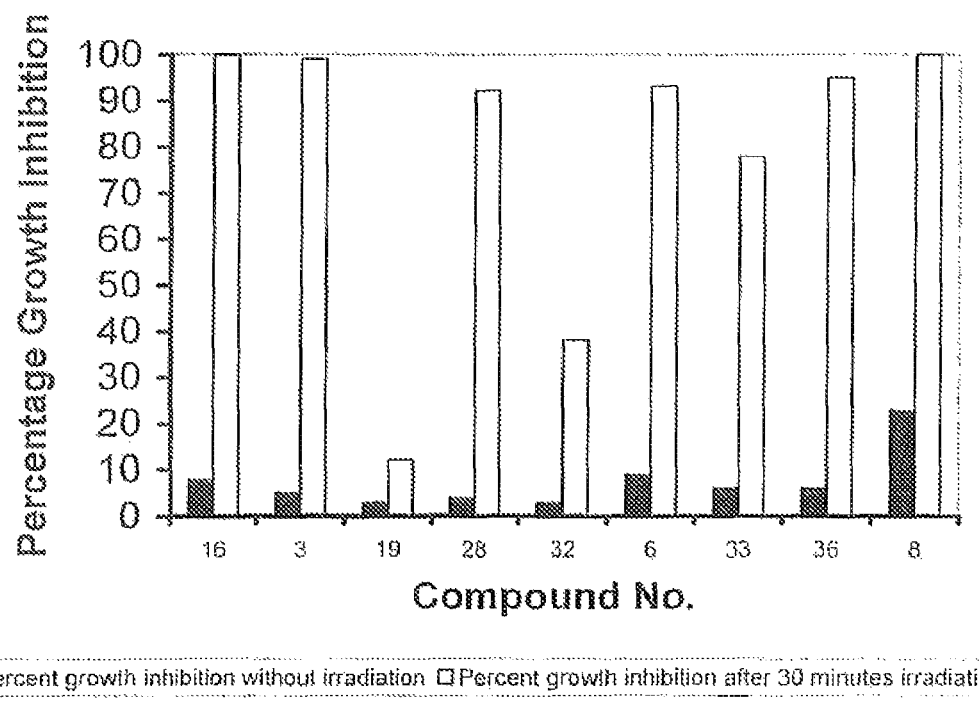
Figure 3A:
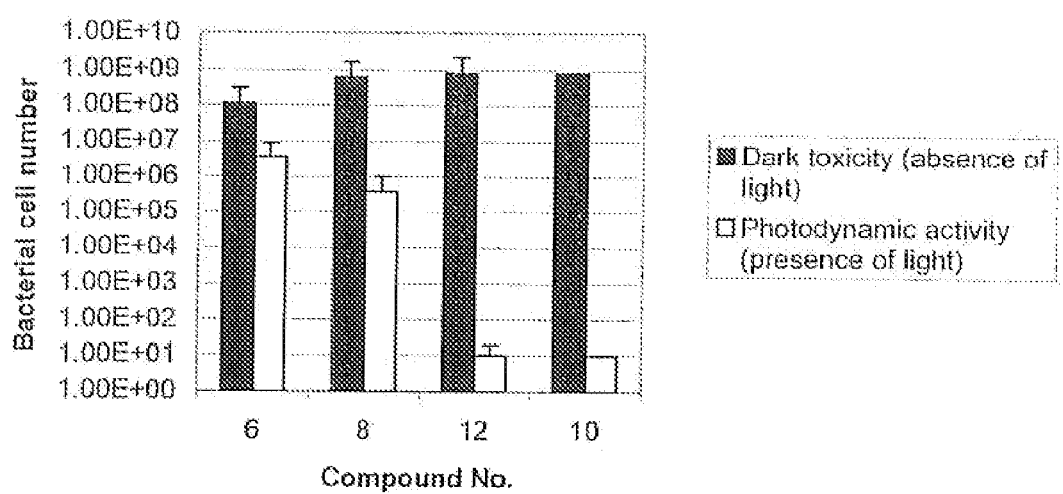
FIG. 3 shows bacterial survival (cell number) of (A) S. aureus BAA-44 and (B) E. coli ATCC 25922 cells after incubation with a test compound at a concentration of 0.1 µM and illumination with light ('light toxicity', i.e. photodynamic activity) or no illumination ('dark toxicity').
Figure 3B:
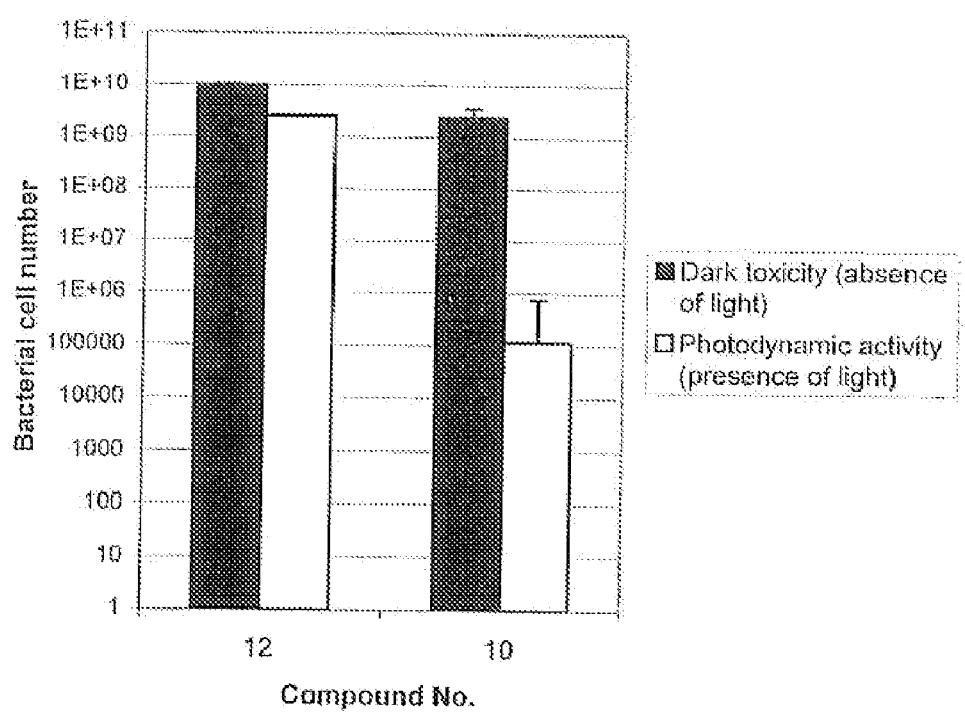

Results of the toxicity studies in *E. coli* and *S. aureus* are shown in Tables 1 and 2, together with FIGS. 1 and 3 (see Example A for compound, 'Cpd', structures).

TABLE 2

Survival of *E. coli* and *S. aureus* cells after incubation with selected test compounds and illumination with white light ('photodynamic activity' or light toxicity) or no illumination ('dark toxicity')

(A)

| | Compound 3 | | | Compound 6 | | | Compound 8 | | |
|---|---|---|---|---|---|---|---|---|---|
| concn | illumination | Log reduction | concn | illumination | Log reduction | concn | illumination | Log reduction |
| PHOTODYNAMIC ACTIVITY (a) *S. aureus* | | | | | | | | | |
| 10 μM | 15 min | >6 (>$10^{-6}$) | 1 μM | 15 min | 6 ($10^{-6}$) | 1 μM | 15 min | 6 ($10^{-6}$) |
| 1 μM | 15 min | >3 (>$10^{-3}$) | 0.1 μM | 15 min | 3 ($10^{-3}$) | 0.1 μM | 15 min | 3 ($10^{-3}$) |

TABLE 2-continued

Survival of *E. coli* and *S. aureus* cells after incubation with selected test compounds and illumination with white light ('photodynamic activity' or light toxicity) or no illumination ('dark toxicity')

(A)

(b) *E. coli*

| | | | | | | | | |
|---|---|---|---|---|---|---|---|---|
| | ND | | | ND | | 10 μM | 15 min | >6 (>$10^{-6}$) |
| | ND | | | ND | | 0.01 μM | 15 min | <1 (<$10^{-1}$) |

DARK TOXICITY
(a) *S. aureus*

| 10 μM | N/A | >3 (>$10^{-3}$) | 10 μM | 15 min | 2 ($10^{-2}$) | 1 μM | N/A | <1 (<$10^{-1}$) |
| 1 μM | N/A | <1 (<$10^{-1}$) | 1 μM | 15 min | 1 (<$10^{-1}$) | 10 μM | N/A | <1 (<$10^{-1}$) |

(b) *E. coli*

| | ND | | | ND | | 10 μM | N/A | 2 ($10^{-2}$) |
| | ND | | | ND | | 0.01 μM | N/A | <1 (<$10^{-1}$) |

| Compound 1 | | | Compound 12 | | | Compound 10 | | |
|---|---|---|---|---|---|---|---|---|
| concn | Illumination | Log reduction | concn | illumination | Log reduction | concn | illumination | Log reduction |

PHOTODYNAMIC ACTIVITY
(a) *S. aureus*

| 1 μM | 15 min | >6 (>$10^{-6}$) | 1 μM | 15 min | >6 (>$10^{-6}$) | 0.01 μM | 15 min | >4 (>$10^{-4}$) |
| 0.1 μM | 15 min | <1 (<$10^{-1}$) | 0.1 μM | 15 min | >3 (>$10^{-3}$) | 0.005 μM | 15 min | >3 (>$10^{-3}$) |
| | | | 0.005 μM | 15 min | <2 (<$10^{-2}$) | | | |

(b) *E. coli*

| | ND | | 1 μM | 15 min | >6 (>$10^{-6}$) | 1 μM | 15 min | >6 (>$10^{-6}$) |
| | ND | | 0.5 μM | 15 min | <1 (<$10^{-1}$) | 0.5 μM | 15 min | <3 (<$10^{-1}$) |

DARK TOXICITY
(a) *S. aureus*

| 10 μM | N/A | <1 (<$10^{-1}$) | 1 μM | N/A | <1 (<$10^{-1}$) | 0.01 μM | N/A | <1 (<$10^{-1}$) |

(b) *E. coli*

| | ND | | 1 μM | N/A | <1 (<$10^{-1}$) | 1 μM | N/A | <1 (<$10^{-1}$) |

Conclusions

The results demonstrate that the compounds of the invention, when illuminated with light, are capable of killing both gram positive and gram negative bacterial cells at the low concentrations investigated.

Figure 4A:
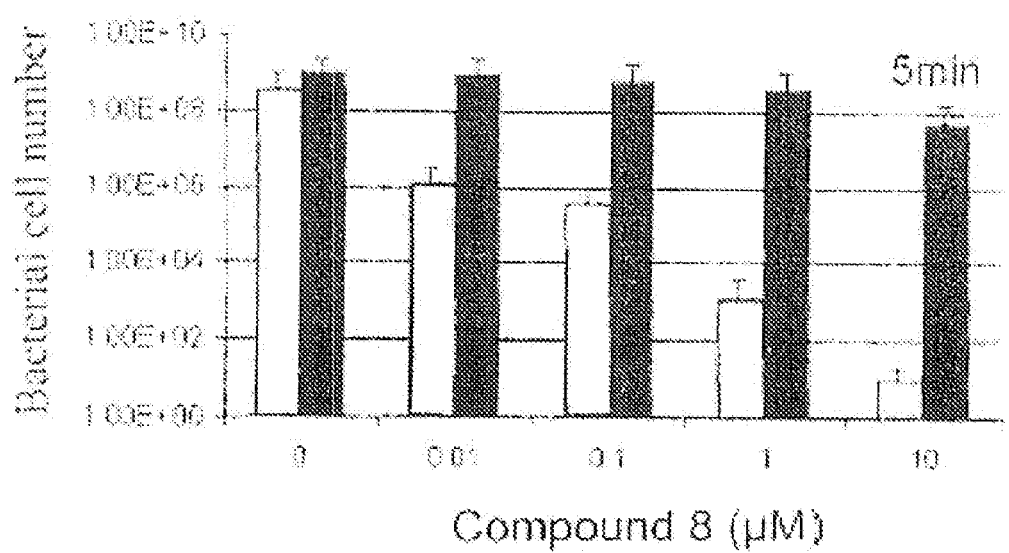
FIG. 4 shows the photodynamic activity (open bars) and dark toxicity (shaded bars) of (A) 'Compound 8' and (B) 'Compound 10' against S. aureus BAA-44 at varying doses.
Figure 4B:
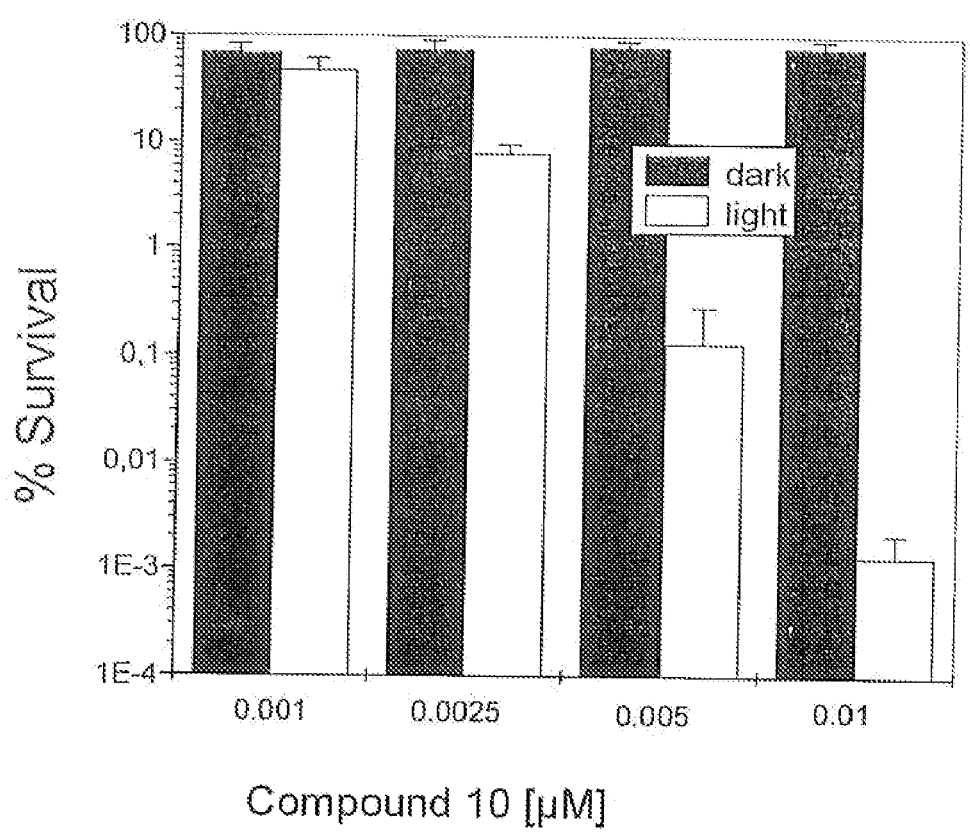

Activity of Compound 10 at Low Doses the above colony forming unit (CFU) protocol was also used to investigate the photodynamic activity of very low concentrations of the compounds of the invention. For example, FIG. 4 demonstrates the results obtained using (A) Compound 8 and (B) Compound 10 in the presence (photodynamic properties) and in the absence (inherent toxicity properties) of light.

Results
(i) Compounds 8 and 10 both exhibited negligible dark toxicity against BAA-44 at the concentrations testes.
(ii) Compound 8 exhibited a potent antibacterial effect at concentrations as low as 0.01 μM, where a 3 log reduction in BAA-44 was achieved.
(iii) Compound 10 exhibited an even more potent antibacterial effect, causing a 3 log reduction in BAA-44 at a concentration of 0.005 μM and capable of killing 90% of the bacteria at a 0.0025 μM concentration.

Conclusions

Compounds 8 and 10 exhibit a dose-dependent and light-dependent toxicity against bacterial cells, even at very low doses.

Range of Antimicrobial Activity

The antibacterial activity of Compound 10 was tested against a range of bacterial strains:

*S. aureus* ATCC BAA-44 (a methicillin resistant *S. aureus*)
*Ps. aeruginosa* ATCC 25668
*S. epidermidis* ATCC 700565
*Streptococcus pyogenes* ATCC 49117
*E. coli* ATCC 25922

TABLE 3

| Strain | Concentration of Compound 10 required to obtain a 3 log reduction in cells (μM) |
|---|---|
| *Staphylococcus aureus* ATCC BAA-44 | 0.005 |
| *Pseudomonas aeruginosa* ATCC 25668 | 5.0 |
| *Staphylococcus epidermidis* ATCC 700565 | 0.0025 |
| *Streptococcus pyogenes* ATCC 49117 | 0.01 |
| *E. coli* ATCC 25922 | 0.1 |

Conclusions

Compound 10 exhibits photodynamic activity (i.e. light toxicity) against a broad range of gram positive and gram negative bacteria.

Photodynamic Activity of Compound 10 Against MRSA on ex vivo Porcine Skin

Excised porcine skin was cut into 3(4)×3(4) cm² pieces under sterile conditions and incubated in 70% ethanol for 5 minutes to reduce background of colonised bacteria. After three washing steps in PBS, the skin pieces were fixed in petri dishes with Hepes-Agar. The epidermis (stratum corneum) was then inoculated with *S. aureus* ATCC BAA-44 (~$10^8$, Volume: 100 µl) and the skin surface dried under laminar flow cabinet until visible dry. The regions of interest were determined using a "pap" pen (1 cm² diameter). A sterile solution of Compound 10 (10 µM) was applied onto the skin for 10 minutes. Post application, the ex vivo porcine skin was placed under the Waldmann light source 236 and illuminated for 15 min (15.2 mW/cm², 13.7 J/cm²). A colony forming unit assay was performed to determine viable bacterial cell number immediately after irradiation using a sterile cotton rod to remove bacteria from the stratum corneum. The sterile cotton rod was moistened in sampling solution (0.1% Tween80 in 0.0075 M phosphate buffer pH 7.9) before swabbing the skin surface (3 times) and vortexed in sampling solution before undertaking serial dilutions to determine the bacterial recovery.

Incubation with Compound 10 (10 µM) followed by 15 minutes irradiation resulted in a 3.2 $\log_{10}$ growth reduction (mean value of three target areas). In contrast, control experiments (irradiation of applied bacteria without Compound 10 incubation) did not show a decrease of bacteria cell number.

Thus, these data demonstrate photodynamic activity of Compound 10 against MRSA on the surface of porcine skin, even in the presence of skin lipids and enzymes.

Confirmation of Photodynamic Properties Using Sodium Azide and $D_2O$

Quenching studies using $D_2O$ and azide were performed with Compound 10 and light against keratinocytes in vitro. In order to investigate whether phototoxicity of the test compound against NHDF, NHEK and bacteria follows the photo-oxidation type II, sodium azide, a physical quencher of singlet oxygen as well as $D_2O$ an enhancer of reactive oxygen species were (Lin et al., 1991, *Cancer Res.* 51:1109-1116; Moan et al., 1979, *Brit. J. Cancer* 39:398-407).

FIG. 5 shows the effect of incubation with Compound 10 and quencher or Compound 10 and $D_2O$ after illumination. Cell killing by Compound 10 was reduced in the presence of sodium azide, as indicated by an increase of the cell viability, whereas the addition of $D_2O$ revealed a dramatic decrease of cell viability.

In conclusion, the killing of NHDF by Compound 10 with illumination appears to be mediated mainly by singlet oxygen and not by the compound itself.

Acute Toxicity Testing of Compound 10

Compound 10 was used at a million times antibacterial doses (3.2 mM) in a topical formulation in a standard acute toxicity test to determine if any clinical or histological toxicity for the compound could be detected. The compound was applied to both intact and abraded rat skin for 24 hours.

The acute toxicity protocol was based on OECD Guidelines for the testing of chemicals/Section 4—Health Effects Test Number 402: Acute Dermal Toxicity.

Results and Conclusions

After clinical, macroscopic and microscopic observation, no clinical toxicology was observed. No Histological toxicology of any major organ (including the skin) was observed. No cell infiltrates, including mast cells, were noted, neither was irritancy.

In conclusion, Compound 10 does not result in any acute toxic or allergic effect: in fact, no significant clinical or pathological signs related to the substance and its vehicle application were observed.

Photo-Toxicity Testing of Compound 10

The photo-toxicity protocol was based on OECD Guidelines for the testing of chemicals/Section 4 Health Effects—Test Number 406: Skin sensitisation.

Preliminary experiments determined that a light exposure of 30 minutes did not result in any damage to the surface of the skin caused by the light source. Similarly, control experiments demonstrated that Compound 10 when applied at a concentration of 32 µM in the absence of light did not result in any damage to the surface of the skin. The photo-toxicity of the Compound 10 in the topical formulation was studied when applied onto 14 Guinea Pig skin (intact and abraded) for 24 hours, followed by a 30 minute light exposure. Compound 10 was tested at two different concentrations 32 µM. Clinical and histological examination of the skin test sites was conducted at 24 and 72 hours post illumination in classical phototoxicity testing fashion. Biopsies were not done from contiguous sites to prevent any interaction in case of suture. Gross findings were evaluated at the moment of the biopsy. Before giving a score to each endpoint (erythema, oedema and inflammation), data for each subject were compared to the data from the other animals and to control data. A score from 0 to 4 was given for each site and for each endpoint according to the Draize Scale (for inflammation, a scale similar to the Draize Scale was created after microscopic observation of all skin sections, comparing with normal skin and with findings of step-1). A mean score was then calculated for each animal and for each sampling point.

On analysing the results and comparing the experimental data with the data from the control animals, it was concluded that there were no clinical signs or symptoms or histological findings that suggested any photo-toxic potential of Compound 10.

Example C

Binding of Exemplary Compounds of the Invention with Bacterial Cells

Binding of Compounds 8, 10 and 12 with *E. coli*

*E. coli* cells were incubated for 5 min with Compound 8, 10 or 12 at various concentrations (1-7.5 µM). At the end of the incubation period, the cells were sedimented by centrifugation to remove the fraction of unbound test compound and the cell pellet was resuspended in 2 ml of 2% SDS to obtain cell lysates. After overnight incubation with SDS, the amount of cell-bound test compound was estimated by spectrofluorimetric analysis of the cell lysates. The concentration of the compounds in the cell lysates was calculated by measuring the intensities at the maximum of the emission fluorescence spectrum and interpolating the data on a calibration plot. The amount of cell-bound test compound was expressed as nmoles of compound per mg of cell protein. The protein concentration was determined by the method of Lowry (Lowry et al., 1951, *J. Biol. Chem.* 193:265-275).

All experiments were run in triplicate and the results represent the average of 3 determinations with standard deviations.

The amount of porphyrin recovered from the cells is shown in Table 4.

TABLE 4

| Concentration of compound | Bound compound (nmoles/mg cell proteins) | | |
|---|---|---|---|
| (µM) | Compound 8 | Compound 12 | Compound 10 |
| (a) 0 washings | | | |
| 0.01 | 0.024 ± 0.01 | 0.041 ± 0.02 | 0.026 ± 0.005 |
| 0.1 | 0.056 ± 0.02 | 0.151 ± 0.02 | 0.274 ± 0.05 |

TABLE 4-continued

| Concentration of compound | Bound compound (nmoles/mg cell proteins) | | |
|---|---|---|---|
| (µM) | Compound 8 | Compound 12 | Compound 10 |
| 0.5 | 0.522 ± 0.2 | 0.806 ± 0.14 | 1.542 ± 0.350 |
| 1 | 3.670 ± 0.7 | 2.70 ± 0.30 | 2.70 ± 0.354 |
| (b) 3 washings | | | |
| 0.01 | 0.009 ± 0.001 | 0.021 ± 0.005 | 0.015 ± 0.0004 |
| 0.1 | 0.030 ± 0.02 | 0.089 ± 0.02 | 0.078 ± 0.02 |
| 0.5 | 6.274 ± 0.15 | 0.622 ± 0.10 | 0.334 ± 0.092 |
| 1 | 2.230 ± 0.8 | 1.930 + 0.20 | 1.278 ± 0.102 |

The results shown in Table 4 show that the three test compounds bind to *E. coli* with similar efficiency and that about 50% of the compound that is associated to the cells at the end of the incubation period (5 min) is removed by 3 washings with PBS.

Example D

Testing of Exemplary Compounds for Emergence of Bacterial Resistance to PDT

The potential build up of resistance of the bacterial cells to the exemplary compounds of the invention was tested in the multi-drug resistant (including methicillin) gram positive bacterium *Staphylococcus aureus* BAA-44, using Compound 10 as the photodynamic agent. The survival of *S. aureus* BAA-44 after the second treatment was again compared to the survival of *S. aureus* BAA-44 cells that had not been treated with PDT. The same treatment was repeated for a total of 10 times in order to assess if the sensitivity of *S. aureus* BAA-44 cells to PDT remained constant or whether some resistance was observed to develop after repeated treatments. In an additional experiment, clones which had been exposed nine times to PDT treatment by the above methodology were treated for a tenth time and the results compared to the cell kill observed in a parallel experiment where naïve cultures (i.e. which had not been exposed to PDT) were subjected to PDT treatment under exactly the same conditions. The results obtained after 10 subsequent PDT treatments are shown in FIG. 6.

The results obtained from comparing cell kill contained from cultures that had been exposed to 10 consecutive PDT treatments with naïve cultures (i.e. which had not been exposed to PDT) are shown in FIG. 7. The survival was expressed as log $N_0/N$, where $N_0$ and N represent the number of CFU/ml of the untreated and treated cell suspensions. Statistical analysis by T test demonstrated that the differences between the 2 values were not significant (P>10%):

Conclusions

The photosensitization of *S. aureus* ATCC BAA-44 by Compound 10 induced no appreciable development of resistance. In fact, the efficiency of photodynamic activity of Compound 10 remained unchanged in ten subsequent photodynamic sequence sessions, even though bacterial cells, which were exposed in the previous treatments, were cultivated and re-exposed to Compound 10 and light. Therefore, treatment of bacteria using Compound 10 is a photodynamic fashion is further enhanced by the apparent lack of induction of bacterial resistance, unlike antibiotic therapies, where multi-drug resistance is significant issue.

Example E

Toxicity Profile—Selectivity of Exemplary Compounds for Bacteria

Methodology

Test compounds were screened for toxicity against cultured human skin cells using normal human epidermal keratinocytes (NHEK) and normal human dermal fibroblasts (NHDF), purchased from CellSystems Biotechnologie GmbH, Germany.

The NHEK and NHDF cells were used between passages 3 and 10. The cells were seeded with 7.5 and/or $15 \times 10^4$ cells/well (microtitreplate) and allowed to attach overnight in an incubator (37° C., 5% $CO_2$). After incubation with different concentrations of the selected photosensitisers, the cells were illuminated for fifteen minutes (Light source 236, Waldmann; 15.2 mW/cm$^2$, 13.7 J/cm$^2$) and then incubated for 24 hours in the dark.

Phototoxicity was tested by standard MTT-assay (Mossman et al., 1983, *Immunological Methods* 65:55-63). MTT is an indicator of metabolically active cells. Dependent on enzyme activity in mitochondria a colour reaction can be visualised, which can be measured by ELISA reader (540 nm). The cell viability data were normalised, i.e. the OD values of cells after PDT without photosensitisers were adjusted to one. Each experiment was repeated three times.

Results

Results of the toxicity studies in keratinocytes and fibroblasts are shown in Table 5.

TABLE 5

Survival of keratinocyte and fibroblast cells after incubation with selected test compounds and illumination ('photodynamic activity') or no illumination ('dark tosxicity'.)
(A)

| Compound 8 | | | Compound 1 | | |
|---|---|---|---|---|---|
| Concn | illumination | Survival | Concn | illumination | Survival |
| PHOTODYNAMIC ACTIVITY | | | | | |
| (a) Fibroblasts | | | | | |
| 0.01 µM | 15 min | 100% | 0.01 µM | 15 min | 100% |
| 0.1 µM | 15 min | 12% | 0.1 µM | 15 min | 39% |
| 1 µM | 15 min | 3% | 1 µM | 15 min | 2% |
| (b) Keratinocytes | | | | | |
| 0.01 µM | 15 min | 98% | 0.01 µM | 15 min | 94% |
| 0.1 µM | 15 min | 33% | 0.1 µM | 15 min | 52% |
| 1 µM | 15 min | 0.5% | 1 µM | 15 min | 0.4% |
| DARK TOXICITY | | | | | |
| (a) Fibroblasts | | | | | |
| 10 µM | N/A | 68% | 10 µM | N/A | 92% |
| 1 µM | N/A | 100% | 1 µM | N/A | 100% |
| (b) Keratinocytes | | | | | |
| 10 µM | N/A | 97% | 10 µM | N/A | 83% |
| | | | 1 µM | N/A | 100% |
| Compound 12 | | | Compound 10 | | |
| Concn | illumination | Survival | Concn | illumination | Survival |
| LIGHT TOXICITY | | | | | |
| (a) Fibroblasts | | | | | |
| 0.01 µM | 15 min | 100% | 0.01 µM | 15 min | 80% |
| 0.1 µM | 15 min | 85% | 0.1 µM | 15 min | 8% |
| 1 µM | 15 min | 1.0% | 1 µM | 15 min | 0.5% |

TABLE 5-continued

Survival of keratinocyte and fibroblast cells after incubation with selected test compounds and illumination ('photodynamic activity') or no illumination ('dark tosxicity'.)

(A)

(b) Keratinocytes

| 0.01 µM | 15 min | 97%  | 0.01 µM | 15 min | 62%  |
|---------|--------|------|---------|--------|------|
| 0.1 µM  | 15 min | 75%  | 0.1 µM  | 15 min | 1.0% |
| 1 µM    | 15 min | 0.5% |         |        |      |

DARK TOXICITY (a) Fibroblasts

| 10 µM | N/A | 95%  | 10 µM | N/A | 91%  |
|-------|-----|------|-------|-----|------|
| 1 µM  | N/A | 100% | 1 µM  | N/A | 100% |

(b) Keratinocytes

| 10 µM | N/A | 92%  | 10 µM | N/A | 51%  |
|-------|-----|------|-------|-----|------|
| 1 µM  | N/A | 100% | 1 µM  | N/A | 100% |

FIG. 8 shows the toxicity of Compound 8 against human fibroblasts and *S. aureus* BAA-44 at varying doses.

Conclusions

The above data demonstrate that compounds of the invention, for example Compound 8 (at a dose of 0.01 µM), Compound 12 (at a dose of 0.1 µM) and Compound 10 (at a dose of 0.01 µM), are preferentially toxic to bacterial cells compared to human skin cells.

In contrast, reference Compound 1 exhibits equal toxicity to bacterial and human cells.

Example F

Stability Studies

Methodology

A bespoke light source capable of delivering light of an appropriate wavelength (417 nm) was developed to activate the test compounds (Waldmann light source 236). The light source has a light intensity of 15 mW/cm$^2$ after 3 minutes at room temperature (25° C.), yielding a light dose of 14 J/cm$^2$). It consists of a light box (493 mm length×278 mm width×93.3 mm height) where the samples to be tested are placed on the top surface of the light box and illuminated from below.

Photostability of Compound 10

The photostability of the exemplary compounds was investigated using standard photodynamic procedures. A 10 µM solution of Compound 10 was prepared in phosphate-buffered saline/ethanol, as described above, and illuminated with blue light (15 mW/cm$^2$) using a light source with an absorbance maximum of 417 nm. The solution was illuminated for various periods: 10, 20 and 30 minutes. After each predetermined illumination period, the absorbance at 404 nm corresponding to the maximum absorption peak of the compound was measured. Parallel experiments were undertaken where the absorbance of Compound 10 solutions that had been kept in the dark for the same time periods as the illumination time periods were measured. Over the 30 minutes period of illumination a small loss in the absorbance value at 404 nm was observed (see FIG. 10A).

The susceptibility of the Compound 10 to photobleaching when subjected to a light at a higher fluence rate (150 mW/cm$^2$; i.e. ten times that used normally) was investigated. With this illumination system, the solution was kept in a quartz cuvette during illumination while an equivalent solution was kept in the dark. The reduction of absorbance caused by photobleaching was found to be approximately 15-20% at a concentration of 10 µM after 30 minutes illumination (See FIG. 10B).

The above results indicate that Compound 10 undergoes photobleaching much less than other porphyrins known in the literature (for example, see Reddi, et al., 2002, *Photochem. Photobiol.* 75:462-470).

Chemical Stability

The following HPLC methodology was established for the analysis of the exemplary compounds of the invention.

The method involves detection by UV at a wavelength of 420 nm, which is very specific for these compounds. In order to monitor impurities not related to the porphyrin structure (and therefore not absorbing at 420 nm) UV spectra of the whole chromatograms were also recorded between 200 nm and 700 nm by DAD (diode array detector) in certain experiments.

| Column:    | Zorbax Phenyl, 250 × 4.6 mm, 5 µm                                           |
|------------|-----------------------------------------------------------------------------|
| Eluent A:  | 1.5 g sodium dodecylsulfate + 1 mL formic acid in 1000 mL water             |
| Eluent B:  | 1.5 g sodium dodecylsulfate + 1 mL formic acid in 200 mL water + 800 mL tetrahydrofurane |

Gradient:

| Time [min] | Eluent B [%] |
|------------|--------------|
| 0          | 50           |
| 31         | 65           |
| 32         | 90           |
| 33         | 50           |
| 43         | 50           |

| Flow rate:          | 0.4 mL/min |
|---------------------|------------|
| Detection:          | 420 nm     |
| Column temperature: | 25° C.     |
| Injection volume:   | 1.0 µl     |
| Solutions:          | Porphyrin derivatives were dissolved in eluent A to give a final concentration of approximately 0.3 mg/mL |

Typical retention time of the exemplary compounds was approximately 8 minutes (18 minute runtime).

Qualitative stress tests were undertaken on the exemplary compounds of the invention. Analysis was undertaken by HPLC & LC-MS. The compounds were stress tested in solid form, in an aqueous solution and a solution made up in phosphate-buffered saline buffer. The samples were initially incubated for 7 days at 50° C. and a sample removed for testing. The samples were then incubated for a further 7 days at 70° C., samples removed as before and the samples incubated further for 7 days at 90° C. HPLC analysis of freshly prepared solutions was undertaken and compared to the samples after 7, 14 and 21 days incubation. A visual comparison of the chromatograms was then undertaken and the content of the main products and by-products as area percentage values determined (see FIG. 11).

The 3D plots of the chromatograms show no indications for additional formation of fragments (no signals at lower wavelengths)

The plot in FIG. 12 shows the sample after 21 days in PBS buffer, which showed the largest degradation effect. The results demonstrated minimal degradation on analysis of solid drug and drug in solution heated to 80° C. for a number of weeks.

Conclusions

Compounds 10 and 12 were both found to exhibit good stability and were very stable even under the stressed conditions of the test protocol. Although Compound 8 was less stable than Compounds 10 and 12, the stability demonstrated was found to be sufficient for practical use.

Stability of Exemplary Compounds in Formulations

The stability of three exemplary compounds of the invention (Compounds 8, 10 and 12) and one reference compound (Compound 1), stored at 40° C. in the dark over 8 weeks in polyethylene vials in various aqueous-based formulations, was evaluated as follows:

Sodium laureth sulphate (SLES)+water
9:1 water:ethanol
SLES+9:1 water:ethanol

UV spectra were recorded over the range 350-700 nm over a period of 7 weeks and a visual evaluation of the samples made at 8 weeks.

The results indicate that all compounds tested exhibited good stability over an eight-week period (see FIG. 13).

For Compounds 8 and 10, the stability study was extended to 17 weeks (see FIG. 14).

Example G

Distribution Studies

Human Skin Distribution

Human skin (intact) in Franz cell system was used to examine the distribution of Compounds 10 and 12 within skin compartments after 22 hours incubation at high concentration. Three separate experiments, each using one skin sample (from the same donor) was undertaken per formulation. 250 µl of each formulation was applied under occlusion and removed after 22 hours. Skin was separated and the compound content in stratum corneum, epidermis and dermis, and receiver solution determined using HPLC.

The following HPLC methodology was established for the analysis of the exemplary compounds of the invention:

HPLC system details: TSP SCM1000 membrane degasser, P4000 quaternary pump, AS3000 autosampler, UV6000LP UV/Vis PDA detector, SN4000 controller, PC1000 Ver. 3.5.1 software. Zorbax SB-Phenyl, 5 µm, 250×4.6 mm column plus a Phenyl security guard cartridge (Phenomenex). Mobile phase: 550 mL water; 450 mL tetrahydrofuran; 1.5 g sodium dodecyl sulfate and 1 mL formic acid at a flow rate of 0.8 mL/min. Injection volume was 50 µL (full loop injection) and operating temperature was 25° C. Detector was set at a wavelength of 409 nm plus UV/Vis scan (240-752 nm, step 4 nm). Typical retention time of the exemplary compounds was approximately 8 minutes (18 minute runtime).

The majority of the compounds associated with the skin were found to reside in stratum corneum. Low concentrations were detected in the epidermis (approx. 0.01 µM)—i.e. potentially anti-bacterial concentration. Lower concentrations were detected in the dermis (approx. 0.002 µM). Compounds were not detected in the receiver solution.

TABLE 6

Experiment 1: 32 µM Compound 10 in 9:1 water:ethanol

| Formulation | dose (ml) | Total recovery (%) | wash | wipe | strip 1 | strips 2-3 | strips 4-6 | strips 7-10 | epi-dermis | dermis | receptor phase |
|---|---|---|---|---|---|---|---|---|---|---|---|
| | | | | | µg/cm2 | | | | | | |
| 32 µM Cpd 10 in 9:1 water:ethanol | 0.25 | 63.00 | 0.618 | 1.880 | 0.146 | 0.079 | 0.051 | 0.032 | 0.054 | 0.035 | 0.0000 |
| | | | | | nmoles/cm2 | | | | | | |
| 32 µM Cpd 10 in 9:1 water:ethanol | 0.25 | 63.00 | 0.807 | 2.455 | 0.191 | 0.103 | 0.066 | 0.042 | 0.070 | 0.045 | 0.0000 |

| | | | tissue concentration (µM) | | |
|---|---|---|---|---|---|
| Formulation | dose (ml) | Total recovery (%) | total in strips | epidermis | dermis |
| assumed tissue thickness (µm) | | | 15 | 85 | 4000 |
| calc volume (cm3) | | | 0.0015 | 0.0085 | 0.400 |
| 32 µM Cpd 10 in 9:1 water:ethanol | 0.25 | 63.00 | 268 | 8.27 | 0.113 |

TABLE 7

Experiment 2: Direct comparison of three formulations containing 16 µM Compound 10

| Formulation | dose (ml) | total recovery (%) | wash | wipe | strip 1 | strips 2-3 | Strips 4-6 | strips 7-10 | epi-dermis | dermis | receptor phase |
|---|---|---|---|---|---|---|---|---|---|---|---|
| | | | | | µg/cm2 | | | | | | |
| 16 µM Cpd 10 + 32 µM SLES in water | 0.25 | 50.53 | 0.454 | 0.741 | 0.0031 | 0.0015 | 0.0018 | 0.0007 | 0.0028 | 0.0059 | 0.0028 |

TABLE 7-continued

Experiment 2: Direct comparison of three formulations containing 16 μM Compound 10

| | | | | | | | | | | | |
|---|---|---|---|---|---|---|---|---|---|---|---|
| 16 μM Cpd 10 in 9:1 water:ethanol | 0.25 | 53.01 | 0.564 | 0.544 | 0.0024 | 0.0023 | 0.0030 | 0.0007 | 0.0163 | 0.0088 | 0.0000 |
| 16 μM Cpd 10 + 32 μM SLES in 9:1 water:ethanol | 0.25 | 58.94 | 0.478 | 0.430 | 0.0051 | 0.0026 | 0.0026 | 0.0014 | 0.0151 | 0.0028 | 0.0000 | nmoles/cm2

| | | | | | | | | | | | |
|---|---|---|---|---|---|---|---|---|---|---|---|
| 16 μM Cpd 10 + 32 μM SLES in water | 0.25 | 50.53 | 0.593 | 0.968 | 0.0041 | 0.0020 | 0.0024 | 0.0009 | 0.0037 | 0.0077 | 0.0037 |
| 16 μM Cpd 10 in 9:1 water:ethanol | 0.25 | 53.01 | 0.736 | 0.710 | 0.0031 | 0.0031 | 0.0039 | 0.0010 | 0.0212 | 0.0115 | 0.0000 |
| 16 μM Cpd 10 + 32 μM SLES in 9:1 water:ethanol | 0.25 | 58.94 | 0.625 | 0.562 | 0.0066 | 0.0034 | 0.0034 | 0.0019 | 0.0198 | 0.0037 | 0.0000 | tissue concentration (μM)

| Formulation | dose (ml) | Total recovery (%) | total in strips | epidermis | dermis | receptor phase |
|---|---|---|---|---|---|---|
| assumed tissue thickness (μm) | | | 15 | 85 | 4000 | |
| calc volume (cm³) | | | 0.0015 | 0.0085 | 0.400 | 3.32 |
| 16 μM Cpd 10 + 32 μM SLES in water | 0.25 | 50.53 | 6.24 | 0.4373 | 0.019 | 0.0011 |
| 16 μM Cpd 10 in 9:1 water:ethanol | 0.25 | 53.01 | 7.37 | 2.4977 | 0.029 | |
| 16 μM Cpd 10 + 32 μM SLES in 9:1 water:ethanol | 0.25 | 58.94 | 10.21 | 2.3257 | 0.009 | |

Results and Conclusions

Results of the human skin distribution studies are shown above in Tables 6 and 7.

The key findings are as follows:
(i) The vast majority of Compound 10 was recovered from the surface of the stratum corneum.
(ii) Much lower, yet potentially antibacterial, concentrations of Compound 10 were recovered within the stratum corneum.
(iii) In the absence of ethanol, sub-therapeutic concentrations of Compound 10 were found in the epidermis and dermis.
(iv) In the presence of ethanol, higher concentrations of Compound 10 were found in the epidermis.
(v) No formulation led to a potentially antibacterial concentration of Compound 10 reaching the dermis.
(vi) The formulations containing SLES were the only ones in which Compound 10 was detected at very low concentration in the receptor phase.
(vii) Compound 10 distribution in the skin can, to a certain degree, be manipulated by the formulation used.

Human Skin Cell Distribution: Imaging Studies

The sub-cellular distribution of the dyes in human dermal fibroblasts (NHDF) and human dermal keratinocytes (NHEK) has been investigated, NHDF were grown on microscope slides overnight and the cells were then incubated with Compound 10 for 5 minutes, 1 and 4 hours alone or incubated cells were co-stained with organelle-specific dyes. For labelling of lysosomes and mitochondria LysoTrackerGreen (Molecular Probes) and Rhodamine G6 (Sigma) were used, respectively. Immediately after incubation sub-cellular localisation was examined by fluorescence microscopy (Zeiss Vario AxioTech, Germany) using an appropriate dual band filter set (Omega Optical) for excitation and emission. Using suitable software application, it is possible to overlay digital photographs (fluorescence) onto light microscopy photographs transparently. Therefore distribution of the dyes can be localized by one image. In addition, overlay of several digital photographs using different colour-images is also possible NHDF cells were grown overnight on microscope slides. After that, the cells were incubated with 1 μM Compound 10 (green fluorescence) for 1 hour and co-stained with (A) organelle-specific dyes for mitochondria (Rhodamine G6; 50 ng/ml, 5 minutes; red fluorescence) and nucleus (Hoechst 33342; blue fluorescence) or (B) organelle-specific dyes for lysosomes (LysoTrackerGreen; 10 μM, 2 h; green fluorescence) and nucleus (Hoechst 33342; blue fluorescence). Sub-cellular localisation was examined by fluorescence microscopy (Zeiss Vario AxioTech, Germany) using an appropriate dual band filter set (Omega Optical) for excitation and emission. Co-localisation is merged in yellow fluorescence.

Compound 10 fluorescence is localised extra-nuclearly and co-staining with mitochondria-specific Rhodamine G6 resulted in co-localisation of Compound 10 and fluorescence of mitochondria. Co-staining with lysosomal-specific dye (LysoTrackerGreen) resulted in different localization of Compound 10 and lysosomal fluorescence.

Conclusions

No nuclear association of Compound 10 was observed in nuclear material in these studied which may indicate that there is a low possibility of compound activity against DNA.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method for selectively killing bacteria, comprising administering a compound of formula I or II:

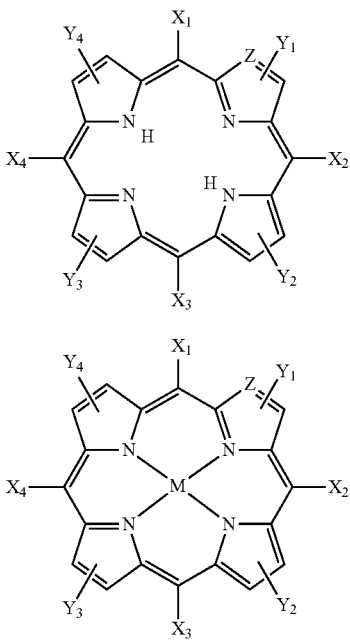

wherein:
X₁, X₂, X₃ and X₄ independently represent a hydrogen atom, a lipophilic moiety, a phenyl group, a lower alkyl, alkaryl or aralkyl group, or a cationic group of the following formula;

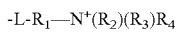

-L-R₁—N⁺(R₂)(R₃)R₄ wherein:
L is a linking moiety or is absent;
R₁ represents lower alkylene, lower alkenylene or lower alkynylene, which is optionally substituted by one or more substituents selected from lower alkyl, lower alkylene (optionally interrupted with oxygen), fluoro, OR₅, C(O)R₆, C(O)OR₇, C(O)NR₈R₉, NR₁₀R₁₁ and N⁺R₁₂R₁₃R₁₄; and
R₂, R₃ and R₄ independently represent H, aryl, lower alkyl, lower alkenyl or lower alkynyl, the latter three of which are optionally substituted by one or more substituents selected from lower alkyl, lower alkylene (optionally interrupted with oxygen), aryl, OR₅, C(O)R₆, C(O)OR₇, C(O)NR₈R₉, NR₁₀R₁₁ and N⁺R₁₂R₁₃R₁₄
Z is —CH or N; and
Y₁, Y₂, Y₃ and Y₄ are absent or independently represent aryl, lower alkyl, lower alkenyl or lower alkynyl, the latter three of which are optionally substituted by one or more substituents selected from lower alkyl, lower alkylene (optionally interrupted with oxygen), aryl, OR₅, C(O)R₆, C(O)OR₇, C(O)NR₈R₉, NR₁₀R₁₁ and N⁺R₁₂R₁₃R₁₄; and
R₅, R₆, R₇, R₈, R₉, R₁₀, R₁₁, R₁₂, R₁₃ and R₁₄ independently represent H or lower alkyl provided that at least one of X₁, X₂, X₃ and X₄ is a cationic group as defined above and at least one of X₁, X₂, X₃ and X₄ is a hydrogen atom, and
wherein M is a metallic element or a metalloid element.

2. The method according to claim 1, wherein the toxicity of the compound against a target bacterium is at least two-fold greater than the toxicity of that compound to mammalian cells, 3. The method according to claim 2, wherein the compound is substantially non-toxic to mammalian cells.

4. The method of claim 1 for use in the curative or prophylactic treatment of bacterial infections.

5. The method of claim 1, wherein the bacteria are resistant to one or more conventional antibiotic agents.

6. The method of claim 1 for treating dermatological infection.

7. The method of claim 1 for treating an infection of the lungs.

8. The method of claim 1 for treating wound infection and/or ulcers.

9. The method according to claim 1, wherein M is a divalent or trivalent metallic element.

10. The method according to claim 9, wherein M is selected from Zn (II), Cu (II), La (III), Lu (III), Y (III), In (III) Cd (II), Mg (II), Al(III), Ru, Ni(II), Mn(III), Fe(III) and Pd(II).

11. The method of claim 1, wherein M is a metalloid element.

12. The method of claim 1, wherein Y₁, Y₂, Y₃ and Y₄ are absent.

13. The method of claim 1, wherein Z is —CH.

14. The method of claim 1, wherein R₁ is an unsubstituted lower alkylene, lower alkenylene or lower alkynylene group.

15. The method of claim 1, wherein R₁ is —(CH₂)ₘ— and m is an integer between 1 and 20.

16. The method of claim 15, wherein m is an integer between 1 and 10.

17. The method of claim 16, wherein m is 3.

18. The method of claim 1, wherein one or more of R₂, R₃ and R₄ are lower alkyl, lower alkenyl or lower alkynyl groups.

19. The method of claim 18, wherein one or more of R₂, R₃ and R₄ are unsubstituted lower alkyl groups.

20. The method of claim 18, wherein at least one of R₂, R₃ and R₄ is an alkyl group which is substituted with a primary, secondary or tertiary amine group or a quaternary ammonium group.

21. The method of claim 1, wherein R₁ is —(CH₂)₃—, R₂ and R₃ are CH₃ and R₄ is —(CH₂)₃—N(CH₃)₂.

22. The method of claim 1, wherein R₁ is —(CH₂)₃—, and R₂, R₃ and R₄ are each CH₃.

23. The method of claim 1, wherein R₁ is —(CH₂)₃—, and R₂, R₃ and R₄ are each C₂H₅.

24. The method of claim 1, wherein L is selected from the group consisting of phenoxy, phenylene, sulfonyl amido, aminosulfonyl, sulfonylimino, phenylsulfonyl-amido, phenylaminosulfonyl, urea, urethane and carbamate linking moieties.

25. The method of claim 24, wherein one or more of the groups selected from the group consisting of X₁, X₂, X₃ and X₄ are

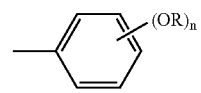

wherein R is —R₁—N⁺(R₂)(R₃)R₄, as defined in claim 1 and 'n' is an integer between 1 and 3.

26. The method of claim 24, wherein one or more of the groups selected from the group consisting of X₁, X₂, X₃ and X₄ are

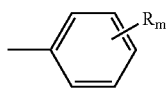

wherein R is —R₁—N⁺(R₂)(R₃)R₄, as defined in claim 1 and m is an integer between 1 and 3.

27. The method of claim 24, wherein one or more of the groups selected from the group consisting of $X_1$, $X_2$, $X_3$ and $X_4$ are

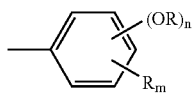

wherein each R independently is —R₁—N⁺(R₂)(R₃)R₄, as defined in claim 1 and n and m are integers between 1 and 3 and wherein the sum of n and m is an integer between 1 and 3.

28. The method of claim 24, wherein n or m is 3.

29. The method of claim 24, wherein n or m is 2.

30. The method of claim 24, wherein n, m, or both are 1.

31. The method of claim 24, wherein L is mono-substituted at the para-position.

32. The method of claim 24, wherein L is mono- or di-substituted at a meta-position(s).

33. The method of claim 24, wherein L is mono- or di-substituted at an ortho-position(s).

34. The method of claim 1, wherein the compound comprises two cationic groups, as defined in claim 1, on opposite sides of the porphyrin ring, at ring positions 5 and 15 or ring positions 10 and 20.

35. The method of claim 34, wherein $X_1$ and $X_3$ are a hydrogen atom, a lipophilic moiety, a phenyl group, a lower alkyl, alkaryl or aralkyl group and $X_2$ and $X_4$ are cationic groups, or wherein $X_2$ and $X_4$ are a hydrogen atom, a lipophilic moiety, a phenyl group, a lower alkyl, alkaryl or aralkyl group and $X_1$ and $X_3$ are cationic groups.

36. The method of claim 1, wherein the compound comprises two cationic groups at ring positions 5 and 10, or ring positions 10 and 15, or ring positions 15 and 20 or ring positions 20 and 5.

37. The method of claim 36, wherein $X_1$ and $X_2$ are hydrogen and $X_3$ and $X_4$ are cationic groups, or $X_2$ and $X_3$ are hydrogen and $X_4$ and $X_1$ are cationic groups.

38. The method of claim 37, wherein at least one of $X_1$, $X_2$, $X_3$ and $X_4$ is a lipophilic moiety.

39. The method of claim 38 wherein the lipophilic moiety is a saturated, straight-chain alkyl group of formula —(CH₂)ₚCH₃ wherein p is an integer between 1 and 22.

40. The method of claim 39 wherein p is between 1 and 18.

41. The method of claim 37, wherein none of $X_1$, $X_2$, $X_3$ and $X_4$ is a lipophilic moiety.

42. The method of claim 37, wherein none of $X_1$, $X_2$, $X_3$ and $X_4$ is a phenyl group.

43. The method of claim 1, wherein the compound is water-soluble.

44. The method of claim 1, wherein the compound is 5,15-bis-(4-{3-[(3-Dimethylamino-propyl)-dimethyl-ammonio]-propyl-oxy}-phenyl)-porphyrin dichloride.

45. The method of claim 1, wherein the compound is 5,15-bis-[4-(3-Triethylammonio-propyloxy)-phenyl]-porphyrin di-chloride.

46. The method of claim 1, wherein the compound is 5,15-bis-[3-(3-Trimethylammonio-propyloxy)-phenyl]-porphyrin dichloride.

47. The method of claim 1, wherein the compound is 5,15-bis-[4-(3-Trimethylammonio-propyloxy)-phenyl]-porphyrin dichloride.

48. The method of claim 1, wherein the compound is 5-[3,5-bis-(3-Trimethylammonio-propyloxy)-phenyl]-15-undecyl-porphyrin dichloride.

49. The method of claim 1, wherein the compound is 5-{4-[3-Dimethyl-(3-dimethylaminopropyl)-ammonio-propyl-oxy]-phenyl}-15-(4-dodecyloxy-phenyl)-porphyrin chloride.

50. The method of claim 1, wherein the compound is 3-[({3-[(3-{4-[15-(4-Dodecyloxy-phenyl)-porphyrin-5-yl]-phenoxy}-propyl)-dimethyl-ammonio]-propyl}-dimethyl-ammonio)-propyl]-trimethyl-ammonium trichloride.

51. The method of claim 1, wherein the compound is 5,15-bis-[3-(3-Trimethylamminonio-propyloxy)-phenyl]-10-undecyl-porphyrin dichloride.

52. The method of claim 1,wherein the compound is 5-{4-[3-Dimethyl-(3-trimethylammonio-propyl)-ammonio-propyloxy]-phenyl}-15-(4-dodecyloxy-phenyl)-porphyrin dichloride.

53. The method of claim 1, wherein the compound is 5-[4-(3-Dimethyldecyl-ammoniopropyloxy)-phenyl]-15-{4-[3-di-methyl-(3-dimethylaminopropyl)-ammoniopropyloxy]-phenyl}-porphyrin dichloride.

* * * * *

UNITED STATES PATENT AND TRADEMARK OFFICE
CERTIFICATE OF CORRECTION

| | | |
|---|---|---|
| PATENT NO. | : 8,084,602 B2 | Page 1 of 1 |
| APPLICATION NO. | : 11/562183 | |
| DATED | : December 27, 2011 | |
| INVENTOR(S) | : William Love et al. | |

It is certified that error appears in the above-identified patent and that said Letters Patent is hereby corrected as shown below:

Claim 2, Column 85, Line 67, replace "cells," with --cells.--.

Signed and Sealed this
Sixteenth Day of October, 2012

David J. Kappos
*Director of the United States Patent and Trademark Office*